United States Patent
Freier

(10) Patent No.: US 11,111,494 B2
(45) Date of Patent: Sep. 7, 2021

(54) COMPOSITIONS FOR MODULATING ATAXIN 2 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/387,308

(22) Filed: Apr. 17, 2019

(65) Prior Publication Data

US 2020/0087661 A1    Mar. 19, 2020

Related U.S. Application Data

(62) Division of application No. 15/127,358, filed as application No. PCT/US2015/021608 on Mar. 19, 2015, now Pat. No. 10,308,934.

(60) Provisional application No. 61/955,705, filed on Mar. 19, 2014, provisional application No. 61/982,131, filed on Apr. 21, 2014.

(51) Int. Cl.
| | |
|---|---|
| *A61K 48/00* | (2006.01) |
| *C12N 15/11* | (2006.01) |
| *C07H 21/02* | (2006.01) |
| *C07H 21/04* | (2006.01) |
| *C12N 15/113* | (2010.01) |

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/345* (2013.01); *C12N 2310/346* (2013.01)

(58) Field of Classification Search
CPC .............. C12N 15/113; C12N 15/1138; C12N 2310/11; C12N 2310/315; C12N 2310/321; C12N 2310/3231; C12N 2310/3341; C12N 2310/341; C12N 2310/346
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |

(Continued)

FOREIGN PATENT DOCUMENTS

| | | |
|---|---|---|
| EP | 0878543 A1 | 11/1998 |
| EP | 1752536 A1 | 2/2007 |

(Continued)

OTHER PUBLICATIONS

Grünweller et al. (Nucleic Acids Research, 2003 vol. 31:3185-3193).*
Ataxin-2 Wikipedia. Downloaded on Jul. 16, 2018 from http://en.wikipedia.org/wiki/Ataxin-2.
Bezprozvanny et al., "Therapeutic prospects for spinocerebellar ataxia type 2 and 3." Drugs Future (2009) 34(12):1-17.
Branch et al., "A good antisense molecule is hard to find," TIBS (1998) 23:45-50.

(Continued)

*Primary Examiner* — Terra C Gibbs
(74) *Attorney, Agent, or Firm* — McNeill Baur PLLC

(57) ABSTRACT

Disclosed herein are antisense compounds and methods for decreasing Ataxin 2 mRNA and protein expression. Such methods, compounds, and compositions are useful to treat, prevent, or ameliorate Ataxin 2 associated diseases, disorders, and conditions. Such Ataxin 2 associated diseases include spinocerebellar ataxia type 2 (SCA2), amyotropic sclerosis (ALS), and parkinsonism.

27 Claims, No Drawings

Specification includes a Sequence Listing.

(56) References Cited

U.S. PATENT DOCUMENTS

| | | |
|---|---|---|
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,673,535 B1 | 1/2004 | Pulst |
| 6,770,748 B2 | 8/2004 | Imanishi et al. |
| 6,844,431 B1 | 1/2005 | Pulst |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,374,927 B2 | 5/2008 | Palma et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,888,497 B2 | 2/2011 | Bentwich et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,728,736 B2 | 5/2014 | Leamon et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 10,006,027 B2 | 6/2018 | Bennett et al. |
| 10,308,934 B2 | 6/2019 | Freier |
| 10,533,178 B2 | 1/2020 | Bennett et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0220132 A1 | 11/2004 | Kaemmerer |
| 2005/0026164 A1 | 2/2005 | Zhou |
| 2005/0042646 A1 | 2/2005 | Davidson et al. |
| 2005/0100885 A1 | 5/2005 | Crooke et al. |
| 2005/0130923 A1 | 6/2005 | Bhat et al. |
| 2005/0209178 A1 | 9/2005 | Pulst |
| 2005/0244851 A1 | 11/2005 | Blume et al. |

(56) References Cited

U.S. PATENT DOCUMENTS

| | | |
|---|---|---|
| 2005/0255487 A1 | 11/2005 | Khvorova et al. |
| 2006/0148740 A1 | 7/2006 | Platenburg |
| 2006/0270727 A1 | 11/2006 | Melander et al. |
| 2007/0031844 A1 | 2/2007 | Khvorova et al. |
| 2007/0224624 A1 | 9/2007 | Pulst |
| 2008/0039618 A1 | 2/2008 | Allerson et al. |
| 2008/0113351 A1 | 5/2008 | Naito et al. |
| 2010/0190837 A1 | 7/2010 | Migawa et al. |
| 2010/0197762 A1 | 8/2010 | Swayze et al. |
| 2011/0054005 A1 | 3/2011 | Naito et al. |
| 2011/0142789 A1 | 6/2011 | Gitler et al. |
| 2013/0130378 A1 | 5/2013 | Manoharan et al. |
| 2013/0172399 A1 | 7/2013 | Corey et al. |
| 2013/0225659 A1 | 8/2013 | Bennett et al. |
| 2014/0107330 A1 | 4/2014 | Freier et al. |
| 2014/0303238 A1 | 10/2014 | Linsley et al. |
| 2015/0018540 A1 | 1/2015 | Prakash et al. |
| 2015/0141320 A1 | 5/2015 | Krieg et al. |
| 2015/0184153 A1 | 7/2015 | Freier et al. |
| 2015/0191727 A1 | 7/2015 | Migawa et al. |
| 2015/0259679 A1 | 9/2015 | Bennett et al. |
| 2015/0267195 A1 | 9/2015 | Seth et al. |
| 2015/0275212 A1 | 10/2015 | Albaek et al. |
| 2016/0053254 A1 | 2/2016 | Kimpe et al. |
| 2017/0175113 A1 | 6/2017 | Bennett et al. |
| 2017/0175114 A1 | 6/2017 | Freier et al. |
| 2019/0002887 A1 | 1/2019 | Rigo |
| 2019/0017047 A1 | 1/2019 | Bennett et al. |
| 2020/0056179 A1 | 2/2020 | Freier et al. |

FOREIGN PATENT DOCUMENTS

| | | | |
|---|---|---|---|
| EP | 2399611 A2 | 12/2011 | |
| WO | WO 2017/117496 | 7/1917 | |
| WO | WO 1997/42314 | 11/1997 | |
| WO | WO 2004/003201 | 1/2004 | |
| WO | WO 2004/047872 | 6/2004 | |
| WO | WO 2004/070062 | 8/2004 | |
| WO | WO 2005/116204 | 12/2005 | |
| WO | WO 2005/116212 | 12/2005 | |
| WO | WO 2006/021814 | 3/2006 | |
| WO | WO 2006/131925 | 12/2006 | |
| WO | WO 2007/106407 | 9/2007 | |
| WO | WO 2008/109379 | 9/2008 | |
| WO | WO 2008/109450 | 9/2008 | |
| WO | WO 2008/152636 | 12/2008 | |
| WO | WO 2009/046141 | 4/2009 | |
| WO | WO 2010/014592 | 2/2010 | |
| WO | WO 2011/006121 | 1/2011 | |
| WO | WO-2011073326 A2 * | 6/2011 | ............. A61P 31/12 |
| WO | WO 2011/097641 | 8/2011 | |
| WO | WO 2012/012467 | 1/2012 | |
| WO | WO 2012/079578 | 6/2012 | |
| WO | WO 2012/149438 | 11/2012 | |
| WO | WO 2013/081864 | 6/2013 | |
| WO | WO 2013/162363 | 10/2013 | |
| WO | WO 2013/173645 | 11/2013 | |
| WO | WO 2015/002971 | 1/2015 | |
| WO | WO 2015/072438 | 5/2015 | |
| WO | WO 2015/143245 | 9/2015 | |
| WO | WO 2015/143246 | 9/2015 | |
| WO | WO 2020/023737 | 1/2020 | |

OTHER PUBLICATIONS

Burke et al., "Huntingtin and DRPLA proteins selectively interact with the enzyme GAPDH." Nat. Med. (1996) 2(3):347-350.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Ciosk et al., "ATX-2, the C. elegans ortholog of ataxia 2, functions in translational regulation in the germline." Development (2004) 131(19):4831-4841.
Corrado et al., "ATXN-2 CAG repeat expansions are interrupted in ALS patients." Hum. Genet. (2011) 130(4):575-580.
Crooke, ST., et al., "Antisense Drug Technology" Second Edition, CRC Press (2008) Chapters 1-28.
Deleavy et al., "Designing chemically modified oligonucleotides for targeted gene silencing" Chem Biol (2012) 19(8): 937-954.
Duvick et al., "SCA1-like disease in mice expressing wild-type ataxia-1 with a serine to aspartic acid replacement at residue 776." Neuron (2010) 67(6): 929-935.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elden et al., "Ataxin-2 intermediate-length polyglutamine expansions are associated with increased risk for ALS." Nature (2010) 466: 1069-1075.
Elden et al., "Ataxin-2 localization in ALS and FTLD-TDP and TDP-43 localization in SCA2" Nature (2010) 466: 1069-1075 (Supplementary Information).
European partial search report for 15765851.9 dated Oct. 25, 2017.
Extended EP Search Report for 15765851.9 dated Jan. 30, 2018.
Evers et al., "Targeting Several CAG Expansion Diseases by a Single Antisense Oligonucleotide" PLoS One (2011) 6(9): e24308.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
GenBank: NM_002973.3, Homo sapiens ataxin 2 (ATXN2), transcript variant 1, mRNA, NCBI Accession No. NM_002973 (2015) (retrieved from the internet Jun. 28, 2017: https://www.ncbi.nlm.nih.gov/nuccore/171543894/).
GenBank: NT_009775.17 (truncated from nucleotides 2465000 to 2616000) Homo sapiens chromosome 12 genomic contig, GRCh37.p13 Primary Assembly (2013) (retrieved from the internet Jun. 28, 2017: https://www.ncbi.nlm.nih.gov/nuccore/NT 009775.17?report—genbank).
GenBank: BX410018.2, BX410018 Homo sapiens Fetal Brain Homo sapiens cDNA clone CS0DF030YB075-PRIME, mRNA sequence; (2003) (retrieved from the internet Jun. 28, 2017: https://www.ncbi.nlm.nih.gov/nucest/BX410018.2).
Heuvel et al., "Taking a risk: a therapeutic focus on ataxin-2 in amyotrophic lateral sclerosis?" Trends Mol Med (2014) 20(1): 25-35.
Huynh et al., "Expression of ataxin-2 in brains from normal individuals and patients with Alzheimer's disease and spinocerebellar ataxia 2." Ann. Neurol. (1999) 45: 232-241.
Huynh et al., "Expansion of the polyQ repeat in ataxin-2 alters its Golgi localization, disrupts the Golgi complex and causes cell death." Hum. Mol. Genet. (2003) 12: 1485-1496.
International Search Report for application PCT/US2015/021607 dated Jun. 29, 2015.
International Search Report for application PCT/US2015/021608 dated Jul. 1, 2015.
International Search Report for application PCT/US2016/069406 dated Mar. 31, 2017.
Kim et al., "Importance of low-range CAG expansion and CAA interruption in SCA2 Parkinsonism." Arch. Neurol. (2007) 64(10): 1510-1518.
Koshy et al., "Spinocerebellar ataxia type-1 and spinobulbar muscular atrophy gene products interact with glyceraldehyde-3-phosphate dehydrogenase" Hum. Mol. Genet. (1996) 5(9): 1311-1318.
Lajoie et al., "Formation and toxicity of soluble polyglutamine oligomers in living cells." PLoS One (2010) 5(12): e15245 1-15.
Lou Gehrig's Disease (ALS): Prevention | Florida Hospital. Downloaded on Jul. 16, 2018 from https://www.floridahospital.com/lou-gehrigs-disease-als/prevention-lou-gehrigs-disease-als.
Lovett-Racke et al., Thempeutic Potential of Small Interfering RNA for Central Nervous System Diseases. Archives of Neurobiology (2005) 62:1810-1813.
Magana et al., "Spinocerebellar ataxia type 2: clinical presentation, molecular mechanisms, and therapeutic perspectives" Mol Neurobiol (2013) 47(1): 90-104.

(56) References Cited

OTHER PUBLICATIONS

Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
New England Biolabs 1998/99 Catalog (cover page and pp. 121 and 284).
Nonhoff et al., "Ataxia-2 interacts with the DEAD/H-box RNA helicase DDX6 and interferes with P-bodies and stress granules." Mol. Biol. Cell (2007) 18(4):1385-1396.
Nonis et al., "Ataxia-2 associates with the endocytosis complex and affects EGF receptor trafficking" Cell Signal (2008) 20(10):1725-1739.
Parkinson's Disease—Symptoms and causes—Mayo Clinic. Downnloaded on Jul. 16, 2018 from https://www.mayoclinic.org/diseases-conditions/parkinsons-disease/symptoms-causes/syc-20376055.
Pulst S.M. (ed.) "Inherited Ataxias: An Introduction" Genetics of Movement Disorders. Elsevier, Inc., Amsterdam, published Oct. 3, 2002, pp. 19-34.
Pulst Sm., "Rare mendelian diseases: pathways to therapy development" Oral presentation, American Academy of Neurology Annual Meeting, Philadelphia, PA, Apr. 29, 2014.
Ramachandran, P. "RNA interference therapy for the Spinocerebellar ataxias." Thesis, May 2014, University of Iowa, pp. 1-140.
Reynolds et al., "Rational siRNA design for RNA interference" Nature Biotechnology (2004) 22(3):326-330.
Ross et al., "Ataxin-2 repeat-length variation and neurodegeneration." Hum. Mol. Genet. (2011) 20(16): 3207-3212.
Sanghvi et al., "Heterocyclic Base Modifications in Nucleic Acids and Their Applications in Antisense Oligonucleotides" Antisense Research and Applications (1993) pp. 273-288.
Satterfield et al., "Ataxin-2 and its *Drosophila* homolog, ATX2, physically assemble with polyribosomes." Hum. Mol. Genet. (2006) 15(16):2523-2532.
Scoles et al., "Antisense oligonucleotides for the treatment of spinocerebellar ataxia type 2 (SCA2)" AAN Annual Meeting abstract published online Feb. 26, 2015; Neurology (2015) 82(Meeting Abstracts): S32.002.
Scoles et al, Antisense oligonucleotides for the treatment of spinocerebellar ataxia type 2 (SCA2), 5th Ataxia Investigators Meeting (AIM) meeting abstract presented Mar. 20, 2014.
Scoles et al., "ETS1 regulates the expression of ATXN2" Human Mol Genetics (2012) 21(23): 5048-65.
Scoles et al., "Treatment of Spinocerebellar Ataxia Type 2 (SCA2) with MOE Antisense Oligonucleotides." AAN Annual Meeting abstract published online Feb. 26, 2014; Neurology (2014) 82(10 Supplement): S47.006.
Scoles et al., "ATXN2 Is Regulated by a Promoter Associated Antisense Long Noncoding RNA (lncRNA)" Neurology (2013) 80: P05030.
Seth et al., "Short Antisense Oligonucleotides with Novel 2'-4' Conformationally Restricted Nucleoside Analogues Show Improved Potency Without Increased Toxicity in Animals " J Med Chem (2009) 52:10-13.
Shen et al., "Research on (CAG)n mutation detection of Spinocerebellar ataxia type 2" Chinese J Int Med (2000) 39(4): 259-261.
Shibata et al., "A novel protein with RNA-binding motifs interacts with ataxin-2." Hum. Mol. Genet. (2000) 9(9): 1303-1313.
Van Damme et al., "Expanded ATXN2 CAG repeat size in ALS identifies genetic overlap between ALS and SCA2." Neurology (2011) 76(24):2066-2072.
Woolf et al. "Specificity of antisense oligonucleotides in vivo" PNAS (1992) 89:7305-7309.
Yamanaka et al., "Transcription factor sequestration by polyglutamine proteins." Methods Mol. Biol. (2010) 648:215-229.
Zangemeister-Wittke et al., "A novel bispecific antisense oligonucleotide inhibiting both bcl-2 and bcl-xL expression efficiently induces apoptosis in tumor cells" Clin Cancer Res (2000) 6: 2547-2555.
Chiu et al., "Age-Dependent Penetrance of Disease in a Transgenic Mouse Model of Familial Amyotrophic Lateral Sclerosis," Mol and Cell Neurosci, 1995, 6:349-362.
Frey et al., "Early and Selective Loss of Neuromuscular Synapse Subtypes with Low Sprouting Competence in Motoneuron Diseases," J Neurosci, 2000, 20(7):2534-2542.
Gurney et al., "Motor Neuron Degeneration in Mice that Express a Human Cu,Zn Superoxide Dismutase Mutation," Science, 1994, 264:1772-1775.
Ito et al., "Treatment with edaravone, initiated at symptom onset, slows motor decline and decreases SOD1 deposition in ALS mice," Experimental Neurology, 2008, 213:448-455.
Philips et al., "Rodent Models of Amyotrophic Lateral Sclerosis," Curr Protoc Pharmacol, 2015, 69: 1-21.
Pun et al., "Selective Vulnerability and Pruning of Phasic Motoneuron Axons in Motoneuron Disease Alleviated by CTNF," Nat Neurosci, 2006, 9:408-419.
Takei et al., "Edaravone and its Clinical Development for Amyotrophic Lateral Sclerosis," Amyotrophic Lateral Sclerosis and Frontotemporal Degeneration, 2017, 18:5-10.
Van Blitterswijk et al., "Ataxin-2 as potential disease modifier in C9ORF72 expansion carriers" Neurobiology of Aging (2014) 35: e13-e17.

\* cited by examiner

COMPOSITIONS FOR MODULATING ATAXIN 2 EXPRESSION

SEQUENCE LISTING

The present application is being filed along with a Sequence Listing in electronic format. The Sequence Listing is provided as a file entitled BIOL0239USC1SEQ_ST25.txt created Apr. 17, 2019, which is 232 Kb in size. The information in the electronic format of the sequence listing is incorporated herein by reference in its entirety.

FIELD

Provided are compositions and methods for reducing expression of Ataxin 2 (ATXN2) mRNA and protein in an animal. Such methods are useful to treat, prevent, or ameliorate neurodegenerative diseases, including spinocerebellar ataxia type 2 (SCA2), amyotrophic lateral sclerosis (ALS), and parkinsonism by inhibiting expression of Ataxin 2 by inhibiting expression of Ataxin 2 in an animal.

BACKGROUND

Spinocerebellar ataxia type 2 (SCA2) is an autosomal dominant neurodegenerative disease characterized by progressive functional and cell loss of neurons in the cerebellum, brain stem and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements and other neurologic features such as neuropathy (Pulst, S. M. (ed.), *Genetics of Movement Disorders*. Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.*, 2007, 64: 1510-1518; Ross et al., *Hum. Mol. Genet.*, 2011, 20: 3207-3212; Corrado et al., *Hum. Genet.*, 2011, 130: 575-580; Elden et al., *Nature*, 2010, 466: 1069-1075; Van Damme et al., *Neurology*, 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One*, 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.*, 1999, 45: 232-241). Functions gained in polyQ-expanded ataxin-2 may include anomalous accumulation in Golgi bodies (Huynh et al., *Hum. Mol. Genet.*, 2003, 12: 1485-1496), gain-of-normal functions (Duvick et al., *Neuron*, 2010, 67: 929-935) and sequestering of transcription factors (TFs) and glyceraldehyde-3-phosphate dehydrogenase like for other polyQ proteins (Yamanaka et al., *Methods Mol. Biol.*, 2010: 648, 215-229; Koshy et al., *Hum. Mol. Genet.*, 1996, 5: 1311-1318; Burke et al., *Nat. Med.*, 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell*, 2007, 18: 1385-1396). Ataxin-2 overexpression interfered with the P-body assembly, while underexpression interfered with stress granule assembly (Nonhoff et al., *Mol. Biol. Cell*, 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.*, 2000, 9: 1303-1313; Ciosk et al., *Development*, 2004, 131: 4831-4841; Satterfield et al., *Hum. Mol. Genet.*, 2006, 15: 2523-2532). Ataxin-2 is a regulator of EGF receptor internalization and signaling by the way of its interactions with SRC kinase and the endocytic protein CIN85 (Nonis et al., *Cell Signal.*, 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature*, 2010, 466: 1069-1075; Van Damme et al., *Neurology*, 2011, 76: 2066-2072).

Currently there is a lack of acceptable options for treating such neurodegenerative diseases. It is therefore an object herein to provide methods for the treatment of such diseases.

SUMMARY

Provided herein are methods, compounds, and compositions for modulating expression of Ataxin 2 (ATXN2) mRNA and protein. In certain embodiments, compounds useful for modulating expression of Ataxin 2 mRNA and protein are antisense compounds. In certain embodiments, the antisense compounds are modified oligonucleotides.

In certain embodiments, modulation can occur in a cell or tissue. In certain embodiments, the cell or tissue is in an animal. In certain embodiments, the animal is a human. In certain embodiments, Ataxin 2 mRNA levels are reduced. In certain embodiments, Ataxin 2 protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such Ataxin 2 related diseases, disorders, and conditions are neurodegenerative diseases. In certain embodiments, such neurodegenerative diseases, disorders, and conditions include spinocerebellar ataxia type 2 (SCA2), amyotrophic lateral sclerosis (ALS), and parkinsonism.

Such diseases, disorders, and conditions can have one or more risk factors, causes, or outcomes in common. Certain risk factors and causes for development of neurodegenerative disorder include growing older, having a personal or family history, or genetic predisposition. Certain symptoms and outcomes associated with development of a neurodegenerative disorder include but are not limited to: ataxia, speech and swallowing difficulties, rigidity, tremors, ophthalmoplegia, saccadic slowing, peripheral neuropathy, atrophy, dystonia, chorea, and dementia.

In certain embodiments, methods of treatment include administering an Ataxin 2 antisense compound to an individual in need thereof. In certain embodiments, methods of treatment include administering an Ataxin 2 modified oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and"

means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxyethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Ataxin 2", it is implied that the Ataxin 2 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Ataxin 2" means the mammalian gene Ataxin 2 (ATXN2), including the human gene Ataxin 2 (ATXN2). Human Ataxin 2 has been mapped to human chromosome 12q24.1.

"Ataxin 2 associated disease" means any disease associated with any Ataxin 2 nucleic acid or expression product thereof. Such diseases may include a neurodegenerative disease. Such neurodegenerative diseases may include spinocerebellar ataxia type 2 (SCA2), amyotrophic lateral sclerosis (ALS), and parkinsonism.

"Ataxin 2 mRNA" means any messenger RNA expression product of a DNA sequence encoding Ataxin 2.

"Ataxin 2 nucleic acid" means any nucleic acid encoding Ataxin 2. For example, in certain embodiments, an Ataxin 2 nucleic acid includes a DNA sequence encoding Ataxin 2, an RNA sequence transcribed from DNA encoding Ataxin 2 (including genomic DNA comprising introns and exons), and an mRNA sequence encoding Ataxin 2. "Ataxin 2 mRNA" means an mRNA encoding an Ataxin 2 protein.

"Ataxin 2 protein" means the polypeptide expression product of an Ataxin 2 nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'—O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having an Ataxin 2 associated disease" means identifying an animal having been diagnosed with an Ataxin 2 associated disease or predisposed to develop an Ataxin 2 associated disease. Individuals predisposed to develop an Ataxin 2 associated disease include those having one or more risk factors for developing an Ataxin 2 associated disease, including, growing older, having a personal or family history, or genetic predisposition of one or more Ataxin 2 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting Ataxin 2" means reducing the level or expression of an Ataxin 2 mRNA and/or protein. In certain embodiments, Ataxin 2 mRNA and/or protein levels are inhibited in the presence of an antisense compound targeting Ataxin 2, including an antisense oligonucleotide targeting Ataxin 2, as compared to expression of Ataxin 2 mRNA and/or protein levels in the absence of an Ataxin 2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'—(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

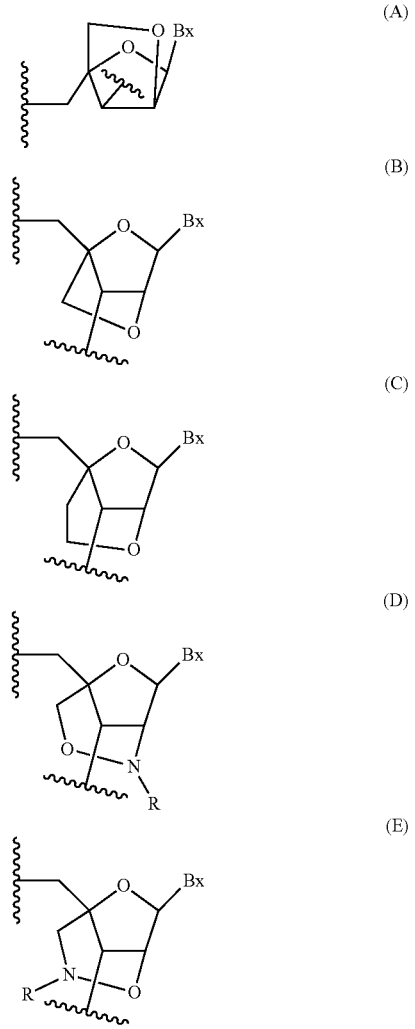

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'—(CH$_2$)$_2$-2', (CH$_2$)$_3$-2', 4'—CH$_2$—O-2', 4'—(CH$_2$)2-O-2', 4'—CH$_2$—O—N(R$_1$)-2' and 4'-CH$_2$—N(R$_1$)—O-2'- bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$-0-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to Ataxin 2 is a pharmaceutical agent.

"Pharmaceutical composition" means a mixture of substances suitable for administering to a subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

CERTAIN EMBODIMENTS

Certain embodiments provide methods, compounds, and compositions for inhibiting Ataxin 2 mRNA and protein expression. Certain embodiments provide methods, compounds, and composition for decreasing Ataxin 2 mRNA and protein levels.

Certain embodiments provide antisense compounds targeted to an Ataxin 2 nucleic acid. In certain embodiments, the Ataxin 2 nucleic acid is the sequence set forth in GENBANK Accession No. NM_002973.3 (incorporated herein as SEQ ID NO: 1), the complement of GENBANK Accession No. NT_009775.17 truncated from nucleotides 2465000 to U.S. Pat. No. 2,616,000 (incorporated herein as SEQ ID NO: 2) and GENBANK Accession No. BX410018.2 (incorporated herein as SEQ ID NO: 3).

Certain embodiments provide methods for the treatment, prevention, or amelioration of diseases, disorders, and conditions associated with Ataxin 2 in an individual in need thereof. Also contemplated are methods for the preparation of a medicament for the treatment, prevention, or amelioration of a disease, disorder, or condition associated with Ataxin 2. Ataxin 2 associated diseases, disorders, and conditions include neurodegenerative diseases. In certain embodiments, Ataxin 2 associated diseases include spinocerebellar ataxia type 2 (SCA2), amyotrophic lateral sclerosis (ALS), and parkinsonism.

Certain embodiments provide compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 11-165.

In certain embodiments the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1, SEQ ID NO: 2, or SEQ ID NO: 3.

In certain embodiments, the compound is a single-stranded modified oligonucleotide.

In certain embodiments, at least one internucleoside linkage of the modified oligonucleotide is a modified internucleoside linkage.

In certain embodiments, at least one modified internucleoside linkage is a phosphorothioate internucleoside linkage.

In certain embodiments, each modified internucleoside linkage is a phosphorothioate internucleoside linkage.

In certain embodiments, at least one internucleoside linkage is a phosphodiester internucleoside linkage.

In certain embodiments, at least one internucleoside linkage is a phosphorothioate linkage and at least one internucleoside linkage is a phosphodiester linkage.

In certain embodiments, at least one nucleoside comprises a modified nucleobase.

In certain embodiments, the modified nucleobase is a 5-methylcytosine.

In certain embodiments, at least one nucleoside of the modified oligonucleotide comprises a modified sugar.

In certain embodiments, at least one modified sugar is a bicyclic sugar.

In certain embodiments, the bicyclic sugar comprises a a chemical link between the 2' and 4' position of the sugar 4'-CH2-N(R)—O-2' bridge wherein R is, independently, H, C1-C12 alkyl, or a protecting group.

In certain embodiments, the bicyclic sugar comprises a 4'-CH2-N(R)—O-2' bridge wherein R is, independently, H, C1-C12 alkyl, or a protecting group.

In certain embodiments, at least one modified sugar comprises a 2'-O-methoxyethyl group.

In certain embodiments, the modified sugar comprises a 2'-O(CH$_2$)$_2$—OCH$_3$ group.

In certain embodiments, the modified oligonucleotide comprises:
 a gap segment consisting of 10 linked deoxynucleosides;
 a 5' wing segment consisting of 5 linked nucleosides; and
 a 3' wing segment consisting of 5 linked nucleosides;
wherein the gap segment is positioned between the 5' wing segment and the 3' wing segment and wherein each nucleoside of each wing segment comprises a modified sugar.

In certain embodiments, the modified oligonucleotide consists of 20 linked nucleosides.

Certain embodiments provide compositions comprising any compound described herein or salt thereof and at least one of a pharmaceutically acceptable carrier or diluent.

Certain embodiments provide methods comprising administering to an animal any compound or composition described herein.

In certain embodiments, the animal is a human.

In certain embodiments, administering the compound prevents, treats, ameliorates, or slows progression of an Ataxin 2 associated disease, disorder or condition.

In certain embodiments, the Ataxin 2 disease, disorder or condition spinocerebellar ataxia type 2 (SCA2), amyotrophic lateral sclerosis (ALS), and parkinsonism.

Certain embodiments provide use of any of the compounds or compositions of described herein for the manufacture of a medicament for treating a neurodegenerative disorder.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an Ataxin 2 nucleic acid is 12 to 30 subunits in length. In certain embodiments, an antisense compound targeted to an Ataxin 2 nucleic acid is 12 to 25 subunits in length. In certain embodiments, an antisense compound targeted to an Ataxin 2 nucleic acid is 12 to 22 subunits in length. In certain embodiments, an antisense compound targeted to an Ataxin 2 nucleic acid is 14 to 20 subunits in length. In certain embodiments, an antisense compound targeted to an Ataxin 2 nucleic acid is 15 to 25 subunits in length. In certain embodiments, an antisense compound targeted to an Ataxin 2 nucleic acid is 18 to 22 subunits in length. In certain embodiments, an antisense compound targeted to an Ataxin 2 nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to an Ataxin 2 nucleic acid is 12 subunits in length. In certain embodiments, an antisense compound targeted to an Ataxin 2 nucleic acid is 13 subunits in length. In certain embodiments, an antisense compound targeted to an Ataxin 2 nucleic acid is 14 subunits in length. In certain embodiments, an antisense compound targeted to an Ataxin 2 nucleic acid is 15 subunits in length. In certain embodiments, an antisense compound targeted to an Ataxin 2 nucleic acid is 16 subunits in length. In certain embodiments, an antisense compound targeted to an Ataxin 2 nucleic acid is 17 subunits in length. In certain embodiments, an antisense compound targeted to an Ataxin 2 nucleic acid is 18 subunits in length. In certain embodiments, an antisense compound targeted to an Ataxin 2 nucleic acid is 19 subunits in length. In certain embodiments, an antisense compound targeted to an Ataxin 2 nucleic acid is 20 subunits in length. In certain embodiments, an antisense compound targeted to an Ataxin 2 nucleic acid is 21 subunits in length. In certain embodiments, an antisense compound targeted to an Ataxin 2 nucleic acid is 22 subunits in length. In certain embodiments, an antisense compound targeted to an Ataxin 2 nucleic acid is 23 subunits in length. In certain embodiments, an antisense compound targeted to an Ataxin 2 nucleic acid is 24 subunits in length. In certain embodiments, an antisense compound targeted to an Ataxin 2 nucleic acid is 25 subunits in length. In certain embodiments, an antisense compound targeted to an Ataxin 2 nucleic acid is 26 subunits in length. In certain embodiments, an antisense compound targeted to an Ataxin 2 nucleic acid is 27 subunits in length. In certain embodiments, an antisense compound targeted to an Ataxin 2 nucleic acid is 28 subunits in length. In certain embodiments, an antisense compound targeted to an Ataxin 2 nucleic acid is 29 subunits in length. In certain embodiments, an antisense compound targeted to an Ataxin 2 nucleic acid is 30 subunits in length. In certain embodiments, the antisense compound targeted to an Ataxin 2 nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to an Ataxin 2 nucleic acid may be shortened or truncated. For example, a single subunit may be deleted from the 5' end (5' truncation), or alternatively from the 3' end (3' truncation). A shortened or truncated antisense compound targeted to an Ataxin 2 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358,1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an Ataxin 2 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'—$(CH_2)$n-O-2' bridge, where n=1 or n=2 and 4'-$CH_2$—O—$CH_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X—Y—Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-6.

In certain embodiments, gapmers provided herein include, for example 18-mers having a motif of 6-8-4.

In certain embodiments, gapmers provided herein include, for example 18-mers having a motif of 5-7-6.

Target Nucleic Acids, Target Regions and Nucleotide Sequences

Nucleotide sequences that encode Ataxin 2 include, without limitation, the following: GENBANK Accession No. NM_002973.3 (incorporated herein as SEQ ID NO: 1), the complement of GENBANK Accession No. NT_009775.17 truncated from nucleotides 2465000 to U.S. Pat. No. 2,616, 000 (incorporated herein as SEQ ID NO: 2) and GENBANK Accession No. BX410018.2 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Ataxin 2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Ataxin 2 mRNA levels are indicative of inhibition of Ataxin 2 expression. Reductions in levels of an Ataxin 2 protein are also indicative of inhibition of target mRNA expression. Phenotypic changes are indicative of inhibition of Ataxin 2 expression. Improvement in neurological function is indicative of inhibition of Ataxin 2 expression. Improved motor function and memory are indicative of inhibition of Ataxin 2 expression.

Hybridization

In some embodiments, hybridization occurs between an antisense compound disclosed herein and an Ataxin 2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an Ataxin 2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Ataxin 2 nucleic acid).

Non-complementary nucleobases between an antisense compound and an Ataxin 2 nucleic acid may be tolerated provided that the antisense compound remains able to specifically hybridize to a target nucleic acid. Moreover, an antisense compound may hybridize over one or more segments of an Ataxin 2 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Ataxin 2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Ataxin 2 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Ataxin 2 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Ataxin 2 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

MODIFICATIONS

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Ataxin 2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or 5), 4'-S, 2'-F, 2'-$OCH_3$, 2'-$OCH_2CH_3$, 2'—$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—N($R_m$)($R_n$), O—$CH_2$—C(=O)—N($R_m$)($R_n$), and O—$CH_2$—C(=O)—N($R_l$)—$(CH_2)_2$—N($R_m$)($R_n$), where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2'; 4'—$(CH_2)_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C—(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Serial Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)2-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_a$—, —C($R_a$)($R_b$)—N(R)—O— or —C($R_aR_b$)—O—N(R)—. In certain embodiments, the bridge is 4'-$CH_2$-2', 4'—$(CH_2)_2$-2', 4'—$(CH_2)_3$-2', 4'—CH$_2$—O-2', 4'—(CH$_2$)$_2$—O-2', 4'—CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)2-O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

(A)
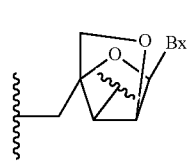

(B)
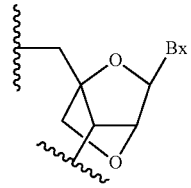

(C)
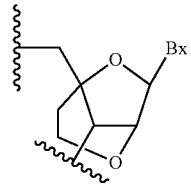

(D)
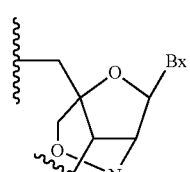

(E)
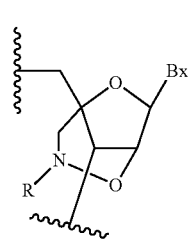

(F)
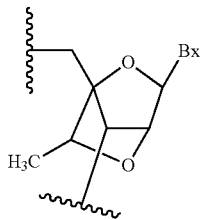

(G)
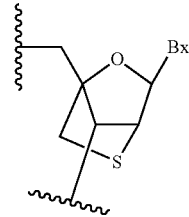

(H)
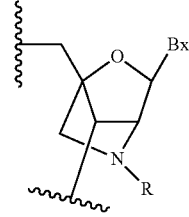

(I)
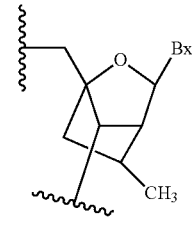

(J)
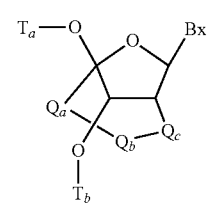

wherein Bx is the base moiety and R is independently H, a protecting group or C$_1$-C$_{12}$ alkyl.

In certain embodiments, bicyclic nucleosides are provided having Formula I:

I wherein:

Bx is a heterocyclic base moiety;

$-Q_a-Q_b-Q_c-$ is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;

R$_c$ is C$_1$-C$_{12}$ alkyl or an amino protecting group; and

T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

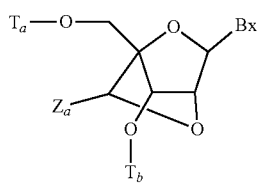

II wherein:

Bx is a heterocyclic base moiety;

T$_a$ and T$_b$ are each, independently H, a hydroxyl protecting group, a conjugate group, a reactive phosphorus group, a phosphorus moiety or a covalent attachment to a support medium;

Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each J$_c$, J$_d$ and J$_e$ is, independently, H, C$_1$-C$_6$ alkyl, or substituted C$_1$-C$_6$ alkyl and X is O or NJ$_c$.

In certain embodiments, bicyclic nucleosides are provided having Formula III:

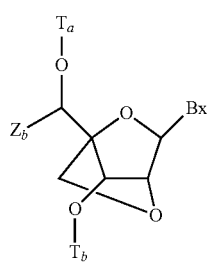

III wherein:

Bx is a heterocyclic base moiety;

T$_a$ and T$_b$ are each, independently H, a hydroxyl protecting group, a conjugate group, a reactive phosphorus group, a phosphorus moiety or a covalent attachment to a support medium;

Z$_b$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl or substituted acyl (C(=O)—).

In certain embodiments, bicyclic nucleosides are provided having Formula IV:

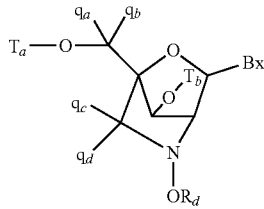

IV wherein:

Bx is a heterocyclic base moiety;

T$_a$ and T$_b$ are each, independently H, a hydroxyl protecting group, a conjugate group, a reactive phosphorus group, a phosphorus moiety or a covalent attachment to a support medium;

R$_d$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;

each q$_a$, q$_b$, q$_c$ and q$_d$ is, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl, C$_1$-C$_6$ alkoxyl, substituted C$_1$-C$_6$ alkoxyl, acyl, substituted acyl, C$_1$-C$_6$ aminoalkyl or substituted C$_1$-C$_6$ aminoalkyl;

In certain embodiments, bicyclic nucleosides are provided having Formula V:

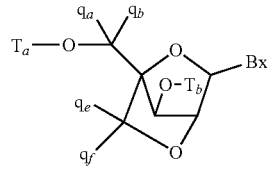

V wherein:

Bx is a heterocyclic base moiety;

T$_a$ and T$_b$ are each, independently H, a hydroxyl protecting group, a conjugate group, a reactive phosphorus group, a phosphorus moiety or a covalent attachment to a support medium;

q$_a$, q$_b$, q$_e$ and q$_f$ are each, independently, hydrogen, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxy, substituted C$_1$-C$_{12}$ alkoxy, OJ$_j$, SJ$_j$, SOJ$_j$, SO$_2$J$_j$, NJ$_j$J$_k$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$;

or q$_e$ and q$_f$ together are =C(q$_g$)(q$_h$);

q$_g$ and q$_h$ are each, independently, H, halogen, C$_1$-C$_{12}$ alkyl or substituted C$_1$-C$_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

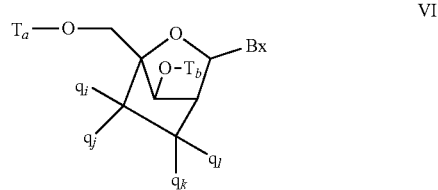

VI wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_i$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

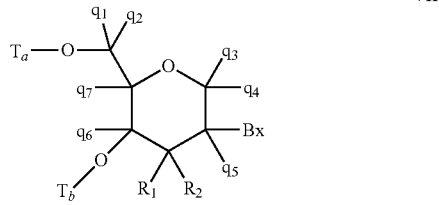

VII wherein independently for each of said at least one tetrahydropyran nucleoside analog of Formula VII:
Bx is a heterocyclic base moiety;
$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X) $NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif Compositions and Methods for Formulating Pharmaceutical Compositions Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an Ataxin 2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an Ataxin 2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5' terminus (5'-cap), or at the 3' terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Ataxin 2 nucleic acids can be tested in vitro in a variety of cell types. Cell types used for such analyses are available from commerical vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of inhibition of target levels or expression Inhibition of levels or expression of an Ataxin 2 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an Ataxin 2 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Ataxin 2 nucleic acids can be assessed by measuring Ataxin 2 protein levels. Protein levels of Ataxin 2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Ataxin 2 and produce phenotypic changes, such as, improved motor function and cognition. In certain embodiments, motor function is measured by walking initiation analysis, rotarod, grip strength, pole climb, open field performance, balance beam, hindpaw footprint testing in the animal.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in Ataxin 2 nucleic acid expression are measured.

Certain Indications

In certain embodiments, provided herein are methods, compounds, and compositions of treating an individual comprising administering one or more pharmaceutical compositions described herein. In certain embodiments, the individual has a neurodegenerative disease. In certain embodiments, the individual is at risk for developing a neurodegenerative disease, including, but not limited to, spinocerebellar ataxia type 2 (SCA2), amyotrophic lateral sclerosis (ALS), and parkinsonism. In certain embodiments, the individual has been identified as having an Ataxin 2 associated disease. In certain embodiments, provided herein are methods for prophylactically reducing Ataxin 2 expression in an individual. Certain embodiments include treating an individual in need thereof by administering to an individual a therapeutically effective amount of an antisense compound targeted to an Ataxin 2 nucleic acid.

In one embodiment, administration of a therapeutically effective amount of an antisense compound targeted to an Ataxin 2 nucleic acid is accompanied by monitoring of Ataxin 2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to an Ataxin 2 nucleic acid results in reduction of Ataxin 2 expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to an Ataxin 2 nucleic acid results in improved motor function in an animal. In certain embodiments, administration of an Ataxin 2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to Ataxin 2 are used for the preparation of a medicament for treating a patient suffering or susceptible to a neurodegenerative disease including spinocerebellar ataxia type 2 (SCA2), amyotrophic lateral sclerosis (ALS), and parkinsonism.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Ataxin 2 in HepG2 Cells by MOE Gapmers

Antisense oligonucleotides were designed targeting an ataxin 2 nucleic acid and were tested for their effects on ataxin 2 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and ataxin 2 mRNA levels were measured by quantitative real-time PCR. Human primer probe set RTS3642 (forward sequence ACCAAAGAGTAGTTAATGGAGGTGTTC, designated herein as SEQ ID NO: 5; reverse sequence AGAAGGTGGGCGAGAGGAA, designated herein as SEQ ID NO: 6; probe sequence CTGGCCATCGCCTTGCCCA, designated herein as SEQ ID NO: 7) was used to measure mRNA levels. Ataxin 2 mRNA levels were adjusted according to total RNA content, as measured by RIBOGREEN®. Results are presented as percent inhibition of ataxin 2, relative to untreated control cells.

The chimeric antisense oligonucleotides in the Tables below were designed as 5-10-5 MOE gapmers. The gapmers are 20 nucleosides in length, wherein the central gap segment is comprised of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human ataxin 2 mRNA, designated herein as SEQ ID NO: 1 (GENBANK Accession No. NM_002973.3) or the human ataxin 2 genomic sequence, designated herein as SEQ ID NO: 2 (the complement of GENBANK Accession No. NT_009775.17 truncated from nucleotides 2465000 to 2616000). Some oligonucleotides do not target either SEQ ID NO: 1 or SEQ ID NO: 2, but instead target a variant gene sequence, SEQ ID NO: 3 (GENBANK Accession No. BX410018.2). 'n/a' indicates that the antisense oligonucleotide does not target that particular gene sequence with 100% complementarity.

TABLE 1

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564118 | 606 | 625 | CCGGCTCGCACGCCGGGCGG | 57 | 2596 | 2615 | 11 |
| 564119 | 612 | 631 | CATACACCGGCTCGCACGCC | 63 | 2602 | 2621 | 12 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564120 | 637 | 656 | GGCTTCAGCGACATGGTGAG | 78 | 2627 | 2646 | 13 |
| 564121 | 880 | 899 | CGACCTCTGCCCAGGCCGGG | 67 | n/a | n/a | 14 |
| 564122 | 935 | 954 | TGCATAGATTCCATCAAAAG | 90 | 47454 | 47473 | 15 |
| 564123 | 959 | 978 | AAGTATATGAACCATCCTCA | 67 | 47478 | 47497 | 16 |
| 564124 | 997 | 1016 | TTCACTTGTACTTCACATTT | 85 | 48696 | 48715 | 17 |
| 564125 | 1084 | 1103 | TCTGTACTTTTCTCATGTGC | 88 | 49258 | 49277 | 18 |
| 564126 | 1090 | 1109 | CTGGATTCTGTACTTTTCTC | 89 | 49264 | 49283 | 19 |
| 564127 | 1123 | 1142 | CTCTCCATTATTTCTTCACG | 92 | 49297 | 49316 | 20 |
| 564128 | 1168 | 1187 | TCTTTAAACTGTACCACAAC | 86 | 49342 | 49361 | 21 |
| 564129 | 1210 | 1229 | GAGTCAGTAAAAGCATCTCT | 84 | n/a | n/a | 22 |
| 564130 | 1264 | 1283 | CAGGGCTCCAGGTCCTTCTC | 83 | 76401 | 76420 | 23 |
| 564131 | 1270 | 1289 | GCATCCCAGGGCTCCAGGTC | 86 | 76407 | 76426 | 24 |
| 564132 | 1363 | 1382 | TCTTCATTATATCGAAACAT | 84 | 80718 | 80737 | 25 |
| 564133 | 1477 | 1496 | GCTAACTGGTTTGCCCTTGC | 98 | 81637 | 81656 | 26 |
| 564134 | 1556 | 1575 | GTATTTTCTTCCTCACTCC | 82 | 81716 | 81735 | 27 |
| 564135 | 1562 | 1581 | TGCTGTGTATTTTCTTCCT | 89 | 81722 | 81741 | 28 |
| 564136 | 1748 | 1767 | GAAATCTGAAGTGTGAGAAG | 61 | 83359 | 83378 | 29 |
| 564137 | 1789 | 1808 | CCTCCATTAACTACTCTTTG | 90 | 83400 | 83419 | 30 |
| 564138 | 1795 | 1814 | GGAACACCTCCATTAACTAC | 66 | n/a | n/a | 31 |
| 564139 | 1807 | 1826 | GGCGATGGCCAGGGAACACC | 95 | 85303 | 85322 | 32 |
| 564140 | 1844 | 1863 | GTAGCGAGAAGGTGGGCGAG | 88 | 85340 | 85359 | 33 |
| 564141 | 1862 | 1881 | AGAGTTGGGACCTGACTGGT | 84 | 85358 | 85377 | 34 |
| 564142 | 1868 | 1887 | TGGAAGAGAGTTGGGACCTG | 84 | 85364 | 85383 | 35 |
| 564143 | 1963 | 1982 | GGAGCTGGAGAACCATGAGC | 91 | 85459 | 85478 | 36 |
| 564144 | 1969 | 1988 | GAGACAGGAGCTGGAGAACC | 86 | 85465 | 85484 | 37 |
| 564145 | 2101 | 2120 | TTGTGGGATACAAATTCTAG | 56 | 88211 | 88230 | 38 |
| 564146 | 2185 | 2204 | GGAACCCCACTGACCACTGA | 70 | n/a | n/a | 39 |
| 564147 | 2401 | 2420 | TCTTGAAGCCTGGAATCTTT | 61 | 91671 | 91690 | 40 |
| 564148 | 2560 | 2579 | AACCTAAAATCATTCTTAAA | 21 | n/a | n/a | 41 |
| 564149 | 2596 | 2615 | AGTTGATCCATAGATTCAGA | 74 | 112905 | 112924 | 42 |
| 564150 | 2704 | 2723 | CTGGTACAGTTGCTGCTGCT | 91 | 113013 | 113032 | 43 |
| 564151 | 2710 | 2729 | CTGCCACTGGTACAGTTGCT | 85 | 113019 | 113038 | 44 |
| 564152 | 2899 | 2918 | TTTGCATTGGGATTCAATGT | 76 | 114859 | 114878 | 45 |
| 564153 | 2938 | 2957 | GAAGGCTTTGGCTGAGAGAA | 66 | n/a | n/a | 46 |
| 564154 | 2944 | 2963 | GTAGTAGAAGGCTTTGGCTG | 71 | n/a | n/a | 47 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564155 | 2995 | 3014 | TGACCCACCATAGATGGGCT | 38 | 115850 | 115869 | 48 |
| 564156 | 3097 | 3116 | GGTATTGGGTATAAAGGTTG | 57 | n/a | n/a | 49 |
| 564157 | 3103 | 3122 | GTCATAGGTATTGGGTATAA | 76 | 116339 | 116358 | 50 |
| 564158 | 3331 | 3350 | GGATGCTGAGACTGATAATG | 54 | n/a | n/a | 51 |
| 564159 | 3337 | 3356 | ACATGAGGATGCTGAGACTG | 63 | n/a | n/a | 52 |
| 564160 | 3472 | 3491 | AATTTGGGACATGCATACAT | 23 | n/a | n/a | 53 |
| 564161 | 3490 | 3509 | GTCTCCTTGTTGTATGGTAA | 76 | 136963 | 136982 | 54 |
| 564162 | 3658 | 3677 | TGAACAGGACTGGGTGCAGG | 41 | 144433 | 144452 | 55 |
| 564163 | 3715 | 3734 | GACTGCTGCTGTGGACTGGC | 69 | 145447 | 145466 | 56 |
| 564164 | 3903 | 3922 | CTGACTGTACATGAGCCTGA | 50 | 147818 | 147837 | 57 |
| 564165 | 3909 | 3928 | CCATTCCTGACTGTACATGA | 69 | 147824 | 147843 | 58 |
| 564166 | 3927 | 3946 | CAGTTGGATGAGAAGGAACC | 58 | 147842 | 147861 | 59 |
| 564167 | 3933 | 3952 | CATGGGCAGTTGGATGAGAA | 29 | 147848 | 147867 | 60 |
| 564168 | 3971 | 3990 | ACCGCCGGGTGGCTGTGTCG | 40 | 147886 | 147905 | 61 |
| 564169 | 3993 | 4012 | TTTGAGCGAGGGCGGCCTGG | 19 | 147908 | 147927 | 62 |
| 564170 | 4005 | 4024 | GCTGTAGTGCACTTTGAGCG | 73 | 147920 | 147939 | 63 |
| 564171 | 4017 | 4036 | AGACTGGAATGGGCTGTAGT | 58 | 147932 | 147951 | 64 |
| 564172 | 4029 | 4048 | GCGCTGTTGTCGAGACTGGA | 74 | 147944 | 147963 | 65 |
| 564173 | 4035 | 4054 | GGAAATGCGCTGTTGTCGAG | 69 | 147950 | 147969 | 66 |
| 564174 | 4064 | 4083 | GGCTTGTACTGAAGGGTGCG | 23 | n/a | n/a | 67 |
| 564175 | 4070 | 4089 | GTGGTGGGCTTGTACTGAAG | 35 | n/a | n/a | 68 |
| 564176 | 4076 | 4095 | CTGTTGGTGGTGGGCTTGTA | 22 | 148827 | 148846 | 69 |
| 564177 | 4082 | 4101 | CAACTGCTGTTGGTGGTGGG | 39 | 148833 | 148852 | 70 |
| 564178 | 4088 | 4107 | GCCTTACAACTGCTGTTGGT | 62 | 148839 | 148858 | 71 |
| 564179 | 4106 | 4125 | TTCGGTTCCTCCAGGGCAGC | 72 | 148857 | 148876 | 72 |
| 564180 | 4166 | 4185 | TTCTAGTTTTCTGTGCTTCC | 72 | 148917 | 148936 | 73 |
| 564181 | 4367 | 4386 | AATAAATAACTTCCAGTTTC | 59 | 149118 | 149137 | 74 |
| 564182 | 4429 | 4448 | GAATCACTCTTGTTACTTCT | 78 | 149180 | 149199 | 75 |
| 564183 | 4435 | 4454 | CAGCAAGAATCACTCTTGTT | 85 | 149186 | 149205 | 76 |
| 564184 | 4551 | 4570 | TTTATAAATAATAATCCGTC | 4 | 149302 | 149321 | 77 |
| 564185 | 4593 | 4612 | AAGTTGAACCACTGTAGACA | 60 | 149344 | 149363 | 78 |
| 564186 | n/a | n/a | ATCGGCCACCACCCGCGCGC | 55 | 3683 | 3702 | 79 |
| 564187 | n/a | n/a | CAAAGGGTTAATTAGGATCT | 66 | 85057 | 85076 | 80 |
| 564188 | n/a | n/a | CCCAAAGGGTTAATTAGGAT | 94 | 85059 | 85078 | 81 |
| 564189 | n/a | n/a | AGGACAGTCATTTGATTTGT | 72 | 85166 | 85185 | 82 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564190 | n/a | n/a | CTTTGAGGACAGTCATTTGA | 70 | 85171 | 85190 | 83 |
| 564191 | n/a | n/a | CTGACAGAACAAATGATATG | 17 | 85284 | 85303 | 84 |
| 564192 | n/a | n/a | TATTGGGTATAAAGGCTTGA | 31 | 116331 | 116350 | 85 |
| 564193 | n/a | n/a | GGTATTGGGTATAAAGGCTT | 78 | 116333 | 116352 | 86 |
| 564194 | n/a | n/a | CTCTTTTACGCATACAGGCA | 74 | 147789 | 147808 | 87 |
| 564195 | n/a | n/a | AGGAAGGCCAACTGAGTCCT | 70 | 148258 | 148277 | 88 |

TABLE 2

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564158 | 3331 | 3350 | GGATGCTGAGACTGATAATG | 61 | n/a | n/a | 51 |
| 564196 | 70 | 89 | GGTCAGACGGAAGCAGAACG | 9 | 2060 | 2079 | 89 |
| 564197 | 218 | 237 | CCACCTGGCTGCGGCGAAGC | 12 | 2208 | 2227 | 90 |
| 564198 | 392 | 411 | GCCGTTGCCGTTGCTACCAA | 80 | 2382 | 2401 | 91 |
| 564199 | 616 | 635 | GGCCCATACACCGGCTCGCA | 79 | 2606 | 2625 | 92 |
| 564200 | 636 | 655 | GCTTCAGCGACATGGTGAGG | 81 | 2626 | 2645 | 93 |
| 564201 | 732 | 751 | GGACATTGGCAGCCGCGGGC | 83 | 2722 | 2741 | 94 |
| 564202 | 929 | 948 | GATTCCATCAAAAGAAATCG | 67 | n/a | n/a | 95 |
| 564203 | 969 | 988 | CAACTGATGTAAGTATATGA | 45 | 47488 | 47507 | 96 |
| 564204 | 1053 | 1072 | CCAAATCACACTTCGGACTG | 74 | n/a | n/a | 97 |
| 564205 | 1073 | 1092 | CTCATGTGCGGCATCAAGTA | 79 | 49247 | 49266 | 98 |
| 564206 | 1138 | 1157 | CATTTGAACAAAATACTCTC | 71 | 49312 | 49331 | 99 |
| 564207 | 1219 | 1238 | CTGATAGCAGAGTCAGTAAA | 72 | 76356 | 76375 | 100 |
| 564208 | 1521 | 1540 | GGGCCACTCGAGCTTTGTAC | 88 | 81681 | 81700 | 101 |
| 564209 | 1628 | 1647 | AGGAATATATTTATTTTCCC | 52 | 83239 | 83258 | 102 |
| 564210 | 1693 | 1712 | CCCATACGCGGTGAATTCTG | 91 | 83304 | 83323 | 103 |
| 564211 | 1713 | 1732 | TGGAGCCCGATCCAGGCTGG | 77 | 83324 | 83343 | 104 |
| 564212 | 1733 | 1752 | AGAAGTGGATCTTGATGGCA | 54 | 83344 | 83363 | 105 |
| 564213 | 1957 | 1976 | GGAGAACCATGAGCAGAGGG | 83 | 85453 | 85472 | 106 |
| 564214 | 2002 | 2021 | GGCCCTTCTGAAGACATGCG | 85 | n/a | n/a | 107 |
| 564215 | 2079 | 2098 | CACTGGATATGGAACCCCTC | 84 | 88189 | 88208 | 108 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564216 | 2099 | 2118 | GTGGGATACAAATTCTAGGC | 94 | 88209 | 88228 | 109 |
| 564217 | 2177 | 2196 | ACTGACCACTGATGACCACG | 67 | 88287 | 88306 | 110 |
| 564218 | 2215 | 2234 | CTGGGTCTATGAGTTTTAGG | 67 | 91099 | 91118 | 111 |
| 564219 | 2291 | 2310 | TGGAATAATACCAGCTTGGG | 84 | 91175 | 91194 | 112 |
| 564220 | 2311 | 2330 | GGCATGGCAACAGCTTCAGT | 81 | 91195 | 91214 | 113 |
| 564221 | 2331 | 2350 | TAGGAGATGCAGCTGGAATA | 71 | 91215 | 91234 | 114 |
| 564222 | 2397 | 2416 | GAAGCCTGGAATCTTTAGCC | 69 | n/a | n/a | 115 |
| 564223 | 2426 | 2445 | CCCTGCAGGAGAGTTCTGCC | 75 | 91696 | 91715 | 116 |
| 564224 | 2582 | 2601 | TTCAGAAGTAGAACTTGGCT | 76 | 112891 | 112910 | 117 |
| 564225 | 2652 | 2671 | CAATTTTGTCTTTGATCAAA | 56 | 112961 | 112980 | 118 |
| 564226 | 2757 | 2776 | TGTTACTAAGTATTGAAGGG | 53 | 113066 | 113085 | 119 |
| 564227 | 2787 | 2806 | AAGTGACCTCAGGTCCCCTC | 83 | 113096 | 113115 | 120 |
| 564228 | 2883 | 2902 | ATGTTGATTTCCTAACTTGC | 53 | 114843 | 114862 | 121 |
| 564229 | 3019 | 3038 | GTATAAACTGGAGTTGGCTG | 75 | 115874 | 115893 | 122 |
| 564230 | 3039 | 3058 | GTGCAAAACAAACAGGCTGA | 79 | 115894 | 115913 | 123 |
| 564231 | 3059 | 3078 | GACTGGATACATCATATTTG | 18 | 115914 | 115933 | 124 |
| 564232 | 3082 | 3101 | GGTTGCACGCCTGGGCTCAC | 74 | n/a | n/a | 125 |
| 564233 | 3102 | 3121 | TCATAGGTATTGGGTATAAA | 50 | 116338 | 116357 | 126 |
| 564234 | 3122 | 3141 | TTGATTCACTGGCATGGGCG | 77 | 116358 | 116377 | 127 |
| 564235 | 3180 | 3199 | GATGATGCTGGTCTTGCCGC | 49 | 130944 | 130963 | 128 |
| 564236 | 3373 | 3392 | ATCATTCTAGCATTACCCTG | 61 | 131454 | 131473 | 129 |
| 564237 | 3408 | 3427 | ATACTAAACCAGGCTGGGCG | 71 | 131489 | 131508 | 130 |
| 564238 | 3464 | 3483 | ACATGCATACATCGCATGCG | 32 | n/a | n/a | 131 |
| 564239 | 3505 | 3524 | TAGAAAGAAGGGCTTGTCTC | 67 | 136978 | 136997 | 132 |
| 564240 | 3545 | 3564 | CGCATACTGCTGAGCAAGGG | 79 | 144320 | 144339 | 133 |
| 564241 | 3597 | 3616 | TAGCTGAAGGCTGAGGGTGT | 43 | 144372 | 144391 | 134 |
| 564242 | 3630 | 3649 | CACCATGTTGGCTTTGCTGC | 81 | 144405 | 144424 | 135 |
| 564243 | 3650 | 3669 | ACTGGGTGCAGGATGACTTC | 36 | 144425 | 144444 | 136 |
| 564244 | 3729 | 3748 | CGTGGTAAATGGCTGACTGC | 50 | 145461 | 145480 | 137 |
| 564245 | 3772 | 3791 | TTGGAGGCAGGTGTCATGGA | 36 | 145504 | 145523 | 138 |
| 564246 | 3938 | 3957 | TGGCGCATGGGCAGTTGGAT | 67 | 147853 | 147872 | 139 |
| 564247 | 3994 | 4013 | CTTTGAGCGAGGGCGGCCTG | 29 | 147909 | 147928 | 140 |
| 564248 | 4021 | 4040 | GTCGAGACTGGAATGGGCTG | 54 | 147936 | 147955 | 141 |
| 564249 | 4225 | 4244 | ATTCCTATTGGATGTTACAA | 65 | 148976 | 148995 | 142 |
| 564250 | 4252 | 4271 | ATCTTCCACTGCAAGTGAAC | 77 | 149003 | 149022 | 143 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564251 | 4306 | 4325 | TATGGAATTATGGAATAGCC | 65 | 149057 | 149076 | 144 |
| 564252 | 4433 | 4452 | GCAAGAATCACTCTTGTTAC | 77 | 149184 | 149203 | 145 |
| 564253 | 4581 | 4600 | TGTAGACAGTGATCACCTCA | 77 | 149332 | 149351 | 146 |
| 564254 | n/a | n/a | GGCCAAGGCCCACTTGTCTC | 54 | 3485 | 3504 | 147 |
| 564255 | n/a | n/a | CACTGCGGCCTCGAACAGCA | 81 | 3709 | 3728 | 148 |
| 564263 | n/a | n/a | AAATTCCTCATTTTCTTTTC | 68 | 26924 27239 | 26943 27258 | 149 |
| 564264 | n/a | n/a | GTTATAGTAATCTGTAATCA | 71 | 36133 36239 | 36152 36258 | 150 |
| 564265 | n/a | n/a | AGGATTGTAAAATGATACAG | 47 | 65107 65148 | 65126 65167 | 151 |
| 564266 | n/a | n/a | GTAGGATTGTAAAATGATAC | 64 | 65109 65150 | 65128 65169 | 152 |
| 564267 | n/a | n/a | TTATATATGTAAATTATATC | 9 | 95228 95288 | 95247 95307 | 153 |
| 564268 | n/a | n/a | AACCACTGATTTATACACTT | 88 | 95260 95320 | 95279 95339 | 154 |
| 564269 | n/a | n/a | TTAAAAACCACTGATTTATA | 17 | 95265 95325 | 95284 95344 | 155 |
| 564270 | n/a | n/a | ATATAGCACTCTGCTGTATT | 83 | 99282 99340 | 99301 99359 | 156 |
| 564271 | n/a | n/a | TACCAAGCTTGTGGCTTGGG | 32 | 137342 137420 | 137361 137439 | 157 |
| 564272 | n/a | n/a | TTATACCAAGCTTGTGGCTT | 52 | 137345 137423 | 137364 137442 | 158 |

TABLE 3

Inhibition of ataxin 2 mRNA by 5-10-5 MOE gapmers targeting SEQ ID NO: 3

| ISIS No | SEQ ID NO: 3 Start Site | SEQ ID NO: 3 Stop Site | Sequence | % inhibition | SEQ ID NO |
|---|---|---|---|---|---|
| 564256 | 311 | 330 | CCTCGATGTTCCACAGGCGC | 83 | 159 |
| 564257 | 715 | 734 | GAGTTCACCTGCATCCAGGG | 81 | 160 |
| 564258 | 736 | 755 | TCCAGTTCCCTCATTGGCTG | 27 | 161 |
| 564259 | 771 | 790 | GGTTCCATCCATTAGATACG | 52 | 162 |
| 564260 | 791 | 810 | TTAAACGAAACATATCTTTG | 10 | 163 |
| 564261 | 815 | 834 | GCCCCTGCGCCATAATTTTT | 3 | 164 |
| 564262 | 835 | 854 | ATAAACTGCTTTCAACGGTG | 2 | 165 |

Example 2: Dose-Dependent Antisense Inhibition of Human Ataxin 2 in HepG2 Cells by MOE Gapmers Gapmers from Example 1 exhibiting significant in vitro inhibition of ataxin 2 mRNA were selected and tested at various doses in HepG2 cells. Cells were plated at a density of 20,000 cells per well and transfected using electroporation with 0.625 μM, 1.250 μM, 2.500 μM, 5.000 μM and 10.000 μM concentrations of antisense oligonucleotide, as specified in the Table below. After a treatment period of approximately 16 hours, RNA was isolated from the cells and ataxin 2 mRNA levels were measured by quantitative real-time PCR. Human primer probe set RTS3642 was used to measure mRNA levels. Ataxin 2 mRNA levels were adjusted according to total RNA content, as measured by RIBOGREEN®. Results are presented as percent inhibition of ataxin 2, relative to untreated control cells.

The half maximal inhibitory concentration ($IC_{50}$) of each oligonucleotide is also presented. Ataxin 2 mRNA levels were significantly reduced in a dose-dependent manner in antisense oligonucleotide treated cells.

TABLE 4

Dose response assay

| ISIS No | 0.625 µM | 1.250 µM | 2.500 µM | 5.000 µM | 10.000 µM | IC$_{50}$ (µM) |
|---|---|---|---|---|---|---|
| 564133 | 89 | 95 | 98 | 98 | 97 | <0.6 |
| 564188 | 52 | 72 | 81 | 88 | 90 | <0.6 |
| 564127 | 42 | 62 | 65 | 85 | 91 | 0.8 |
| 564150 | 39 | 63 | 74 | 86 | 91 | 0.8 |
| 564143 | 37 | 60 | 76 | 84 | 94 | 0.9 |
| 564122 | 25 | 53 | 69 | 85 | 88 | 1.3 |
| 564126 | 23 | 48 | 61 | 78 | 89 | 1.7 |
| 564144 | 12 | 35 | 53 | 71 | 85 | 2.4 |
| 564135 | 22 | 35 | 53 | 73 | 86 | 2.1 |
| 564125 | 33 | 44 | 64 | 78 | 85 | 1.5 |
| 564129 | 31 | 42 | 54 | 71 | 77 | 1.9 |
| 564216 | 50 | 67 | 82 | 86 | 94 | <0.6 |
| 564210 | 33 | 48 | 72 | 80 | 94 | 1.3 |
| 564208 | 30 | 40 | 67 | 75 | 87 | 1.6 |
| 564268 | 35 | 52 | 69 | 81 | 85 | 1.2 |

Example 3: Antisense Inhibition of Human Ataxin 2 in a SCA2 BAC Mouse Model

Gapmers from Example 1 exhibiting significant in vitro inhibition of ataxin 2 mRNA were selected and tested in vivo in a SCA2[Q22]-BAC mouse model. This mouse model was created in the Pulst laboratory (University of Utah, Salt Lake City), using mice of FVB/B6 hybrid background, for the study of spinocerebella ataxia type 2 (SCA2). These mice possess the entire 176 kb human ATXN2 gene region, including the 16 kb upstream sequence and the 2.5 kb downstream sequence.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 µL mark with either normal saline (0.9%) or antisense oligonucleotide (250 µg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 µL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 µL, consisting of 15 ng cDNA, 2 µL of each primer (0.3 µM final), and 10 µL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis.

The results from the RNA analysis for mouse and human ataxin 2 are presented in the Table below. As indicated, some of the ISIS oligonucleotides decreased human ataxin 2 mRNA in the brains of the mice.

TABLE 5

Percent inhibition of ataxin 2 mRNA compared to the saline (0.9%) control in SCA[Q22]-BAC mice

| ISIS No | Human ataxin 2 | Mouse ataxin 2 |
|---|---|---|
| 564122 | 10 | 15 |
| 564127 | 46 | 65 |
| 564133 | 60 | 62 |
| 564150 | 21 | 53 |
| 564188 | 9 | 23 |
| 564216 | 21 | 55 |

Example 4: Antisense Inhibition of Human Ataxin 2 in an ATXN2-Q127 Mouse Model Gapmers from Example 1 exhibiting significant in vitro inhibition of ataxin 2 mRNA were selected and tested in vivo in an ATXN2-Q127 mouse model. This mouse model (Hansen, S. T. et al., Human. Molecular Genetics 2012. 1-13) expresses the full-length-mutant ATXN2$^{Q127}$ complementary DNA under the regulation of the Purkinje cell protein-2 (Pcp2) promoter. This model shows an early-onset progressive motor impairment phenotype accompanied by the formation of diffuse cytoplasmic aggregates in cerebellar Purkinje cells.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 µL mark with either normal saline (0.9%) or antisense oligonucleotide (250 µg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 µL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 µL, consisting of 15 ng cDNA, 2 of each primer (0.3 µM final), and 10 µL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis. All mRNA levels were normalized to the housekeeping gene, actin.

The results from the RNA analysis for mouse and human ataxin 2 are presented in the Table below. As indicated, some of the ISIS oligonucleotides decreased human ataxin 2 mRNA in the brains of the mice.

qPCR analysis of the marker for microgliosis, AIF/Ibal, to measure inflammation, was also performed. The results are presented in the Table below.

TABLE 6

Percent inhibition of ataxin 2 mRNA compared to the saline (0.9%) control in ATXN2-Q127 mice

| ISIS No | Human | Mouse |
|---|---|---|
| 564133 | 64 | 52 |
| 564127 | 62 | 49 |
| 564216 | 46 | 40 |
| 564210 | 39 | 48 |

TABLE 7

Percent Ibal mRNA level increase compared to the saline (0.9%) control in ATXN2-Q127 mice

| ISIS No | Ibal |
|---|---|
| 564133 | 9 |
| 564127 | 49 |
| 564216 | 16 |
| 564210 | 96 |

Example 4: Dose-Dependent Antisense Inhibition of Human Ataxin 2 in an ATXN2-Q127 Mouse Model ISIS 564133 was tested in different doses in the ATXN2-Q127 mouse model.

Treatment

Groups of 3 mice each were administered normal saline (0.9%) or ISIS 564133 via intracerebroventricular injections dosed at 50 µg, 100 µg, 200 µg, 250 µg, or 300 µg. The mice were administered in the same manner as described in the studies above and monitored daily.

RNA Analysis

After 7 days, the mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for mouse and human ataxin 2 are presented in the Table below.

TABLE 8

Percent inhibition of ataxin 2 mRNA compared to the saline (0.9%) control in ATXN2-Q127 mice

| Dose (µg) | Human ataxin 2 | Mouse ataxin 2 |
|---|---|---|
| 50 | 60 | 47 |
| 100 | 84 | 35 |
| 200 | 85 | 67 |
| 250 | 79 | 62 |
| 300 | 73 | 41 |

Example 5: Time-Dependent Antisense Inhibition of Human Ataxin 2 in an ATXN2-Q127 Mouse Model ISIS 564133 was administered and mRNA level reduction was tested in different time points in the ATXN2-Q127 mouse model.

Treatment

Groups of 3 mice each were administered normal saline (0.9%) or ISIS 564133 via intracerebroventricular injections dosed at 200 µg. The mice were administered in the same manner as described in the studies above and monitored daily.

RNA Analysis

After 9 days, 18 days, 27 days, and 84 days, groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for human ataxin 2 are presented in the Table below. Western analysis of the corresponding protein samples was performed and confirmed the qPCR results.

TABLE 9

Ataxin 2 mRNA levels in ATXN2-Q127 mice

| Time Point | ATXN2 expression relative to actin |
|---|---|
| saline (0.9%) control | 8.4 |
| 9 days | 2.9 |
| 18 days | 0.9 |
| 27 days | 1.4 |
| 84 days | 2.7 |

Immunohistochemical staining of cerebellar Purkinje cells on day 7 was performed using rabbit anti-oligonucleotide antibody generated in-house. The results demonstrated that ISIS oligonucleotide localized in cerebellar Purkinje cells of ATXN-Q127 mice.

Example 6: Effect of Antisense Inhibition of Human Ataxin 2 in an ATXN2-Q127 Mouse Model ISIS oligonucleotide was administered in the ATXN2-Q127 mouse model and wild-type mice. On day 3, motor performance was evaluated using the rotarod test.

Groups of ATXN2-Q127 mice were administered normal saline (0.9%) or ISIS 564133 at 50 µg, 100 µg, or 200 µg via intracerebroventricular injections in the same manner as described in the studies above. Groups of wild-type mice were administered normal saline (0.9%) or ISIS oligonucleotide at 200 µg via intracerebroventricular injections dosed in the same manner as described in the studies above. Groups of ATXN2-Q127 mice were administered normal saline (0.9%) or ISIS 546127 or ISIS 564216 at 200 µg via intracerebroventricular injections dosed in the same manner as described in the studies above. After 6 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20%.

TABLE 10

Rotarod performance test in ATXN2-Q127 mice

| Strain of mice | Number of mice | Treatment | Latency to fall (seconds) |
|---|---|---|---|
| WT | 10 | saline (0.9%) control | 199 |
|  | 10 | ISIS 564133 (200 µg) | 189 |
| ATXN-Q127 | 8 | saline (0.9%) control | 127 |
|  | 15 | ISIS 564133 (50 µg) | 149 |
|  | 16 | ISIS 564133 (100 µg) | 141 |
|  | 9 | ISIS 564133 (200 µg) | 100 |
| ATXN-Q127 | 15 | saline (0.9%) control | 130 |
|  | 13 | ISIS 564127 (200 µg) | 150 |
|  | 15 | ISIS 564216 (200 µg) | 156 |

Example 7: Effect of Antisense Inhibition of Human Ataxin 2 in an ATXN2-Q127 Mouse Model ISIS oligonucleotide was administered in the ATXN2-Q127 mouse model and wild-type mice. Cerebellar expression of ataxin 2, as well as several Purkinje cell (PC) genes, was assessed.

Groups of ATXN2-Q127 mice were administered normal saline (0.9%) or ISIS 564133 at 200 µg via intracerebroventricular injections dosed in the same manner as described in the studies above. Groups of wild-type mice were administered normal saline (0.9%) or ISIS 564133 at 200 µg via intracerebroventricular injections dosed in the same manner as described in the studies above. After 5 weeks, the mice were euthanized and cerebellar expression of various gene mRNA levels was assessed.

RNA Analysis

Groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin. RNA levels of human ataxin 2, murine ataxin 2, Pcp2, Calb1, Rgs8, and Fam107b were measured. Transcription changes in several of these PC-specific genes have been demonstrated to progressively decrease in models of SCA2 (Hansen, S. T. et al., Hum. Mol. Genet. 2013. 22: 271-283).

The results from the RNA analysis are presented in the Table below and demonstrate that treatment with ISIS oligonucleotides targeting ataxin 2 increased the expression levels of all the PC-specific genes compared to the transgenic control group.

TABLE 11

PC-specific mRNA levels in ATXN2-Q127 mice

|  | WT | ATXN-Q127 | |
|---|---|---|---|
|  | saline (0.9%) control | saline (0.9%) control | ISIS 564133 (200 µg) |
| human ataxin 2 | 0.21 | 3.57 | 1.31 |
| murine ataxin 2 | 0.79 | 0.84 | 0.6 |
| Pcp2 | 0.77 | 0.36 | 0.48 |
| Rgs8 | 1.45 | 0.25 | 0.35 |
| Calb1 | 1.14 | 0.5 | 0.71 |
| Fam107b | 1.41 | 0.7 | 0.9 |

Example 8: Effect of Antisense Inhibition of Human Ataxin 2 in an ATXN2-Q127 Mouse Model ISIS oligonucleotide was administered in the ATXN2-Q127 mouse model and wild-type mice. Motor performance was evaluated using the rotarod test.

Groups of ATXN2-Q127 mice (7.5 weeks of age) were administered normal saline (0.9%) or ISIS 546127 or ISIS 564216 at 200 µg via intracerebroventricular injections dosed in the same manner as described in the studies above. After 5 weeks and 9 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20% on week 5 and about 27% on week 9.

TABLE 12

Rotarod performance test in ATXN2-Q127 mice.
(mean latency to fall, in seconds)

| Weeks after injection | | ISIS 564127 | ISIS 564216 | Saline control |
|---|---|---|---|---|
| Week 5 | DAY 3 | 137 | 145 | 123 |
| | DAY 4 | 140 | 141 | 119 |
| | DAY 5 | 155 | 154 | 131 |
| Week 9 | DAY 3 | 131 | 149 | 104 |
| | DAY 4 | 125 | 139 | 104 |
| | DAY 5 | 134 | 139 | 112 |

Example 9: Effect of Antisense Inhibition of Human Ataxin 2 in an ATXN2-Q127 Mouse Model ISIS oligonucleotide was administered in the ATXN2-Q127 mouse model. Motor performance was evaluated using the rotarod test.

Seven week old ATXN2-Q127 mice were subjected to the rotarod test, then divided into two groups of 30 mice each, such that average rotarod performance, average weights, and sex composition were equal across both groups. At 8 weeks of age, one group of mice received normal saline via intracerebroventricular (ICV) injection and one group received ISIS 564216 at 210 µg via ICV injection, dosed in the same manner as described in the studies above. Five weeks later (13 weeks of age), the mice were again subjected to the rotarod test. Six weeks post injection (14 weeks of age), the mice received a second ICV injection, identical to the injection received at 8 weeks of age. Five weeks later (19 weeks of age, 11 weeks after the first ICV injection), the mice were subjected to a third rotarod test.

Rotarod Test

The accelerating rotarod test was performed on the Rotamex rotarod. Rotarod testing was conducted over five days. On the first day, mice were acclimated to the technician by being handled by the technician three times, 5 minutes each time. On the second day, mice were introduced to the rotarod three times, 10 minutes each time at a speed ranging from 0 to 10 RPM. On each of days 3-5, mice were placed on the rotarod at a speed of 0 RPM, then the rotarod was accelerated to 40 RPM over 6 minutes, and this was done for each mouse three times. The three total trials per day were used to calculate a mean value of "latency to fall" per day, in seconds. Latency to fall is defined as the amount of time before the animal falls from the rotarod. It was recorded automatically, when the mouse no longer interrupted infrared beams directed above the rotarod. The time to first passive rotation (when mice stop walking and hold on and revolve with the rod) is also automatically recorded, and generally reflects the latency to fall time.

The results from the rotarod test are presented as the average for each treatment group in the Table below. As shown in the Table below, treatment with ASO improved rotarod performance.

TABLE 13

Rotarod performance test in ATXN2-Q127 mice

| Treatment | Weeks after 1st injection | Weeks after 2nd injection | Testing day | Latency to fall (s) |
|---|---|---|---|---|
| Saline | 5 | n/a | 3 | 218.5 |
| | | | 4 | 240.9 |
| | | | 5 | 236.5 |
| Isis No. 564216 | 5 | n/a | 3 | 240.6 |
| | | | 4 | 257.9 |
| | | | 5 | 259.6 |
| Saline | 11 | 5 | 3 | 216.2 |
| | | | 4 | 198.7 |
| | | | 5 | 212.1 |
| Isis No. 564216 | 11 | 5 | 3 | 194.4 |
| | | | 4 | 226.0 |
| | | | 5 | 242.8 |

What is claimed is:

1. An oligomeric compound comprising a modified oligonucleotide consisting of 14 to 30 linked nucleosides, wherein the nucleobase sequence of the modified oligonucleotide comprises a portion of at least 14 contiguous nucleobases, wherein the portion is complementary to: an equal length portion of nucleobases 1957-1988 of SEQ ID NO:1 wherein the modified oligonucleotide comprises at least one modification selected from a modified sugar moiety and a modified internucleoside linkage.

2. An oligomeric compound comprising a modified oligonucleotide consisting of 14 to 30 linked nucleosides and having a nucleobase sequence comprising at least 14 contiguous nucleobases of the nucleobase sequence of SEQ ID NO: 36 or 37, wherein the modified oligonucleotide comprises at least one modification selected from a modified sugar moiety and a modified internucleoside linkage.

3. The oligomeric compound of claim 1, wherein the modified oligonucleotide is at least 95% or is 100% complementary to an equal length portion of an Ataxin 2 RNA transcript.

4. The oligomeric compound of claim 3, wherein the Ataxin 2 RNA transcript has the nucleobase sequence of SEQ ID NO: 1, SEQ ID NO: 2, or SEQ ID NO: 3.

5. The oligomeric compound of claim 1, wherein the modified oligonucleotide consists of 14 to 20, 15 to 25, 15 to 30, 16 to 30, 17 to 30, 18 to 22, 18 to 30, 19 to 21, 19 to 30, or 20 to 30 linked nucleosides.

6. The oligomeric compound of claim 1, wherein the modified oligonucleotide consists of 20 linked nucleosides.

7. The oligomeric compound of claim 1, consisting of a single-stranded modified oligonucleotide.

8. The oligomeric compound of claim 1, wherein at least one internucleoside linkage of the modified oligonucleotide is a modified internucleoside linkage.

9. The oligomeric compound of claim 8, wherein at least one modified internucleoside linkage is a phosphorothioate internucleoside linkage.

10. The oligomeric compound of claim 9, wherein at least one internucleoside linkage is a phosphodiester internucleoside linkage.

11. The oligomeric compound of claim 9, wherein each modified internucleoside linkage is a phosphorothioate internucleoside linkage.

12. The oligomeric compound of claim 1, wherein at least one nucleoside of the modified oligonucleotide comprises a modified nucleobase.

13. The oligomeric compound of claim 12, wherein the modified nucleobase is a 5-methylcytosine.

14. The oligomeric compound of claim 1, wherein at least one nucleoside of the modified oligonucleotide comprises a modified sugar moiety.

15. The oligomeric compound of claim 14, wherein the at least one modified sugar moiety is a 2'-substituted sugar moiety.

16. The oligomeric compound of claim 14, wherein the at least one modified sugar moiety is a bicyclic sugar.

17. The oligomeric compound of claim 16, wherein the bicyclic sugar comprises a 4'-CH(R)—O-2' bridge wherein R is, independently, H, $C_1$-$C_{12}$ alkyl, or a protecting group.

18. The oligomeric compound of claim 17, wherein R is methyl.

19. The oligomeric compound of claim 17, wherein R is H.

20. The oligomeric compound of claim 15, wherein the at least one modified sugar moiety is a 2'-O-methoxyethyl sugar moiety or a 2'-O-methyl sugar moiety.

21. The oligomeric compound of claim 1, wherein the modified oligonucleotide comprises:
   a gap segment consisting of 10 linked deoxyribonucleosides;
   a 5' wing segment consisting of 5 linked nucleosides; and
   a 3' wing segment consisting of 5 linked nucleosides;
   wherein the gap segment is positioned between the 5' wing segment and the 3' wing segment and wherein each nucleoside of each wing segment comprises a modified sugar moiety.

22. A pharmaceutical composition comprising the oligomeric compound of claim 1, and a pharmaceutically acceptable carrier or diluent.

23. The oligomeric compound of claim 1, wherein the modified oligonucleotide is a sodium salt or a potassium salt.

24. The pharmaceutical composition of claim 22, wherein the pharmaceutically acceptable diluent is phosphate-buffered saline (PBS).

25. The pharmaceutical composition of claim 22, wherein the modified oligonucleotide of the oligomeric compound is a sodium salt or a potassium salt.

26. The oligomeric compound of claim 1, wherein at least one nucleoside comprises a modified nucleobase.

27. The oligomeric compound of claim 25, wherein the modified nucleobase is a 5-methylcytosine.

* * * * *

SEQUENCE LISTING

<160> NUMBER OF SEQ ID NOS: 165

<210> SEQ ID NO 1
<211> LENGTH: 4712
<212> TYPE: DNA
<213> ORGANISM: Homo sapiens

<400> SEQUENCE: 1 accccgaga   aagcaaccca   gcgcgccgcc   cgctcctcac   gtgtccctcc   cggccccggg    60

```
gccacctcac gttctgcttc cgtctgaccc ctccgacttc cggtaaagag tccctatccg    120
cacctccgct cccacccggc gcctcggcgc gcccgccctc cgatgcgctc agcggccgca    180
gctcctcgga gtcccgcggt ggccaccgag tctcgccgct tcgccgcagc caggtggccc    240
gggtggcgct cgctccagcg gccggcgcgg cggagcgggc ggggcggcgg tggcgcggcc    300
ccgggaccgt atccctccgc cgcccctccc ccgcccggcc ccggccccccc tccctcccgg    360 cagagctcgc ctccctccgc ctcagactgt tttggtagca acggcaacgg cggcggcgcg    420
tttcggcccg gctcccggcg gctccttggt ctcggcgggc ctccccgccc cttcgtcgtc    480
ctccttctcc ccctcgccag cccggggcgcc cctccggccg cgccaacccg cgcctccccg    540
ctcggcgccc gcgcgtcccc gccgcgttcc ggcgtctcct ggcgcgccc ggctcccggc    600 tgtccccgcc cggcgtgcga gccggtgtat gggcccctca ccatgtcgct gaagccccag    660
cagcagcagc agcagcagca gcagcagcag cagcagcaac agcagcagca gcagcagcag    720
cagcagccgc cgcccgcggc tgccaatgtc cgcaagcccg gcggcagcgg ccttctagcg    780
tcgcccgccg ccgcgccttc gccgtcctcg tcctcggtct cctcgtcctc ggccacggct    840
ccctcctcgg tggtcgcggc gacctccggc ggcgggaggc ccggcctggg cagaggtcga    900
aacagtaaca aaggactgcc tcagtctacg atttctttg atggaatcta tgcaaatatg    960
aggatggttc atatacttac atcagttgtt ggctccaaat gtgaagtaca agtgaaaaat   1020
ggaggtatat atgaaggagt ttttaaaact tacagtccga agtgtgattt ggtacttgat   1080
gccgcacatg agaaaagtac agaatccagt tcggggccga acgtgaagaa ataatggag   1140 agtattttgt tcaaatgttc agactttgtt gtggtacagt ttaaagatat ggactccagt   1200
tatgcaaaaa gagatgcttt tactgactct gctatcagtg ctaaagtgaa tggcgaacac   1260
aaagagaagg acctggagcc ctgggatgca ggtgaactca cagccaatga ggaacttgag   1320
gctttggaaa atgacgtatc taatggatgg gatcccaatg atatgtttcg atataatgaa   1380
gaaaattatg gtgtagtgtc tacgtatgat agcagtttat cttcgtatac agtgccctta   1440
gaaagagata actcagaaga atttttaaaa cgggaagcaa gggcaaacca gttagcagaa   1500
gaaattgagt caagtgccca gtacaaagct cgagtggccc tggaaaatga tgataggagt   1560
gaggaagaaa atacacagc agttcagaga aattccagtg aacgtgaggg gcacagcata   1620
aacactaggg aaaataaata tattcctcct ggacaaagaa atagagaagt catatcctgg   1680
ggaagtggga gacagaattc accgcgtatg ggccagcctg gatcgggctc catgccatca   1740
agatccactt ctcacactc agatttcaac ccgaattctg gttcagacca aagagtagtt   1800
aatggaggtg ttccctggcc atcgccttgc ccatctcctt cctctcgccc accttctcgc   1860
taccagtcag gtcccaactc tcttccacct cgggcagcca ccctacacg gccgccctcc   1920 aggccccct cgcggccatc cagaccccg tctcacccct ctgctcatgg ttctccagct   1980
cctgtctcta ctatgcctaa acgcatgtct tcagaagggc ctccaaggat gtccccaaag   2040
gcccagcgac atcctcgaaa tcacagagtt tctgctggga ggggttccat atccagtggc   2100
ctagaatttg tatcccacaa cccacccagt gaagcagcta ctcctccagt agcaaggacc   2160
agtccctcgg ggggaacgtg gtcatcagtg gtcagtgggg ttccaagatt atcccctaaa   2220
actcatagac ccaggtctcc cagacagaac agtattggaa ataccccag tgggccagtt   2280 cttgcttctc cccaagctgg tattattcca actgaagctg ttgccatgcc tattccagct   2340
gcatctccta cgcctgctag tcctgcatcg aacagagctg ttaccccttc tagtgaggct   2400
```

```
aaagattcca ggcttcaaga tcagaggcag aactctcctg cagggaataa agaaaatatt    2460
aaacccaatg aaacatcacc tagcttctca aaagctgaaa acaaaggtat atcaccagtt    2520
gtttctgaac atagaaaaca gattgatgat ttaaagaaat ttaagaatga ttttaggtta    2580
cagccaagtt ctacttctga atctatggat caactactaa acaaaaatag agagggagaa    2640
aaatcaagag atttgatcaa agacaaaatt gaaccaagtg ctaaggattc tttcattgaa    2700
aatagcagca gcaactgtac cagtggcagc agcaagccga atagcccag catttcccct     2760
tcaatactta gtaacacgga gcacaagagg ggacctgagg tcacttccca aggggttcag    2820
acttccagcc cagcatgtaa acaagagaaa gacgataagg aagagaagaa agacgcagct    2880
gagcaagtta ggaaatcaac attgaatccc aatgcaaagg agttcaaccc acgttccttc    2940
tctcagccaa agccttctac tacccccaact tcacctcggc ctcaagcaca acctagccca    3000
tctatggtgg gtcatcaaca gccaactcca gtttatactc agcctgtttg ttttgcacca    3060
aatatgatgt atccagtccc agtgagccca ggcgtgcaac ctttataccc aataccttatg   3120
acgcccatgc cagtgaatca agccaagaca tatagagcag taccaaatat gccccaacag    3180
cggcaagacc agcatcatca gagtgccatg atgcacccag cgtcagcagc gggcccaccg    3240
attgcagcca ccccaccagc ttactccacg caatatgttg cctacagtcc tcagcagttc    3300
ccaaatcagc cccttgttca gcatgtgcca cattatcagt ctcagcatcc tcatgtctat    3360
agtcctgtaa tacagggtaa tgctagaatg atggcaccac caacacacgc ccagcctggt    3420
ttagtatctt cttcagcaac tcagtacggg gctcatgagc agacgcatgc gatgtatgca    3480
tgtcccaaat taccatacaa caaggagaca agcccttctt tctactttgc catttccacg    3540
ggctcccttg ctcagcagta tgcgcaccct aacgctaccc tgcacccaca tactccacac    3600
cctcagcctt cagctacccc cactggacag cagcaaagcc aacatggtgg aagtcatcct    3660
gcacccagtc ctgttcagca ccatcagcac caggccgccc aggctctcca tctggccagt    3720
ccacagcagc agtcagccat ttaccacgcg gggcttgcgc caactccacc ctccatgaca    3780
cctgcctcca acacgcagtc gccacagaat agttttcccag cagcacaaca gactgtcttt    3840
acgatccatc cttctcacgt tcagccggcg tataccaacc cacccacat ggcccacgta     3900
cctcaggctc atgtacagtc aggaatggtt ccttctcatc caactgccca tgcgccaatg    3960
atgctaatga cgacacagcc acccggcggt ccccaggccg ccctcgctca aagtgcacta    4020
cagcccattc cagtctcgac aacagcgcat ttcccctata tgacgcaccc ttcagtacaa    4080
gcccaccacc aacagcagtt gtaaggctgc cctggaggaa ccgaaaggcc aaattccctc    4140
ctcccttcta ctgcttctac caactggaag cacagaaaac tagaatttca tttattttgt    4200
ttttaaaata tatatgttga tttcttgtaa catccaatag gaatgctaac agttcacttg    4260
cagtggaaga tacttggacc gagtagaggc atttaggaac ttgggggcta ttccataatt    4320
ccatatgctg tttcagagtc ccgcaggtac cccagctctg cttgccgaaa ctggaagtta    4380
tttatttttt aataacccctt gaaagtcatg aacacatcag ctagcaaaag aagtaacaag    4440
agtgattctt gctgctatta ctgctaaaaa aaaaaaaaaa aaaaaatcaa gacttggaac    4500
gccctttac taaacttgac aaagtttcag taaattctta ccgtcaaact gacggattat     4560
tatttataaa tcaagtttga tgaggtgatc actgtctaca gtggttcaac ttttaagtta    4620
agggaaaaac ttttactttg tagataatat aaaataaaaa cttaaaaaaa atttaaaaaa    4680
taaaaaaagt tttaaaaact gaaaaaaaaa aa                                  4712
```

```
<210> SEQ ID NO 2
<211> LENGTH: 151001
<212> TYPE: DNA
<213> ORGANISM: Homo sapiens

<400> SEQUENCE: 2
tcccaaagtg ctgggattac aggcgtgagc caccacactg gccaaaactt gttcttaaga      60
ttgtattctg ggaccttgat tccaatcaga gaaaagtgat tgtatttttt tattttatt     120 tttttagat aaagtttcgc tcttgttgcc caggctggag tgcagtggtg ccctctttgg     180
tcactgtaac ctccgcctcc tgggttcaag cgattctcct gcctcagcat cctgcgtagc     240
tgagatcaca gatgcccacc accacgccca gctaattttt tcgtattttt agtagcgatg     300
gggtttcacc atgttggcca cgctggtctt gaactcctga cctcaggtga tccatccgcc     360
tcggcctccc agagtgctgg gattacaggt gtgagccacc gcgccaggcc aagtgtttgt     420
atttctatta agaaagaat ataacgggac accattgacg acctgctcca ttgcaggcct     480
ccttgctgtt cctcagactc cccctcaga gcctttgccc tcgctgtgcc ctccacctgg     540
agcgtttctc cccaggatcc tcatgcccat gctcatttgg gtccctgccc catgtcaccc     600
tctccaggag cttcccctca cagcagccct ggcctgtacc acagccgggt acaggtattt     660
ttttgtttca actggttttt tagttccagt ttcctttagg ttactttatt tatttattta     720
tttatttatt ttttgagacg gagtctcgct ctgtcgccca ggctggagtg catgatctcg     780
gctgactgca acctccacct cccggattca agcaattctc ctgtatcagc ctcccgagta     840
gctgggatta caggcgccca ccaccacacc cggctaattt ttatatttt ggtagagacg     900 gggtttcacc atgttggcta ggctaggtta attttttaaag ggttttgcaa tggtcccttg     960
atctactttt taccttagat gggaaataaa actgatttcc tacattggca gaatacaatg    1020 atcattttg cctggactat ctaggaggtt aatttcagtt ggactactga aaactgctgg    1080
ttcaatcatt ctccacgttt atctaagtct ttacctttat ctggacagtt ctaggacatt    1140
gaggggaatt ttggtgtttc ttcccctatt atttcctgaa gtcatttcac tttaaaaaac    1200
aatagattca ctgctcaaaa aaaaaaaaa aagttaccta cttt ctactt gcttccagtt    1260 taactgcaac acattttaaa aagagtctac tgtgctggct gggtaagtta aattaaaact    1320
tctaaagggt ccaaggtcta aagttcgcac attgttttga ggtcggctct gtctctaccg    1380
agggagatcc cattatccgt agttctacca gtcccaatcc catatatttc ctttagaatc    1440
tcatgaatga ggaaaaagaa gttcaagtga gggaacatag gttcaaatga aggtcagata    1500
cctaaaagag ttttctggtg actgtgcgcg gctggggtgg aaaaagtggg gaaaaggtac    1560
ccagatgtgg gtggccccgg agggttgctc cactccagcc ccggcagggc aggacagcgc    1620
ggcctgcctg gtagatgccc cgagccactg gagcgcctac tgtgtggcgg gcggggacg    1680 gcaggaaaac ggcaggatgc tgtgtccccct gaatctggca gggttctagg tgctttacac    1740
gtagcaagac acattctccg ccccaaggca ctcgcagtca gtccattttc tgggttgcat    1800
caggtggggg caaactaggt ccccgcagaa gtgaagatgc tgaaggaata cagtaggaga    1860
agaaatgctt ctctcctgtc ctccacacca ggcaggcccc agaggctgag accgacacgc    1920
cctccccgaa gggcagaccc gccttgagga aggcggatcc gggtagggac cgccgcctgg    1980
ccctcacccg accccgaga aagcaaccca gcgcgccgcc cgctcctcac gtgtccctcc    2040
cggcccgggg gccactcac gttctgcttc cgtctgaccc ctccgacttc cggtaaagag    2100
tccctatccg cacctccgct cccacccggc gcctcggcgc gcccgccctc cgatgcgctc    2160
```

```
agcggccgca gctcctcgga gtcccgcggt ggccaccgag tctcgccgct tcgccgcagc    2220
caggtggccc gggtggcgct cgctccagcg gccggcgcgg cggagcgggc ggggcggcgg    2280
tggcgcggcc ccgggaccgt atccctccgc cgcccctccc ccgcccggcc ccggccccc    2340 tccctcccgg cagagctcgc ctccctccgc ctcagactgt tttggtagca acggcaacgg    2400
cggcggcgcg tttcggcccg gctcccggcg gctccttggt ctcggcgggc ctccccgccc    2460
cttcgtcgtc ctccttctcc ccctcgccag cccgggcgcc cctccggccg cgccaacccg    2520
cgcctccccg ctcggcgccc gcgcgtcccc gccgcgttcc ggcgtctcct tggcgcgccc    2580
ggctcccggt tgtccccgcc cggcgtgcga gccggtgtat gggcccctca ccatgtcgct    2640 gaagcccag cagcagcagc agcagcagca gcagcagcag cagcagcaac agcagcagca    2700
gcagcagcag cagcagccgc cgcccgcggc tgccaatgtc cgcaagcccg gcggcagcgg    2760
ccttctagcg tcgcccgccg ccgcgccttc gccgtcctcg tcctcggtct cctcgtcctc    2820
ggccacggct ccctcctcgg tggtcgcggc gacctccggc ggcgggaggc ccggcctggg    2880
caggtgggtg tcggcacccc agcccctcc gctccgggcc cggcgtcccc tccccgcgg    2940 cccgcgccgc cgtccccgcc ccgtgacccg ccgggctacc cggggtgggc tggggggccgg    3000 cagcgcgggg gagactcgct cgggcctgag ccccgaggct cggccggtgg gcgcagccgg    3060
ggtcctctgg gattgtcagg cctgtccagc ctcccgcagc atccccgccc cctccccgg    3120 cggtcaagat ggagggagcg gcggcctcc cctccccacg cgtgttggga ggggttctcg    3180
ggtagcggcg atggtcagcc ccggctcccc cttccgcacg atcctccgcc cgcagcgtgg    3240
ggatgctcgg gcagctcctc cactcccggt ttaggtgtga acgttggagg ggtctggagg    3300
ctgtggtggc gttttccgga acatgtcccc ctccatgggg gacatctctg gaggggagaa    3360
gttagggccg cgtcccccgt gccggttaaa ggggtaggca ccgggctcct ccggaatcat    3420
cagggtctgt cggggctctc tcccgcccc ctccgagtcc tgggaaagat cggaggacgg    3480 ggtgagaca gtgggccctt ggcccccgca ccctctgcg ttcgtgtccg aggcggcggc    3540
gggggctccc gaactcccct gaaatcgtgg ggctccatgt ggcctccggc agcgttccac    3600 cctccccac ctggggaagg gaaggggtgg ggagtgcccg gccccgtccc ggccttcctc    3660
cttcccccgc cagacctctc cggcgcgcgg gtggtggccg atccgcattg ctgttcgagg    3720
ccgcagtgga gaaggcgcct gtggaacatc ggtgggtgag ggctgacccc aggctggacc    3780
ctggagatcc ggggtggcgg tgctggtggc aggggcggg caccctgcgc acttatccca    3840 accccgccc caatttcgga aatgctagga gagagagatt gcagcagggg acgtggtcgg    3900
gttcctgaag gcagaaaggc gggtgtttac tagcgtcttt ttccctccta agccgggtt    3960 gtagtagggg ctggggctc agtgttgtcc cggctaactg ggtttgactc gagggtgtgt    4020
ttgtgcagga gggcctgttg ggggtggcgg gcggttgtca gttcgtattt cacgaactaa    4080
gaaaatgctt agtgttcaaa gggagaagga aacgtcaata gactccattc cattgtggcc    4140
ggtgtcctta acttcgggag tgccgccaga gcttaccaag ggcacgcaag tccatttccc    4200
ttgtgcctca agtccatccg tgttgtaggc actactgtgc cttctttagg cctaggccgc    4260
cggcttgacg gcgggtgacc ggcgtcctcc ttaaataggc atcttgggct ttggaaggtg    4320
gaataagagg attttcatt caccgagtt ttcttttga aaacacattt tcagcaaccc    4380
atttccaaag aattttatt tacagcagaa attccccatc aagaggaatc agctggtttt    4440
taaggaattc tgctgcctc aaagggggcg gaaacagtcg gttatttgac tttacacgcc    4500
ccgccccccc ttccccttct ctgagtctga agcatcccaa acactactta gccaaactag    4560
```

```
ttcagatgaa gtgatcgttt ccccaagtag ggtaacttca gtttcccttt ttcgttggca   4620
tctagcgaaa aatgaaaaaa tttaaaatac aactttata  gaaaaggatg tattctgttt    4680
ttactttctt aggtattagg aagagatttg gcagataatt caacatgttc aaatatataa   4740
acattaaaac taaggttatt aagttgcatt gactactagg cttaaaaatt agattataag   4800
agaatttgct cctgagtagt ttgagtgatc aaagatattt ggaatgtttt agtaccacaa   4860 ggtcttttt  ctgttccttg aggctttaca acaatttaag gttaatttag attttcctt    4920 gctttaagtt cttttacttg agacctaaat ggcagccctt attctttctg atgaataggt   4980 gaaatttgt  ttactgtgtt ggatttgtgt aatgtgaagt tttattcttg aacagatcgt   5040
taatgtactt gtagaattac tttgaatttg aatcactttc ctgcattcct tgtaaataag   5100
tttcagcttc tagaatctcc tcacttaggt tgtgcgtat  caacagtgaa aataagtctc   5160
tgagagcaag ggtgaaaaaa aatgcagcat tcggtttgac aagtttcgag atagcaaaat   5220
atgcttgaaa gtctggaaat tcacatctgc tttaagaaac atttcataat ttgactttgt   5280
gtgtgtgtgt gtgaatagtt tttcatgact ttcagaagtg atttattttg ttctttgtta   5340 tatatattt  tgaaggtggc tgttttagga aagataatgt aatcacaata ttagaacata   5400
attttactgt aatctaattt tgtgtgtgtg tgtgtgtgtg tgtgtgtgtg tgtgtgtgtg   5460
ttttggatgg aatctcactc tgtcgcccag gctggagtgc agtggcctga tctcagctta   5520
ctgcagtctc tgtctcctgg gttcatttaa gtgattctcc agcctcagcc tccccagtag   5580
ctgggattac aggttcgtgc taccacacct ggctaatttt tttgtatttt tagtgaggac   5640
gggattttgc catgttggcc aggctggtct cgaactcctg acctcaagtg atccgcctgc   5700
cttggcctcc caaagtgctg ggattacagg cgtgagctac tgcccctggc caatttttgt   5760 attttagta  gagatggggt ttcaccatgt tggccaggct ggtctcgaac tcctcctgac   5820
ctcaagtgat tcgccagcct cggcctccca aagtgccagg attacaggca ggaatgagcc   5880
actgccccca accatcagtc taattcttat ttttgctttt tacctttttca tttttatgta   5940 gtagaggtga ttgtgtatgt tattttgtag ttagcttttt tccctgaac  gttgtattgt   6000 aaatgtaaat tttttttttt tttttgaga  cagagtctcg gtgtttgccc agtctgaagt   6060
gcagtggtac gatctcagct cactgcagcc tctgactcct gggttcaagc gattctccca   6120
cctcagcctc ttgagtagct ggggctacag gaatgttcca ccacgcttgg ctaattttg   6180 tattttggt  agagacaagg tttcaccatg ttggccagtt tggtctcgta ctaccgacct   6240
caggtgatgc gcccgcctcg gcctcccaaa gtgctgggat tgcaggcgtg agccactgcg   6300
cccggctgta aggttttac  ttaaccattc tattgttggg aattgggttt ccactttttt   6360
gttatagata gtggtgcagt gaacattttt aaatagcttt ttgcttcagt gtaattattt   6420
ccttagagaa agttaccaag agtggtttta ctagttcaga gggcttcagg attttttatgg  6480 ctcttgctag cggtgctcta ttattcttta gaagacttgt attacttcca gtgtcaagaa   6540
ggttgctctt ccatggaatg gtttctttgt agtttgtcaa atattgtggg gaattttaa    6600 aggaaaaatt gcattttac  tgtcaagtgc atatatatt  aagtgctttt gttagttact   6660
ggattattga tatttgagtt taatttggtt cctctgagga tttaataagg taatatatgt   6720
gaagatgttt tgaaacctgt aaccattatt attaatgagg gtacttggtt tatctgtcgt   6780
gctgatagta ctgagtaaag tgcaggaatg aaattcctga ggaactgttc taaagctttg   6840
ttgttgttgt taacctttct ttttcatctg aaagtgttt  ttattagctg ctagcctatg   6900
```

```
accaagttat ttttggtaac ttttttgtaa tttcatggca ctattgggaa ttttcgctgg    6960
ttgactcttc ttcttctaca ttcccttccc cattaaaaat aaaaatatgg atttacaatt    7020
gttactctat tcctaaacct aaataatatg acattagaat tgcttgggat acaggattca    7080
gtctgaataa aatattttc ttttagtgat tttcagctta gtatttttac tgcttctttc    7140
tcttgaggca ttgcaactta aaaattgtgc tgtttagcca ggcgcctgta atcccagcta    7200
cttgggaggc tgaggcagga gcatcacttg agcccaggag gcggaggttg cagtcagctg    7260
agattgtgcc actgcactcc agcctgggag acagagtgag actctatctc aaaaaaaaaa    7320
aaaatgtgct gtgatttaat gtagttgttc atcatgcttc catttaaatt tcagtgagac    7380
tgttcatctt ttgcagttaa atatcttgta aagggccta aaatatctac gttgaataca    7440
gctttattga agcatctatg tacatggggt ttttgggatg aatcagtgaa taaagcaaac    7500
atattgtcct tttggagttt acattctaat gtgactaggc agacaatgag acattaaatt    7560
accagcctat gtataatagt gtataagagc tatggaatta aagaaagca gattaaaggt    7620 atagggagtg tggggagggg aatgagttac aattttaaat ggattggggg aacttaattg    7680
aggagctaac atttgagcaa agatttgaag gttgggtatt tagccgtttg cttttatct    7740 aggttaatta gtcatgtggc ttcattagta atttataagg tttaaatggc atcatccttt    7800
gttattcttt tatgtgcaca ttgatactaa ccatctctga agttagacca aaaaagttaa    7860
ttgacattga gggtcattag aggtaaattg tagatggcta ttactaacca aagagacatg    7920
ttttgttttt cttttgggct tacgtatttt acctaattag tttagttttt gtttcaagta    7980
tgtggagaaa ataaactttt taagtttggg ccaaaacttg ctttggtttt cttttctctt    8040
ttcttttttt tttttaaga gaaaatgta agcctgtagt tgcttaaaga ttccacattc    8100
tgaaacagtg aaaacatggg atcagtcatg gtgttccttt ttttggttaa atgtaaactt    8160
gtattttcag tgttactcta attagcaatg gtttatactt ctacataagg gatgttaact    8220
catattgtag ctatttaata gccatatatt ttgacttaaa ggaggatctc aaggccaggc    8280
gcggtggctc atacctgtaa tcccagcact ttaggaggct gaggcgggtg gatcacctgg    8340
ggtcaggagt ttgagactag tctggccaac atggtgaaac ccccatctct actaaaaata    8400
caaaaattag ccgggcatgg tggtgggcgc ctgtaatccc agcttcttgg gaggctgagg    8460
gaagagaatt gcttgatccc ggaggttgca atgagtgcgg aggttgcagt gagctgagat    8520
catgccatta cactccagcc tgggcaacag agcgagactc tgtctcaaaa caaacaaaca    8580
aacaaaaaaa ggaggatctc attttttttgt cctaaatagc tacagccgtg ttagaactgt    8640
caccttagca aagtattgtt ttttacttt gaaacgaatt ttaaggtttt agaagattgt    8700
tctctagaat tacaattttc tgttttgact agtgatagta ttttgatgtt gtgtaaatag    8760
ttgagcatga acaaaaccct attttttttt ttagctattt caagtgattg tgacaacttc    8820 aacgagatg taaacagttt attaacagtc acacctatta tcttttttt tttttttttt    8880 ttttgagacg gagtcttgct ctgtcgccca ggctggagtg cagtggcacg atctctgctt    8940
actgcaacct tgcctcccg ggttcaagtg attctcctgc ctcagcctcc tgagtagctg    9000
ggtctacatg cgcacaccac cacgcctggc taattttgt attttagta gagacagggt    9060 ttcaccatgt tggctagaat ggtctcaaac tcctgacctc aggtgatcca cctgcctcag    9120
cctcccaaag ttctgggatt acaggcatga gccaccgtgc ttggccgctg ccgtatcttt    9180
ttaaatgaaa gtacttgtgt ttttttgtt ttttccaaa ggatatctgg gtcatctatg    9240
atgttactgt taccatctaa gggtttttt gtttgtttt gagacagagt ctctgtcgcc    9300
```

```
caggctggag tgcagtggcg tgatcttggc tcactgcaac ctccgcctcc caggttcaag    9360
caattctcct gccttagccc tcccgaatag ctgggattac aggcacccgc caccatgcct    9420
ggctaagttt tgcattttta gtagatatgg agtttcacca tgttggccag gctgctcttg    9480
aactcctgac ctcaggtgat tcgcttgcct cggcctccca aagtgctggg attacaggcg    9540
tgagccaccc ccgcccagcc tcatgagcta aggtgttttt ttttttttttg agacagtttt   9600
gctctttccc aggctggagt gcagtggtgc aatctcagct cactgcaacc tctgtttccc    9660
gggttcaagc gattctcctg cctcagcctt ctgagtagct gagattacag gtgcctgcta    9720
ccccactcag ctaattttttg tatttttagc agagacaggg tttcaccatg ttggttaggc   9780
tcatctcgaa ctcctgacct aagcgatcc acctgccttg gcctcccaaa gtgctgggat     9840
tataggcatg agccaccgtg cgcagcctac cctgtctctt aaaaaacagt aacaacaaca    9900
acaacaacaa aaaatcctaa atcttaaaaa tggaaggcaa aaactctaag ctttgagaga    9960
ttaggggact gcccaaagc aatatttgta ggattttatt acacctctcc ctttatttat    10020
ttttttagag tcaaggtctc cctctgtcac ccaggctgga gtgcagcctc aatctatggg   10080
gccaagcatt tctcctgtct tagcctcctg agtagctgga actacaggtg tacaccagct   10140
ggctaacatt taaattttt gtagagacag ggtcctgcca tgttgcccag attggtctca    10200
aactcctggg ctcaagtgat cctcctgcct cagcttccca aagtgctgag attacaggtg   10260
tgagccactg caccgagccc cctcccttta ttttatttt taaattttaa gttctggggc    10320
ccctcccttg aaataaatag aaacgtaata tatacacaag atcatgctgt gtattttaag   10380
gcaatggtcc tcaaccttttt aacactagg gaccggtttt gtggaagatg gttttccat    10440
agggcaggg gatgatttttg agatgaaact gttccaccgg ccgggcacgg tggctcacgc   10500
ctgtaatccc agcactttgg gaggccgagg cgggcagatc acgaggtcag gagatcgaga   10560
ccatcctggc taacatggtg aaaccccct ctactaaaaa tacaaaaaaa ttagctgggc    10620
gcggtggagg gcgcctgtag tcacagctac tccggaggcc gaggcaagag aatggcatga   10680
aacccgggag gcagagcttg cagtgagctg agatagcacc actgtacttc agcctggggg   10740
acaaagtgag actccgtcta aaaaaaaaa aattgttcca cctcagatca ttatgcattt    10800
gttagattct cataaagagc atacaaccta catctcttgc tatatgcagt tcccagtagg   10860
gtttgtgctt ctataagaac ctaatgctgc acctgatcta acaggtgggg ctcaggtgct   10920
aatgctcaca cagctcctgt tgtgcagtct ggttcctaac aggcctgttt tttttttttt   10980
aattagatgg agtctcgctc tgtcaccagg ctggagtgca gtggcacgat ctcagctcac   11040
tgcaacctct gcctcccggg ttcaagcgat tctcctgcct tagcctccca tgtagttggt   11100
actacaggcg cacactgtga tgcccagcta atttttgtat ttttagtaga cgggggtttt   11160
caccatgttg gccaggatgg tgtcgatctc ctgaccttgt gatccgccca acagcctccc   11220
aaagtgctgg aattacaggc gtgagctgct gcgtccggcc ccctaacagg cttgttttat   11280
ggaatacagt cacggacagt acttgccctt caggatatct tttttgtaacc ttgatttttgg  11340
cttgctaaaa taggaggtct attttctttt ctttgttttt aatgtatgtg gttctgtact   11400
tacgtggtgt gaaatctaca taaatgttaa atccttggtt atttatttat tttgagacag   11460
agtctcactc tgtcacccag tctggaaagc agtggcataa tctcggctca ctgtaacctc   11520
cacttcccag gttccagtga ttcctcctgcc tcagcctcct gagtagctgg gattacaggc   11580
atgcaccact acacctggca aatttttgta tttttttta gtagagatgg ggtttcacca    11640
```

```
tgttggccag gctcgtcttg aactcctgac cttaggtgat ctgcctgtct tggcctccca    11700 aagtttggg  attacagcat gagccactgc gcctcgcctt atttttttga gacaggttct    11760
agctctgtca cccaggcggg agtgcagtgg tgccatcatg gctcattgca acctcgagtt    11820
ctcaggccca agtgatcctc ctatctcagc ctcctgagta gctgggacca caggcatgcg    11880
ccactatgcc cagcaaaatt tttgtttcac tctgttgcct agggtggggt gcagtggcag    11940
gatatcggct cagtgcaacc tctgcctctt gcgttcaaat gattctcatg cctcagcctc    12000
ccgagtagct gggattatag gcatgcgcca ctacacctgg ctaattttt g tattattggt    12060 agagatgggg ttttatcatg ttggccaggc tggtctcgaa ctcccgacct caggtgatcc    12120 ataccttg   gcctcctgaa gtgctggaat tacaggcata agccactgcg cctagctttt     12180
ttgtttgttt ttattttgta gggacagaga ttttacctgt tgcccaggat ggccttgaat    12240
tcctgacctc aaacaatttg ccctccttgg cctcccaagg tgctgggatt acaggtgtga    12300
gccactatgc ctggctggtt ttttaaatta ttattattgt ttgtgtgtgt gtgttgcagg    12360
atcttaccct gtcacccagg ctggaatgca gtgatgtgat ctcggcttac tgcaacctcc    12420
gcctcctagg ttcaagtgat tgtcctgcct cagcctcctg agtagctggg ataacagctg    12480
tgtgccacca tgcctggcta atttttgtat ttttagtaga gatggggttt catcatgttg    12540
gccaggctgg tctcgaactc ctgaccttag atgatccacc cgcctcgtcc tcccaaagtg    12600
ctgggattac aggtgtgagc caccgtgacc agtttggttt agttttttt tttttttttt    12660 tttttttttt tttttgagaa atctcgctct gtcgcccagg ctagagtgcg gtgacacaat    12720
ctcagctcac tgcaagctcc acctcccagg ttcatgccat tctcctgcct cagcctcccg    12780
agtagctggg actacatgcg cccgccacca tgcccggcta atttttttta tgcattttaa    12840
gtagagatgg ggtttcactg tgttagccag gattgtctca atctcccgac ctcttgatct    12900
gcccgcctcg gcttcccaaa gtgctgggat tataggcatg agccaccgcg tccggcctgg    12960
tttggtattt tttttatgag tctgggttgt ttatgaaaac ttgtcacagc tgttaacctt    13020
aacttttttt ttttctttt tttccgagac ggagtctcgc tctgtcacct aggctggagt    13080
gcagtggtgc gatctcggct cattgcaacc tctgcctccc aggttaaagc gattttctg     13140 cctcagcctc ctgagtagct gggactgcag gcacgcacca tctcgcctgg ctaattttt g   13200 tattttagta gagatggggt ttcaccatat tggccaggct ggtctggaac ttctggcctc    13260
aagtgatcca cctgccttgg cctccatgc  ctggcaacct taacttttta tttgctggta    13320
attatttgtg tttgcattca tgtgaaaatt tgaaattctc attaacattt aaagattctt    13380
acatagattg cttgtaattt taaccctgaa gttgtgtcaa gtgactttac aatgtcaatt    13440
tgttttattt atttattat  ttatttattt atttattttt gtgataggat ctggctctgt    13500
tgctaaggct ggagtgcagt gttgcaaata cggctcactg caacctctgt ctcccgggtt    13560
caagccatcc tcccacctca gcctcccaag tagttggaac tactggtgcg ccccacagtg    13620
cctgcctagt ttttttgtat tttcagtaga tgtggagttt gccatgttg  atcttgaact    13680 catggcctcg agtgatccac cccacttagg cctcctaaca tgctggtgtt acaggtgtga    13740
gccactgtgt ccagcccgaa aatgtcagtt tcgtgccatg attaatagct aactacattt    13800
tgggaatgta ataaaatttc attctataat gaagtctttg taaaactcat tagttgtggt    13860
atgaggcttg tcgcaatat  aagtgaacgt ggtttatttt tattaactgt atcagaactt    13920
tagaatgttg gtctcctgaa accattgcct tgagaggctt tattgaacag tgttgccaat    13980
gatcagtttt ttttaaatt  tccttttttt tgagactgag tcttaccctg ttggccaggt    14040
```

```
tggagtatag tggtatggtc atggctcact gcagcctcaa catcctgggc tcaagcagtc    14100
ctcctacctc agtctcccga gtagctggaa ctacaggtgt atgccaccat gcctggcttt    14160
tgtatatttt gtagagacag ggtttagcca tgttgcccag gctggtctca aactcttaaa    14220
ttcaaatgat ccacccacct agttttccca aagtgcttta attacatgtg tgaggcaccg    14280
tggctggcca ggtcaaatat ttttcattga cgttttcat attgctttt aaagtcatgt    14340 taaaatattc ttaataattt ttctaagtgg aattaatctt gattataatt ttagtttttt    14400
ataaagggcg ggttttgaaa caagtactgc attttctttt tcgggtttat aaacatttgc    14460
tgtggacttt gtgcagttaa ctattttcat tcctgaaaca catttcgaaa tcaggaattg    14520
aagactaaat gtcttttcac tgaagcttga gcagatttta gaaggggag ttctttttt    14580 tttttttt tttggtagaa atgggggtct tgttatgttg cccaggctgg cctccaactt    14640
ctgggcttaa actgtcctcc tgctttagcc tctggtctgg agagttcttt atggcctctt    14700
tgagaacttt tactttacac atgattctat ctagctttct tttctgatgt acatattggc    14760
agcaagtaga aaagcaatgt tttcagaggc agatatatta acagcaatga gaaataacag    14820
tagcgtgata gaaagttgaa agacttagct gggtgcggtg gctcacgctt gtaatcccag    14880
cactttggga ggccaaggag ggtggatcac ttgaggtcag gagttcgaga ccagtctggc    14940
caacatggtg aaaccctgtc tctactgaaa aacagaaaaa gggccgggcg tggtggctca    15000
cccctgtaat cccagcactt gggaggttg aggagggcgg attacaaggt caagagattg    15060
agaccattct ggccaacagg gtgaaacccc atctctacta aaaatacaaa aaattaaat    15120 gggcgtggtg atgtgtgcct gtagtcccag ctactcggga ggctgaggca ggagaattgc    15180
ttgaacccgg gaggcagagg ttgcagtgag ccgagatcgg gccactgcac tgacgacaga    15240
gggagactcc gtctaaaaaa aaaaaaaaa aaaaaaacc agacttgggg ctgggcgggc    15300
gcctgtaatc ccagctactt gggaggctga ggcaggagaa tcgcttgaac ccggaggtg    15360 aaggttgcag tgagctcaga ttgtgccact gtgcccagc ctgggccaca gagcagagtg    15420
agactctgtc tcaaaaaaa aaaaaagtt tggaagactg gtggctggc atggtggctc    15480 acacctgtaa tcccaacact tgggaggct gaagcaggca gattacctga gcccaggagt    15540
tcaagtccag cctgggcaac acagggaaac cccatctcaa caaaaatat taatacaaaa    15600 aatttagcca gtcatggtcg tgcacttctg tagtctcagc tacttgggag gctgaggcag    15660
gtggttcact taagtctgga tgtcgaggtg agccatgatt gcaccactgc actccagcct    15720
gggcgttaaa atgagacctt atctcaaaaa aacaaagcaa agagcctggg aactactaaa    15780
atgggaacta ctaaaaaaca gacacaagag ctcaacaagt ataccattct gggaggtttt    15840 tttttttt ttttttttt tttttgagat ggagtttgc tcttgtcacc caggctggag    15900
tgcaatggcg ccatctctgc tcactgtagt tccgcctccc aggttcaagc agttctcctg    15960
cctgactcct gagtagctgg gagtacagat attggtcaca caccgggtta attttgtat    16020 ttttagtaga cggggtttt ccccattttg gccaggctgg tctcgaactc ctgacctcag    16080
gtgatccgcc tgcttcagcc tcccaaagtg ccgggaccac aggcgtgagc caccgcacct    16140 ggctttttt ttttgacata gaatcttgtt ctgttcccca ggctggagtg caatggtaca    16200
atcttggccc actgcaacct ctgcctccca gcttctagcg attttcctgc ctctgactcc    16260
tgagtagctg ggattacggg tgcccgccac cacacccgga taattttgt attttagta    16320 gagatggggt tttgccatat tggccaggcc ggtcttgaac tcctgacctc agatgatcca    16380
```

```
cctgcctagg cctcccaaag tgccgggatt acaggcgtga gccaccactc ccggcctggg    16440
agttttgact gtaagtttat agctgtatat cttaggccct aagggcatta ctgttttata    16500
gcacagtgta gttagttaat gtgctcataa tggtgactca taacaccagg ttaaatgatt    16560
ttttatatct cccaaagaag tatttttcaa tctgcagatc atgaccccct agtagattgt    16620
gaaacacatt agtggattat gacaagcatt tttagaaaaa tgaaaagaa taagaagtgt     16680 taggatgcat tgcattattg aaataattgt ttttgagatg gagtttcgct cttagttgcc    16740
gaggctggag tgcaatggcc cgatctgcct cccgggttca agtgattctc ctacctcagc    16800
ctcctgagta gctgggatta cagacatgct ccaccatgcc tggctaattt tgtatttagt    16860
tttagtagag atggggtttc tccatgttgg tcaggctggt cttgaactcc tgacctcagg    16920
tgatccactt gcctcggcct cccaaagtgc tgggdataca ggcatgaacc cctgtgcccg    16980
gcctaatttt tgtatttta gtagagatgg ggtttcacca tgttggccag gatagtcttg     17040
atctcttgac ctcgtaatct gcccacctcg actcccaaag tgctgggatt acaggtgtga    17100
gccactgcac ccagctgcca agaattgttt taagctttgg tttgagttaa tgtatatata    17160
ccgcattgta attcaaaatg taattttgg ccaactctgg gcacattgcc tatggactag     17220
tcctgctctg ccacgagcag caacagttca atgaattttt tttttttttt tttttttttt    17280
tttttttttg agacagggtc tctgtcacca aggctagaat gtagtggtgc agtctcggct    17340
cactgcaacc tctgtttcct gggctcaagc gatcctccca cctcagcctc ctgagtagct    17400
gggagtacag gagcacgcta ccatgcctgg ctaatttttg tattttttga agagatgagg    17460
ttttgccatg ttgttcaggc tagtcttgaa ctctggagct cagatgatcc acccaccttg    17520
gtgtccagaa atgctgggat tacagggatg agccaccgtg cctagccaaa aattttttt     17580 taagtaatt tttattgata tagtcaaaaa agttactgct ttagagccag agaaacgcag     17640
taaaaggatt gagaaagagt tttgaggtta tatctaagct agggttgtca gatttggcaa    17700
atagaaatac aggacactca gttaaatttg aattttgat gaacattgac cagttttta     17760 gtataattgt gtattaaatt gcatagaaaa aagttattta tctaaagttg aaatttaact    17820
gagcatcttg tattttatct ggcaactcca gtctaagctg gaatcatggt tcactgtttt    17880
tttttttttt tttttttttt gagtcggagt cttgctgtgt tgcccaggct ggagtgcaat    17940
ggtgcgatct tggctcactg caacctccac ctcctgtgtt caagtgattc tcctgcctca    18000
gcctcctgaa tagttgggat tacaggcacc caccaccatg cccagctaat tttatattt     18060 ttagtagaga cggggttttc gccatgttgt tcaggctggt cttgaactcc tgacctcagg    18120
tggtccgccc acctgggcct cccaacgtgc tgggattaca ggcatgatct accgtgcctg    18180
gccatggttc actcttcagt aactaaaatt taagctctat gaaagcagga actttgtttt    18240
gttcactatt gattgtatcc ctatttcttg aatggttggc acttaactgc ttggtcacat    18300
gtttgaatgg gcaagttact cagccactct caggcttagt ttatttacct attaaaagag    18360
aaagaatatc ttccttggct gggcgcggtg gctcacgcct ataatcccag cactttggga    18420
ggctgaggcg ggtggatcac gaggtcagga gatcgagacc aacctgggca acattgtgaa    18480
acctcatctc tactaaaata gaaaaaatta gctgggcatg gtggtgcgca tctgtagtcc    18540
cagctactcg agaggctgag gcaggggaat cgcttgaacc caggaggtgg aggttgcagt    18600
gagccaagat tgtgccactg cactccagcc tgggcgacag aacgagactc tgtctccaaa    18660
aaaaaaaaaa aaacaaacaa aaaaaaaaac tgagatactg gccgggcgcg gtggctcgtg    18720
cctgtaatcc cagcactttg gaaggccgag gcgggtggat cacgaggtca ggagatcgag    18780
```

```
accgtcctgc ctaacatggg gaaaccctgt ctctactaaa aatacaaaaa attagccagg    18840
cgtggtggcg ggcgcctgta atcccagcta cttgggaggc tgaggcagga gaatggcgtg    18900
aacccgggag gcagagcttg cagtgagcgg agatggtgcc actgcactcc agcctgctgg    18960
gcgacagagc gagactccgt ctcaaacaaa caaacaaaca aacaaaaaaa ctgagatact    19020
aaagtcttaa tattttctgt ttttatgtat ttattttttg agatgggatc ttgctgtatt    19080
gcccaggttg gagtacagta ttgtgatcat ggcttattgc agcctttaac tcctgggttc    19140
aagtgatcct cccacctcag cctcctgagt agctgggacc acaggcacat gcaacatcac    19200
accctgcagt tcttttttttt tttttgagac accgtctcgc tttgtcaccc aggctgcagt    19260
gcgtggtgca atttctgctc actctaacct ccacctcccg agttcaagca gttctgcctc    19320
agcctcctga gtagcttggg accacatgtg tgtgccatca tgcctggtta attttttgta    19380
tttttagtag tgacagggtc ttaccatgtt gcccaggttg gtctcaaact cctgagctca    19440
agtgatctgc ccgccttcgc ctcccaaagt gtctgcgccc tacaatttaa aaaaattttt    19500
gtagagacag tctcactgtt acccgggctg gttttgaact tctgccctca agtactcctc    19560
ttgccttggc ctcccaaagt attgaaatta aggccatgag gcagcacacc cagcctaaat    19620
tcttcttatg ttctgttctt ggcacatagt agatgttcaa caatgtagag tcaaacgcat    19680
ttggagttgg aatggctctg gtgtttttttt ttttttttta aaccagaaac acgtgcagtt    19740
tattgaatgc cattgtagaa aagtgtgtga ggataaacgg ctgatagaga acttggctct    19800
gggggcaggg cgaggaatgg agggtggatg gagtacatgg gaatcagatc acgggcagag    19860
ctcctggcct agataatgcc tcctgatctg ttgatagact tgaaagatca acactgggat    19920
gatgctgagc agaatggtcg taatgatgcg cacaatcagg gcccagatgt tcaggcactt    19980
ggcggtaaag gcataggcct gggccctgat caggtcgcca accatcttct tgtccctaga    20040
cttcacggag taggccaatg ctatgaagcc caggcagcag gagttcatga agtgggtgtt    20100
gaacagggac cagacgacat ggtcgggcac ggagttctcg ctgtggatgg ggatcacggt    20160
ggacattggg ggagcagggt tgtggggtgc ccccagcaca gccacctctt gctcctcctt    20220
gagcatctca tagttagggg gatggccgat gttggcagga gtgaagaggt ttggacattg    20280
tggttcatgg tgtccaggga agaccagctg tggtcgggtt gctggggtgg ttctcagtgg    20340 gccccctccct ttccctggta gtttggattt ctctggctct ggtggttttt tagtactcat    20400
tctatttacg ggtgaagaaa ttgagaccaa gagggttatt taccagagta tctcatcatt    20460
ggctgcataa ctggcattag aatctgatgt acttttattt ctaatacatt tcttttttttt    20520 ttttttttt tgagatggag tctcgctctg ttgccgagcc tagagtgcag tggggcaatc    20580
ttggctcctt gcaacctcca cctcctgggt tcaagctatt cctgtctcag cctcccaagt    20640
agctgggact acaggcacct gccaccacag ccggctaggt tttgtatttt agtagagatg    20700
gggtagcacc atgttggcca ggctggtctc gaactcatga cctcaggtga tccacctgcc    20760
tcggcctccc agtgctggga ttataggcat gagccaccat gcctggcctt tctttgtcgt    20820
ttcctttctt tctcttcatc cctcctctcc ttttttcccc tccccgctgc ctcctcctgt    20880
cttcccttct ttccttcctt tctctccttt ttatttttttc cttcttttt ctttctctgt    20940 ctctcccaac ccttcctctc tccctcccct cctcccctt tctctccccc cctccctccc    21000
cttctctctc cccctcccct tttgttccta agagacaggg tctccttatg ttgctgaggc    21060
tgaccttgaa ctcctgagcc cagatgattc tgcctcctta gtagctggga ctacacccac    21120
```

```
ctcccgttcc gttgtcatct tttttttttt tttcttttt ggagacagaa tcttcctctg  21180
ttgctcaggg tggagtgtag tggcacgatc atagcttact gtaactgtgt aacctcgaat  21240
tcttgggctc aagcaatcat cccatcatcc cacctcagct tgctgagtac ctggggctac  21300
aggtgtgtac caccatgtcc ggctaattac ttttcttatt tttaattttt cggagatagg  21360
atcttgctct gttgcccagg ctggtgtcaa actcctgggc tcaagtgaaa ctcttgcctt  21420
ggcctcccaa agtgttggga gggattacag gcatgagcca ctgcacccag cctcctcttt  21480
cttcccattt aactcctaac cacaccgaac tttctgtctg cagagaggag cattggtcag  21540
cagttcacaa aatggctagg tgtgatggcg tgcacccata gtcccagcta cttggggagc  21600
tgaggtggga ggatcgctgg agcccaggag ttcaaggccc tgggcaacac agcaagacct  21660
tatctctggc tgggcccagt ggctcacgcc tgtaatccca gcactttggg aggctgaggt  21720
gggtggatca cctgaggtca ggagttcgag accagcctgg ccaacatggt gagaccctgt  21780
gtctactaaa agtacaaaaa ttagccaggc acggtggcgc gctcctgtaa tcccagctac  21840
tcggggggc tgagacagga gaatcacttg aacccaggag gaggaggttg cagtgaacca  21900
agaacacgcc actgcactcc agcctgggtg acatagtgag actcttatct caaaaaaaaa  21960
aaaaaaaggt cgtctgtact attgcatgtt agtagtttct ttctgcttat tgttgagtag  22020
tagtctattg tatgcatgta ccagtttgtt catctagtgg tggacattga gttagcaggt  22080
tttggctatt aaaaataaag ctggaggccg ggtgcgatgt ctcacgcctg taatcccagc  22140
attttggaag gccgaggcag gcggatcacc taaggttggg agtttgagac cagcctgacc  22200
aacatggaga acccccatct ctactaaaaa tacaaaatta gccaggcgtg gtggcgcatg  22260
cctgtaatcc tagctactca ggaggctgag gcaggagaat cgcttgaacc cgggaggcag  22320
aggttgtggt gagccaagat tgcaccattg cactccagcc tgggcatcaa gagtgaaact  22380
ccgtctcaaa aaaataaata aataaagctg gtatgaatat ttatgtacag gttttgtgtg  22440
aacatatgat tttatttctc ttggttggaa tgcatagaaa tgagattgct gggttttgtg  22500
gcaagtgttt atttttccag ggtacatata atcctgtgag tgtttattta atttttaaaag  22560
taattgctaa actgtttgct aaagtgactg ctatattttc tttccctagc agtgtatgaa  22620
tttttttttg aggcagggtc ttgctctgtc acccagggtg gagtgcagtg gtgcgatatt  22680
gtctgactgc aacattgacc tcctgggctc aagtgatcct cctgcctcag cctcctggct  22740
gggaccacag gcatgtacca ccacacctgg tagtttgctt tgattttttag tagagaagag  22800
gtctcactat gttgccctgg gtggtgttga actcctgggc tcaagtgatt catctacctc  22860
agcctcccaa agtgctggga ttatagatat gagcccctgt gcctggcctc attgtggttt  22920
taatttgcat ttccctaatg cccagtgata ttgagcattt tttcatgtgt ttatttgaca  22980
ttcataccat cttttggtgat gagaaactat gtttatgcat tgcttaatga tggggatgtg  23040
ttttgagaaa tttttttcggt gatcttatca ttgtacaaat atagagttta cttcacaag  23100
cctagatggt atacctacta gacacatagg ctgtcgtaca gagtattact cttaggctac  23160
aaatctgtat agcatgttgc ggtactgaac actgttggca gatgtaacat aatgttaagt  23220
atttgtgaat ctaaacatat ctaaacatag aaaaggtgag taaaaataca gcgtaaaaga  23280
taaaagtggt atatctgaat aggtcactta ccatgaatgg agcttgcagg acaggaagtt  23340
gcttgggatg agtcatttat cagtggtgtg tgaatgtgca ggcctaggac attactgtat  23400
gctactgtag acaaacactg aacagttagg atacactaaa ttgataaata tctttcttat  23460
tttgttttttt gagatggagt ctcgctctat cgcccaggct ggagtgtagt ggcgtgatgt  23520
```

```
tggctcactg cagtctctgc cttctgggtt caagcgattc tcctgcctca acctcctgaa   23580
tagctgggat tacaggtgcg tgccaccaca cctggctaat ttttgtattt ttagtagaga   23640 cggggtttc accatgttgg ccaggctggt ctcgaactcc tgacctcagg tgatccaccc    23700
gccgtggcct cccaaagtgc tgggattaca gatgtgagcc accgcacctg gccagagatg   23760
aggtcttgct gtattgccca gggcgttgaa ctcctgggct ccagcaatcc tcccacctca   23820
gcttcccacg tagctgggac tgtgggtgca cgccatcatg cctagccgtt ttgtgaactg   23880
ttgaccaatg ctcttttctg cagacagaaa gttcactgtg gttaggagtt aagactttta   23940
acctctgacc tcaagtgatc tgcccacctt gacctcccaa agtgctggga ttacaggtgt   24000
gagccatcac gcctggtcaa aaatatcttt ctttaagagt aaatttacct taacttactg   24060
gttgatcatt gtatataggt ctgttgttaa ttgaaacatg cgggccgggc ccggtggctc   24120
atgcctgtaa tcccagcact ttgggaggcc gaggcgggtg gatcacaagg tcaggagatc   24180
gagaccatcc tggctaacac ggtgaaaccc cgtctctact aaaaatacta aaaattaacc   24240
gggtgtggtg gcgggcgcct gtaatcccag ctactcggga ggctgaggca ggagaatggc   24300
gtgaacccgg gaggcggagc ttgcagtgag ccgagatcgt gccactgcac tccagcctgg   24360
gcaacagagc gagactctgt ctcaaaataa ataaataaat aaataaataa ttgaaacatg   24420
cggtgcatgt gtttatttgc gatctgactt gtttggaaat atttgcatta tcttccttct   24480
agatttagag catcttgaca gtaggaacaa gtgttttgta caactttgta tgcttagtaa   24540
gttatcaatt aacttgtcgt ggccaggcgc agtggctcac gactgtaatc ccagcacttt   24600
gggaggccga ggcgggcaga tcacctgagg tcaggagttc gagaccagcg tggccaacgt   24660
ggtgaaaccc tgggtttgtt tgtttgttta tttatttatt tattttttgg agacggagtc   24720
tcgctctgtc gcccaggctg gagtgcagtg gcgtgatctc ggctcactgc aacctccgac   24780
tcccaggttc atgccattct cctgcctcag cctcccaagt agctgggact acaggagccc   24840
gccaccatgc ctggctaatt ttttattt tagtagagat ggggtttcgc cgtgttatct   24900
gggatggtct cgaactcctg actttgtgat ccgcccgcct cggcctccca agttctggg   24960 attacaggcg tgagccacca cacctggcct accctgtgtt tattacaaat acacaaattg   25020
gccatttgtg cgtggctcat ctacagtctc agtgactcag aaggctgagg caggagaatc   25080
tcttgaaccc gggaggcaga ggttgcagtg agcagagatc gtgccactgt acttcagcct   25140
gggtgacaga gtgagactgt gtctcaaaat aataataata atttgttgaa tatgtgactg   25200
ttggtttaat tttattttt atgagatgga gtctcactct gttgcccagg ttggagtaca   25260
gtggcgtgca gtggcgcaat cttagctcac tgcaacctcc gcctcctgtg ttcaggtgat   25320
tcagcctccc aagtacctga gactacagac gtgcactacc gtgcctgact aattttgta    25380 tttttagtag aaatggggtt tcaccatgtt ggtcagcctg gtctcaaact cctattctca   25440
agtgatccgc ctacctcgac cttccaaagt ggcggaatta taggtgtgag ccgtggtgcc   25500
cggccagact attggtttgg tttggtgtga tgttatgtta tgttatgtta tgttatgtta   25560
tgttatgtta tgttatgtta ttttaagaca gagtttgtct cttgtcgccc aggctggagt   25620
gcagcggcat gatctcggct tactgcaacc tccgcctccc aggttcaagt gattctcctg   25680
tcttagcctc ccaagtagct gggattacag gcgcccacca ccgtgcctgg ctaattttg    25740 tattttagt agagacaggg tttcaccatc ttggccaggc tgttctggaa ctcctgacct    25800
catgatccac ccgccttggc ctcccaaagt gctgggatta caggcgtgag ccactgcgcc   25860
```

```
tggctgacta ttggttttat tattaagcag tagtagttga ccctgtcatg tagaaagcat    25920
ggcatttata ggcataccac gtttaatttc ctcccctttt tttattttg gagtacctcc     25980 tgcttgtgag gcttgggaat acagtagtga ataagccaga tgaggtctct ctcttttgg     26040 agcttatgtg gtagtataga ctaggcagaa agttctcatt gcccctgcca ccttatggca    26100
ttgaggtgtt tgagatgctg atgtttactt ctgtctcata aaatcttgaa aggagttctt    26160
ttagatgaag aggaaaacaa aatcagaaga atgggcctgg gtcatgtctg taaacctccc    26220
cacgtcatgg ggaggctgaa atgggaaggg ccaggagttc aagaccaggc tgagaaacat    26280
aacaagaccc catctctaca aaaatatttt tttaattaat gggggatggc agcacacacc    26340
tgtagtcgca gctactacga ggctgaagcg agaggattgc ttgagctcag gagttaaaga    26400
ttgcaggagc tatgatcaca gcactgcgct ccagcccctc ttatcagcag tctggtatgt    26460
tgctaagggt cttgttcttt ttagtgcttc agggacagcc actggctatg cccagaaata    26520
agtatgtttg agaagctttc tgacctcagc ttgaaaaatt gattagggtc ataattaaaa    26580
agggagggaa acaggattga gtgaaccgga cgctaccgtg agtttattct cccagggcat    26640
acataatctc atgtgattac cacatagccc tgttagataa tctgttatcc tgtcctcatt    26700
ttacccatga ggaaatgaag gcccagagag gttaaatgac ctattcaaat tcactcagaa    26760
ggtggcagag atgagttact atcattgtat tttggatctc tggaaagaaa gaaaactagt    26820
gatggtatta aaaaatgtta ttaatagttt cttttaatca accaggaact tgagtcacta    26880
gcttctctgg gtgaaggact atacttcaac agtatgaaaa acggaaaaga aaatgaggaa    26940
ttttggctgg gcacagtggc tcacacctgt aattctagca ctttgggaag ccaagggagg    27000
agggtcgctt gagctcagga attcaagatc agcctaggca acatagtgag gccccatctc    27060
tacaaaaata aattagctgg gcatggtggt gcatgcgtat agtctcagct acttgggagg    27120
ctgactcagg agggtcactt aaacccagga attggaggtt gcagtgagct atgattgcgc    27180
cactgtatac catcccaggc gacagagtga gacccctatcc ccccaccgcc aaaaaaaaga    27240
aaagaaaatg aggaatttac atttgtgaca gatacggaat tcagggaatt tagttgttca    27300
tagtctataa atgctataag aagtctccat acctttttt ttttttttt tttttttgg      27360 agacagagtc ttgctctgtc gcccaggctg gagtgcagtg gtgcgatctt ggctcactac    27420
aagctctgcc tctcgggttc acgccattct cctgcctcca cctcccgagt agctgggact    27480
acaggtgccc gccaccacgc ccggctaatt ttttgtatt tttggtagag atgaggtttc     27540
actgtgttag ccacagatcc cgacctcatg atctgtctgc ctcagcctcc caaagtgctg    27600
ggattgcagg cttgaatcac cgcacccggc cggaagtctc catacttttt aacccaatct    27660
aaaatggtaa ggaaatatat aagaatgtct atttattatt aaatttttc tatataaaac    27720 atttcagaaa ataaagacta gcatttctga gccaagtggt agtagtggcc atttttctg     27780 gaaaaaaaaa aaaaagaaa gaaaaaacac atttagctat ctatgatgtg aaaagatgaa    27840
cattttattt aggtaataaa tgttatgtca taaaatacca tttattgtgt gcctattagg    27900
tttcaggaga gctgtgccaa gagcattact tgtatatctt ttaagcctta caacagccca    27960
gcctgtcagc ctggtagtgc catatctgtt ttacagatga ggaagtgatg gattggaaa    28020 attaaggaaa ttgcctttag gtcaaagaga taggaagtga caaagctgag attttaacc    28080 ttgtgagatt tcaaagtctt tgcttttaa taactgttcc attgcttcta atatagagat    28140
atgacaaaaa caagtaaaaa tcagtgaaga aggctgggag cagtcgctta tgcctgtaat    28200
cccagcagtt tgggaggccg aggcgtgtgg atcgcctgag gtcaggaatt tgagaccagc    28260
```

```
ctggccaaca tgacaaaact ccgtctctac taaaaataca aaaaagttag ccaggcgtgg   28320
tgacaagcac ctgtaatccc agctactcag taggctgagg caaggagaat cgcttgaacc   28380
tgggaggtgg aggttgcagt gagctgagat cgctccattg cactccagcg taggcaacaa   28440
agcaagactc cgtctcaaaa aataaataaa taaataaata aaaataataa caataatgaa   28500
gaaaacaatc cggtgattat tgtcagcaat aaaatttctt caatcaacca tgctttagtc   28560
ctggcagttc tctatcagtg agtttcaatc aaaaagtttg tttataattt ttttttttt   28620 aaaattttga aatttggaaa caacatcata aatgatggtt agttttctgc agctccctat   28680
tttggcagat agtctgttgt tactcataat taatttgaac taaaaagtag tgttgtacga   28740
tatcatgggc tgtgaatgtg tttgtgactt gatctgagaa cccacacacc acttaggatg   28800
cttctgtagg aaaattagag tatggaactc acttgcccac gctttccctg tctcagtcca   28860
tgttggtagg ctgcaaagtc tggggctaga aggacactga acaagacttc agcagtacat   28920
gttagtcttc cagagggaag gaatataata gttgagagaa taattccttt cctctgtgac   28980
tttaggcaaa ttcttggcta tgctgttatt tatttgggcc aaacaatatc aggaggttgt   29040 acatttatt cttaattact gcgatacatt aattttatcc atgggtttaa cctagcctac   29100
cttttgctgt tagacttcaa ctctacttgt gttgggttac ccctctgctt aaaaatcacc   29160
ctattcccaa gcctgaggga gtctaccttc aaagctttct atgacctaat ccaaggcctg   29220
tcaaacttcg taaagggcca gatagtaaat tgttttttt tttttgagat ggagttttgc   29280
tcttgtcacc caggctggag tgcaatggtg ccatcttggc tcactgcaac ctctgcctcc   29340
caggttcaag tgattctcct gcctcagcct ctcaagtagc tggggttata ggcatgtgcc   29400
accacgctcg gctaatttct ttgtatttag tagagatggg ggtttcacca ttttggtcag   29460
gctggtctcg aactcctgac ctcaggtgat ccacctgctg cggcctccca aagtgctggg   29520
attaccagtg tgaaccaccg tgcccagccc gatagtaaat attttaggct ttgcagtcca   29580
tatacagtcc cattttttg tgtatgtttg cacgttttct ttacatattt taaaagcccc   29640
tttttttttt ttttttgagac agagtcttgc tgtgttgctc aggctggagt gcagtggtgc   29700
aatcttggct cactgcaacc tctgcctcct gggttcaggc gattctcctg tctcagcttc   29760
ccgagtaact gggattacag gcacatgctg ccacgcccag ctaattttg tatttttagt   29820 aaagatgggg tttcgccaca ttggccaggc tggtctcctg atctcaggtg atctgcccac   29880
ctctgcctcc caaagtgctg ggattacagg tgtgagccac cgtgcctgac ctaaaagctc   29940
tttacagtgt aaaaaatatt ctgagcttta agccatgtga aaataggcca tgggcatttg   30000
ctgaccccta atagaactcc attttacctt tctgatcatg tttcccatta actcttcaaa   30060
aatatgacct ccatttaaat caagatggtc tccttcctca ctgcttgtgg aggtccagtg   30120
cccagtgtct gcctcttgct tgctcctcca tcattgttct gccattcgag atcctcatac   30180
ttacccttta agatctagcc caaatttttcc atgaaactaa ttctaataat taaaaacttc   30240
ctgtagaact taactttgtc tagtacaagt tagctttctt attcagtagt agcttactat   30300
aaattacaag aataaaaaga ttaccatttt ccctcacact gttttgtgga gaatgcctaa   30360
agttactttt tcttttaca ggtcagtatt cctatttggc atcctaatcc cctttcccaa   30420
atctgaattt tgggatttga agcttgcatt tgagattatg atttgtcttc cttgttgtac   30480
acaggagcag ggactttaca attagtattc gcatccctgc tccttcatac ttcgtgatgt   30540
aaggcaagtt attttcactt atgcttaagt ttcttcccct gtaaaaaggg gatggaagag   30600
```

```
gattaaatga attaaacatg taacacgctt aaagcaatgc ctggcaagta ataagtgctc    30660
agtaactttt agctgttctt attagcatgt ttggaaacca gtagaaacta caccagcaag    30720
ttaaggttga aaagtggtat tgatgggctt ggggtagtac agtatgaatg ctacagtttt    30780
agcgtttcat taagtttgta tattcattaa ttcattacac atttgatgct gtcagactag    30840
gacagagaca aagatgaatg aaacattatc tctgcttcca ggttacccag tgtagtagag    30900
aaggcaggca tgcagatagt ttaaattggt agcactggga ggggactgcc atgggtgggc    30960
agtgaagaaa aagggcttca aaataatgag agttgagatg gatcttcaag gaagataagc    31020
agttttcagt aaggccatga agagaggagg aagttccagg cgggaagagt ttgtgctaaa    31080
gtacagggat tgctatacac atggtgtatg tagaaaaaat ttggttcaca gtgtgataga    31140
agaattggag ggggtcctca ctgaaagtaa ggaaacacat ttggaagaat atgtttcagt    31200
tagaaaatga aatgagctta aagtaaacgc taataaggtt tttaaaatgt aaaatttcaa    31260
cgtatttaga aagagaacag ctggatgaat cttatgtacc tgtcactcag ctttagcagt    31320
tatcagtaaa tggccaacgt tgtttcagct atactcccct ctcctccact gatagtcttt    31380
tgaaggggaa tacaattgtt ttgtggcctc cagaaaggga taagtttatg agcaacgggt    31440
agatcgttgg gagagacttg agtttcctgt caggaagcat tcttggtgca taagtcagag    31500
gtgatatgaa tgccgtggaa gggggtggct tactgtctgg agaactcgag aagatgggaa    31560
tgggcactgt ccagtattgt ggctacttcc acacatggtt ctttaaattt aaaattatgt    31620
tgattaaaat ttaaatattt cagttcctca gccatactaa tcgtatttca agtgcttagc    31680
tgccacatgt gcctaatggc tgcaatattg acagcatga cataggacat cttcatcatt    31740
gtacaaagtt ctcttggaca gcatgggact agagccctaa gatccttttc tacctgagtt    31800
gtttggattt tttggtgtgt ctaggttgga tctagttgtt catggcttca tgaccaagcc    31860
ttttatccct ttctctagag ggactcaagg ggtaaaggca ctgaaggggt aaaacttcat    31920
atgaagagtg tggtggtggt ggtggtgttt taagacaggg tctcgctctg tcactcaggc    31980
tggagtccag tggcatgatc ctggctcact gcagcctcga cttcctgggc ttaagtgatc    32040
ctcccacctc agctcccaag taactggaac tgtaggcatg agccaccaca cctgcctaat    32100
ttttaaaact ttctgtagag acgagatttc gccatgttgt ccaggctggt ctcaaattcc    32160
tggactcacc ttggcctccc agagtgctgg gattgcaggt gtgggccact gcgactggcc    32220 tttttttttct cctttactac tctagtgtat gctggaatat gaggaaataa ttatattagc    32280
tagcagttat taaacactta ataacatacc aggcactgtt ttaagctatg cgatctgtat    32340
ggaatattac ttaatttcca caaccttatg aaaagatact atttttttc ttttgagaag    32400 gtactatttt catcttcatt tcatagatgt tgaaattgaa acacagagag ctgaagtcac    32460
aggattaagg ccacagagct gagaagtgat ggagccggaa tttgaaccca agcaattaat    32520
gctgatatta gttcttgtgt gaatggtaat tgttttgaaa caatgatcct agatgattat    32580
atgaccggat taatctggca gttgttctgt gtgaatttag agttgccttc ccacctcagt    32640
ttcctaaaaa caaacaaaa caaaacaaaa caaaaaaaac tctagcttca ctgtgtttgg    32700
gttgtcatgg cctaccccct cttgccacct catttgactc aacttttag ggagaaaata    32760 ttcaatacgt ggtataggat ttcccttct aataataatg taaacaacaa caagaagtct    32820
gaaattggaa gaacaaaatg actcacctaa gtgagttaac cttaagaggt ggaacttgat    32880
ttctagattt tagttaattg tctaactgat gtactaaata ttagttactt aagtattaaa    32940
acgggtagac ataatagttg gggagctgct gtagaggggg tagtttgaga aggcttcttt    33000
```

```
caggaggtga catttaagtt ggtaactaac aagaaagggg cagccatgtg aatagctgga    33060
gggaagagca ttcttacagt tttactggaa gggggttaga ggtatgtggt acccttatgc    33120
caaagaaaat tagttacttc tatacaacca gtctgattct agaaacctgg atcaatgaaa    33180
tattttgatt atataaaaaa atctgttacc caggtcttgt tgaaatagca ttagaaacta    33240
ctgaaggaca tatagaggag gagtgttgaa aaatggtgat ggatgagcag aatggtgaaa    33300
aataaaaaga catgaagctc tataattata ttgtatggtg acagtaccaa tagagattgc    33360
atgttttttc tccccagttt ttttttttgt tttgttttt gttttgaga cagagtctca     33420 ctgtgtcact caggctggag tgcattgtcg tgatattggc ttactgcaac ctctgcttcc    33480
tgggttcaag cgattctcct gcctcagcct cctgagtagc tgggattaca ggcatgtgcc    33540
accacgcccg gctaattttt gtattttat ttgagagggg atttcaccat gttggcaagg     33600
ctggtcttga gttcctgacc tcagataatc cacctgcctc agcctcccaa agtgccggga    33660
ttacaggtgt gagccactgc gcccggcctc ccccagttgt tgaaacaata atggaaggta    33720
attttattct tagattattt aatgtttttc agttatcagg atgtgttaga ttgtttgtgt    33780 atattgttttt gcttgttaat taagtaacac agtgaataag acagacaaac atacgaaaat   33840
gtacatttat tttattttt tgagacagtc tgttgcccag gctggagtgc agtggcccaa     33900
tctcggccca ctgcaacctc tgcctcctga gttgaagcga ttctcttgtg tcagcctcat    33960
gagtagctgg ggccatgggt gcacgccacc atacccggct aattttttata tttttagtag   34020 agatggggtt tcaccatatt ggccaggctg gtctcgaatt cctgacctca ggtgatctgc    34080
ccgccttggt ctcccaaagt gctgggacta caggcatgag ccactgtgcc aggccatttc    34140 attttttggaa cgttcttttt ttttttttgaa atggggtctc gctctgtctc ccaggctgga   34200
gtgcagtggc tcaatctcag cttactgcaa cctctgcctt ccgggttcaa gtgattctcc    34260
tgcctcagcc tcctgagtat ctgggactac aggtgcatgc caccacgcca ggctaatttt    34320
tgtattttta gtagagacgg ggtttcacca tattggtgag gctggtcttg aactcctggc    34380
ttcgtgatct gcccgcctca acttcgcaaa gtgctgggat tacaagtgtg agccaccacg    34440
cccggcctgt ttctggaata ttcataatct tttgttgtca tttcaacagt gctcacagca    34500
gcttcaccag gtgtagattc catcttaaga aaccactttc tttgcttatc catgagaagc    34560
aacacctcat ctattcaagt tttatcatga gattgcagca attcagttac atcttctgac    34620
cccacttcta attttagttc tcttgctttt ttaccacatc tgcagttact tgctctactg    34680
aagtcctgaa cccctcaaaa tcattcatga gtattagaag caatttcctg gttgggcacg    34740
gtggctcatg cctgtaatcc cagtactttg ggaggccaag gagggcggat cacctgaagt    34800
caggagttca agaccagtct ggcaaacgtg gtgaaacccc gtttctacta aaaatacaaa    34860
aattagcggg gatgtggtgg cgggcgccta atcccagc tacttgggag actgaggcag     34920
gagaatcgct tgaacctggg aggtggaggt tgcagtgagt tgagattgtg cccttgcact    34980
ccagcctggg caacaggagc gaaactctat cttaaaaaaa aaaaaaaaga aaagcaattt    35040
cctctaaaac tcctgttaat gttgatgttt taacctcctc ccatgctcat ggatggcatt    35100
ctcagtggca tctagaatgg tgaatacttt ttagaaagtt ttcaatttat tttgccatca    35160
gagaatggct atgaatggca gtagtagcct tacagaatgt atttcttttt tttttttct    35220 ttttttttga gatggagttt ttttgctctt tgtcacccag gctggagtgc agtggcatgc    35280
tatctcggct caccgcaacc tccgcctccc gggttcaagc aattctcctg cctcagcctc    35340
```

```
ctgagtagct gggattacag gcatgcacca ccatgcccac ctaattttgt attttagta    35400
gaggcgggt  ttctccatgt tggtcaggct ggtcttgaac tcccgatctc aggtgatctg   35460
cctgcctcgg ccttccgaag tgttgagatt acaggcgtga gccaccgcgc ccggccgtat   35520
ttcttaaata aaatggctta aacgtcaaaa ttatcccttg atccctgggc tatggactga   35580
ttcttgtgtt agcagttatg aaaacattta tgtccttgta cattcccatc atagcttttt   35640
gtcaatgaga agtaattttt tttttttttt tgagacagaa tctcactctg tttcccagcg   35700
tggagtgcag tggcatgatc tcagctcagt gcatcctaca actctgaggt tcaagcaatt   35760
ctcgtgcctc agcttactga gtagctggga ttacaggcgc ccaccaccac gtctggctaa   35820
tttttgtatt tttagtagag atggggtttc acgatgttgg ccaggctggg ctcgaactcc   35880
tggcttcaag tgatccacct gccttggcct cccaaagtgc tgggattgta ggtgtgagcc   35940
actatgcctg gcctaattgg cctaatttca atattgttat atctcaggga atagagaggc   36000
acgaggagaa agagagacaa gctgactgct ggttcgtgga gtagtcataa cacacaacat   36060
ttattaagat tgctgtctta tatggaccgt ttgtggtgcc ttaaaagaaa tcagggtaac   36120
atcaacgatt actgattaca gattactata acagatacaa taataattgt aaattattat   36180
ttacaattgt aaaatacaat cttttcttta ttatttacaa ttattgtaaa atacaatctg   36240
attacagatt actataacgt atacaataat agtggaaaag tttgaaaata ttgtgagatt   36300
tatgagaatg tgacacaggc gcaaagagag cacatgttac tggaaatacg gcactaatgg   36360
acttgcccga ctcggggttt ccacagacgg tcagcttgtc aaaaatgcag catctgtgaa   36420
tttcaataaa gcaaagcaga ataaaatgag gtatgcatgt attgccatca catgtacact   36480
agtaaaatac gttttttttt tcagtaggtg gatcaacctc aaattttaat ataaagcatt   36540
acttaaagga gaatatgggg acattcatga catttcttat atgtacataa aacttcatga   36600
aaataattta atgctatcca gcagtttatt ttagaagtac tggaggctag gcatggtgtc   36660
ttatgcctgt aatcccagca ctttgggagg ctgaggtagg aggatcactt gagttcagga   36720
gctggagacc agcttgggca atatagtgcg accccatctc tacaaaagag aaaagaagta   36780
ctggagtgtt gcagctctta cagaatttgt ctagcaggtt ttccagtctt taccagaaat   36840
gcccccatgc agaagtagta aatactgatt catgtaaaat aataaacaac tttatctttc   36900
agtttttaaa agacagggtc ttgtaacgtt gcccagactg gcctttaatt cctgggctca   36960
agcgatcctc tcacctgagc cttttgagta gctgagacta caggctgcac ctctgcacct   37020
ggctctgctt gattttaat tgttgtattg ctgttgcagc tatgtttttt tttttcttca   37080
gtgtgaggat gggcaaactt tttatgtaaa gtctcaggta ataagtattt taggctctag   37140
ggccatatag cttctctgtt gcatatcctt tttttttttt tccatttccc ctcaaattcc   37200
ttttaccata agcaactctt gaggaacata aaaatcattc ttagcccaga agccagacca   37260
aaacaggttg tgggctgtag tgtcctgacc cctgatttaa agattgatag ctttgaaatg   37320
gaaagtttta actttctttt tttttctttc ccttgttctg attgggctgt taattcatta   37380
ggtatttact cagtgtgtat catatgaggc atgattcctc tgctaatttt ggtagtggta   37440
gaaagatact tttgccaagc ttggttgtta ggttttcatt tgtccaagag ttcctgacca   37500
agtgtgaatg gatgttgaaa tcaaggtgtt tctttggcca cacaatgtgc ctttggggc    37560
tatatctatg tgcttctggt accttctttt aattttcaca aagacactgc ttgccgacca   37620
cactgttttg tctaatgtgg ggctatgacc ccctggaaga ggcatcattt tctgattttc   37680
acagaagcat aatatggtca ggtgatggtc ctgagtagtg ggtatatgac agatacacta   37740
```

```
gtaattataa tacagatcta aactggagag ttgaaaacag catcgtatat ttgattgaga   37800
taatcgaagg aagacttcct gaaaagatgg catttgagtt tcaaggctga gtaggattaa   37860
gtattattat ttaaaaaatg ccttggacaa tgcattaaat agagttaaca aatcacatca   37920
cttatagtct ccaattaaaa acattttact taaacataat tttagacttt tagaaaaatt   37980
gcaaagatat tataaagaat tctcctatat atctcacctg tattcttcaa gtaacatttt   38040
accatattca ccttaacatt ttctctgtat tggtaattgt atatgtaaga tttaatataa   38100
aataaaaatt cttattaaac atatgagaga catgatgcct ctttagccct aaatacttca   38160
acttgtatgt actaataaca agggcattct atttcaaaac cacagtacag ttgtcaaaat   38220
aaggaaatta ataattgtgt caaactgtta ttctgtttat agaccttcta atgtcccttta   38280 aaacaatcaa caaatcaaca ttttctggt caagaaccag taaatatgta tattctacat   38340
atatatatac acatatatat acacacatat attctacata tatgtggaa atacgtat    38400 ttactccctc tgtccaagaa ccaatccagg attgttacct tcggttatca tgtatctttg   38460
gtctccttta atccaaagca gtttctttgt cttttatgac ttgacactt tgaagattac    38520 aggttatttt gtagactgtc cctcaactag ggtttatctg aggttccctt atgattagat   38580
tcagatattt attttggca ggaatacaac agaaatgatt tgtgtgtttt tctcattgca    38640
tgatatcaga aagtgcattg tatatattta tcccattact ggggttgtta actttgatca   38700
cttggttaga gttgtgtcta ctaagtttct tcactataaa gttattttc acttggtcat    38760 ttcatcagta tcttgtgggg agttactttg tggttatata aatactctgt ttctactttc   38820
ccttactata tttagcttct gtggacactt tgcctgaaa cagttattta ctatggtgtt    38880
accaagtagt gatgcccttt tcttccatca ttctgtctac atttttttt ttttttttt    38940 tttttgaga tggagtttcg ctcttattgc ccaggctgga gtgcggtggc ctgatcttgg    39000
ctcactgcaa cctctgcctc ccgggttcaa gcagttctcc tgcgtcagcc tcccgagtag   39060
ctgggattac agacatgcgc caccactcct ggctaatttt gtatgttcag tagagacagg    39120 attttttccat gttggtcagg ctggtctcca actcccgacc tcaggtgatc cacccacctc   39180
agcctcccag agtgctagga ttacaggcgt gagctgccac accaggcctt ctttttctct    39240
tttaagagat agagtcctgc tttgtcacca aggctggagt gcagtggcat gatgatagtt    39300
cactgcagcc tcaaactcct gggctcaagt gaacctccca tctgtagctg ggactacagg   39360
cacctgcata acacctgact gttttttaaa actattttag agatggggtc ttgcgaagtt   39420
gctcaggatg gtcttgaact ccgggtctta agtggtcctt ctgcctcagc ctctggatta   39480
gttggcatta caggcatgag ccattgtacc tggcaagtgc atattttctt ttttttttt   39540 taaggtggag tctcgaggcc gggcgcagtg gctcacacct gtaatcccag cactttggaa   39600
ggccgaggtg ggtggatcaa gaggtcagga atcgagacc atcctggcta acatggtgaa    39660
accctgtctc tactaaaaat acaaaaaatt aactgggcat ggtggcacac gcctgtagtc    39720
ccagctactc gggaggctga ggcaggagaa ttgcttgaac ccaggaggtg gaggttgcag   39780
tgagtcaaga tcatgccact gcactccagc ctgagcgaca gaggtagact ctgtctcaaa    39840
aaaaacagaa agacggagtc ttgctctgtc acccaggctg cattgcagtg gcatgaactc    39900
cgcctcctga gttcaagcaa ttcttgtgcc tcagcctccc aagtagctgg gattacagac   39960
atgtgccacc acacgtggct aattttata gtttttagtag aggtggagtt tcaccatgtt   40020
ggctaggctg gtcttgaact cctgacttca ggtgatccac ccgccttggc ctcttgaagt   40080
```

```
ggtgggatta tgagtgtgag ccactgtgcc cagccaagtg agtatttgct tatgtagtat    40140
tttaatttta tgatttttt ttctttgaga cggaggtttg ctcttgttgc ccaagctgga    40200
gtacagtggt gccatctcgg ctcactgcag cctccacctc ctgggttcaa gccgttctcc    40260
tccctcagcc acctcctcct gaatagttgg gattataggc gcctgccacc atgcctggct    40320
aattttttgt atatctagta gtgatggagt ttgagcatgt tgccaggctg gtcttgaacc    40380
tctgacctca ggtgatccac ctgccttggc ctcccaaagt gctgggatta aggcatgagc    40440
caccatgccc ggccagagac tgttcattta ttttttttt ttgaggcgga gtctcgctgt    40500
attgcccagg ctggagtgca gtggcacaat ctcggctcac tgcaagctcc gcctcccaag    40560
ttcacaccat tgtcctgcct tagcctcctg agtagctggg actacaggtg cctgccacca    40620
cgcctggcta ttttgtttt tgtattttta gtagagatgg ggtttcagcc cgccttggcc    40680
tcctggagtg ctgggattac aggcgtgagt cagggcgcct ggccaatcat accttctttt    40740
actgcattaa ttatggtttt ctttcgttct taaaacatgt ttatagtgac cacttttgaa    40800
attcttatta agtcagacat ctggttatac aagcaatttc tattgcctac ttcttttcc    40860 agtgggtggg gttatacttt cctgtgtctt agcttgtcgt tttttttttt gttgttgaaa    40920
actggacatt ttaagtaatg tagtaactct ggatacctca ttagcctatg gttgggggtg    40980
gtggttgtta ctgttatttg cttatttgtc taatgactgg ctgaatgatt ttagtgttct    41040
atccttcttc cctccctgta cagtgtgaca cgtctgatgc tagttttctt gggatgcagc    41100
cttgggtatg cctaccatca ctctagaatc acagtgattt tggcatggct ttgtctcttt    41160
tcctgactgt acccagctgt taagctcacac taattactag gtgatgctgt gtagtcattt    41220
cttggtgtcc ttgggggatt ggtcccagga cccccccgtt ggatataaaa atttatggat    41280
gctctagtcc ctcataaaat ggcacagtat ttgcatatac cggtgcacat cctcctgtat    41340
gctttgtcat ttctagatta cttataatac ctaatatggt gtaaacacta ggtaaatagt    41400
tgttatatat tttttatttg tcttatttt attgtattta ttttaagtg ttttaatct    41460 cgagtgattg aatctgagga tgtgaaatct gcagatatgg agggcctgca ttgttttccg    41520
tggagctttg ggcctaaact gctccacaga ctgatctgat caaatttgcg cttcttgaa    41580 gggatagttt ctgagatcag tgtttgaaat ttgttccaat ccacagagga gtcctcccag    41640
ctctctttcc ctagttctgg ccaccaaact agacaactac aatttagcac ttatctccaa    41700
tgattctcct cctaccaagt gcctttgaaa gcatcattaa ctctttcata ccttgttgca    41760
aatgaaattt ctttgggaag agattgtgag ttttttttct cctaaattat ggtgcaatat    41820
aagtaatata ccatttaac aattttaagt gtattaagtg ttttttttt ttgtagtttt    41880 ttttttttg ttttttgaga tagtcttgct ctgtcgccca ggctggagtg cagtggcacg    41940
atctcggctc actggaacct ccacttcccg ggttcaagtg attctctggt ctcagcctcc    42000
ccaaatatct gggattacag gtgtgcacca ccacgcctgg ctaattttc tattttagt    42060 agaaacgggg tttcaccata ttggtcaggc tggtcttgaa cttctgagct cgtgatccac    42120
ccacctcggc ctcccaaagt gctgggatta caggccttag ccaccacacc tggcctatgc    42180
attgctttta tatgtatttt aaaattcata agttctcctc ctatgatgtt tttgtcccat    42240
gtgatttatt tgttaaaccg tcatctttgg ccgggcgtgg tagctcacgc ctgtaatccc    42300
agcactttgg gaggctgagg tgggtggatc acaaggttaa gagatcaaga ccatcctggc    42360
caacatggtg aaaccccgtc tctactaaga atacaaaaat tatctgggca tggtgacgcg    42420
tacctgtagt cctagctacc tgggaggcgg aggttgcagt gagccaagat cgtgccactg    42480
```

```
cactccagcc tggcgacaga gtgagactct gtctcagaaa aaaaaaaaaa caaaaaactg   42540
tcatttttta tgttgcattt actgcattct ggatttaaac tgtgaggaac ctcatggtat   42600
cagttaatat attcttccat cttaatgttt ctcgtaaact ggtagatctg taaacttgat   42660
taggtctatc ctattgtatc acatcagaag cagaaggtgc ttttttttt ttttaaggga   42720 aattgtgtga aagtagacag aatggtaaag tgaacccctg cacacctatc acccagcttt   42780
aatagttatc agctcatacc attcttgttt gatttacaac cccattcatt tctcccttct   42840
gtattattat tatttagtta attattttt gagacagggt tttgctctgt caccaatgct   42900
ggagtgcagt ggcataatca cagctcactg ctgtcttgac ctcctgggct caagtgatcc   42960
tcccacctca ccctaccaag tagcggggac cacaggcgtg tgccaccatg cctggctagt   43020
ttttattttt ttgtagaaac agggttttgc tttgttgccc agactgatct caaactccgg   43080
cactcaagtg atcctcctgc ctcagcctcc taaagtgctg ggattacaag catgagctac   43140
cacattcagc atgtaaattt ctttatatta atttgactgg cattttaagt cacacttgaa   43200
tttcatattt ggcaactatt aaaagcatag agtcctggat attagtgttt tgttaaacct   43260
gatctatcta atcataaata tacttaggtc taaaatatgc tcttggcctt tgtttattgc   43320
ggttcagtat ttgttactat attaaatagt aaaatatttg gtttgagata ctaatgaaaa   43380
gattaaaagt aaagcataac ttgaatggat acaaaagaa acaagaattt agacttcagt   43440
ggatttcaga gaatactgct tcgatatgct aacattcctg ttgggtgtcc aaccgtgtca   43500
tagatcagtg gaaattagtg gtttctgcac tttactgtac tgttttttta tatgataata   43560
ttttcctggt tgaatgattc gttcttttga gtaaactcca tggtcaaaca attactttt   43620 attagtcaaa gatgtaacca cataatcact aaaagaaca gtgtgactta tttaaagggg   43680
attatgtttt taagtctttt atatagcttt gtagggaggc catatgagtt taaggacagt   43740
tcgtggcatt tgttcaaggt tttgtaactt ggcatctcag cagccaccag gataccagat   43800
catcgttcta agtaagattt aggcatttta gccttcatgt acagactata agtacacccc   43860
cccacacccc taccaaaact gtaaattcaa atgatgtttg aaaaagcata gaattttgt   43920 taggcgaggt agtttattcc ttgtgataca gttccagaga ggcagcataa cctaggaatg   43980
aaaaacttag acgtggaatc agatacacct ggtttaaata ccagctctac tgctcatgaa   44040
ctggatgatt ttggtcaaga tacttgactg ctgaggttca gtttcctcac ctgtaaagta   44100
gaggtgatag attagacatg ttgcatgtga agtacttagt atggtgtctg gttttgtagt   44160
aagatctata aaagataaat tattagtcat attccttaga cttcaggaat ttatctctgt   44220
gccatgtttg aggcaaacag ttacagaatt agaatgttag aaatgaaagg aatcctagat   44280
gtcatttaat tcaagtccat tgtttttctgg atgagagaag aaagtgagga aaagtgacag   44340
agttggagac caagctagga ctggcctcag aatgttaaga gtactcttct agggatcgac   44400
cagtcgtgtt actagacttt ttggatctga attgtgcttt tccttgaatg ttttgaattt   44460
tggcttgagt gttgtgatta ttttattaaa atgagattcc agtcctattg tcatgactaa   44520
tgtttatgag aaatataaca tttcactta atgatgtttt ttaattattc taaggggcct   44580 aatcttttc agtggaataa gctttaggtt gtattatatt ctataattca cttgaaaata   44640
gaattcatct ttacttgaca gccaaatttt gtgtactgca tcttttctga gggagagagt   44700
tggcaaggaa aggcacttgt tacaacgatc cacacatata gacgcatatt atttagaaat   44760
gaaagtgctt tgaatgattt agcttatttt cagttttttt ttttctgcag ttgtaatcat   44820
```

```
atgacctgtt tttctttctt tttttttttt tgagacagag tcttgctctg tcaccccggc  44880
tggagtacaa tggggcggtc tcagctcact gcaacctcca cctcccaggt tcaggcgatt  44940
cttctgcctc agcctcccta gtagctggga ctacaggcgc atgccaccac acctggctaa  45000
tttttttatt cttagtagag atggggtttc actgtgttag ccaggatggt ctcgaactcc  45060
tgaccttgtg atctgcccac ctctgcctcc caaagtgctg ggattacagg catgagccac  45120
tgcgcccggc ccatatgacc tgttttctt ttatagatgg gggagaaata tgggaagtga  45180
cttggtgtca gtcatctgtg ttggttaaat caagaatata atccgtgttt gcttctgaa   45240 tagctcttta taacagtgat tggttacttt gggagtaaag attattattt agagacagag  45300
tcttgctttg tcgcccaggc tagactgcag tggaatgatc gtagcctact gcagcctcag  45360
actcctggac tctggtgatc ctgcctcagc ctcctgagta gctaggacta gaggtgcatg  45420
ccacatgcct ggctataatt attattaatt tacgtttagc attagttttt tcttccagt   45480 aggctatttt actttattta tttgattttg atgaagtttg attatttcta gtttgcttcc  45540
ttctatgacc cctacctgtt gtgggtctcc aggcaagcag tgcataggta gagccatcct  45600
taggtagcct ttagacttaa tattaggtga gctctcccca cagatagcct ctcctttatt  45660
tgaatggaat tatattttaa gtttggaaat attttttcagc ttatttagcc tgttgaattt  45720
aataaaaata atatttaatc ttttcagagg tcgaaacagt aacaaaggac tgcctcagtc  45780
tacggtgagt aactttaatg ttacttattg gggaaaatta gtagctaaaa catgatctct  45840
aaccacagac caaatgccaa ggcaaaagat tcccttcttt tgaattttgt catagataac  45900
ttgactgttt aagtatgtta ttagcctata tgtgttttt taatgactct gtataaaatg   45960
tacaattact tgttgtatta gtccattctt acactgctaa taagatata cctaagactg    46020 ggtaatttat aaaggaaaga ggtttaattg actcatgctc tgcattgctg gggaggcctc  46080
aggaaactta caatcatggt ggaaggggaa gcaaacacat ccttcttcac atagcgacag  46140
gagagagaag tgctgagcaa agcagggaaa gcccccttata aaaccatcag atctcctgag  46200
aactcactca ctatcatgag agcagcgtag gggaaactgc ccccatgatt cagttatctc  46260
cacctggtct tgcccttgac acacgagaat tattataatt aaagataaga tttgggtggg  46320
gacacagaac caaaccatat catttgtaaa tagtattttt gtcacgtgta ataacaagaa  46380
caagtcgctt gttcttttct aaatgactaa gtgcaaatct aagtgaaaaa cctccaaaag  46440
atacgtagaa caccaagagt ggagtctgca gagttcttta tgcttttat tttgaattaa   46500 tgtgcttttt ttctgctgct ttcatttttc tcctttggct ttctggtctt aaattttgga  46560
atgttatcaa tgaaattgaa ccggacatga agggcagaaa ctataagtcc cacatgatgg  46620
aagaaataaa tgaaagcta tcacaaattt ttgagacttt gcctttatta gattgtttta  46680
caagaatcag gaagatatac acgtatatgg tagtaatatg gagtagtgtg gttgatcaga  46740
cttaagcact gtcactgatg ctgatatgct gggagaacct agtcagggtt cttctatgaa  46800
ggtatgacct ggcttcctac cccatttatt tatacttcac ccttcttagg gtacatttct  46860
gtgagtttta acaattgcat acaatcagtg taactaccac cacaatcaag ttaatagaac  46920
agtttcattg cccaccaaaa tccctcaaat cacttttcag tgaaccctcc tctctctcca  46980
accattgatt tgtcttccat ccttacggtt tgtgtccttc ctcctctatg gaagtttact  47040
cttgcttttt tatgtcatgt ttagtcaaaa caccattagt tggtttgact gataacactt  47100
gaaaacctga ccttctgttc cttctgttct ctatggaagc aaaatattaa ataaacaaaa  47160 tcttcccctta atacatgtaa gatatcataa acctaactaa acattttgca acaaataata  47220
```

```
aacgttagct ttatatgcaa atgtaaatac aggctgagca tccctaatcg gaaatgctcc    47280
aaaatttcat attttgaatt agggatgttc aagcactaag tataatgcaa atatccccaa    47340
atccgaaaaa aatccgcagt ctaaaatact tctggtccca agcattttag atgaggaaga    47400
ttcagtttgt actaatttct aatagttttt tttttttttta atattccaga tttcttttga    47460
tggaatctat gcaaatatga ggatggttca tatacttaca tcagttgttg taagttatta    47520
gattattggg gataaactgc cttgggggta gaataaagta attccatgaa gttaaaatgt    47580
ggataaatga ttgtcaaagt aacattgctt agatcatgtt tagtcaggat gatttagaga    47640
aatagattag aactccttt atccagtcta atataattca ttgtaaaagt acagttggtc    47700
ctctgcatct gtgggttcca tattcatgga ttcagccaac cttggatcaa aaatatttgt    47760
taaaaaggcc aggcacagtg actcacgcct gtaatcccag cactttggga gtttgaggtg    47820
ggcagatggc ttgagctcac aagtttaaga ccagcctggg caacatggca gaactccgtc    47880
tctacaaaaa gtaaaaaaac tagccgaacg tggtggtacg tgcctgtagt cctagtgact    47940
tgggaggctg acgtgggagg attgtttgag cctgggaggt ggaggtttca ctgagctgag    48000
ataatgcccc tgcactcagc ctggtcaaca gtgccagaca gacccttct caaaaaaaaa    48060 aatttttttt tttttttttt tttttttttt ttttgagaaa aagaggcat ggttgcgtct    48120 gaaccaaaga tgtacggacg ttttcttgt cattattcct aaaacaatac agtatgacaa    48180
tttacatagc atttacatta tattaggtat tacaagtaat ttagggatag tttaaagtat    48240
ttgggagaat gtgcttagtt atatgcaaat actattacat tttatgtaag tgacttaagt    48300
attatgtaat tcggtatctg aaggaggtcc tggaaccagt cccctaccaa taacaacaga    48360
tagctgtatt cttgttaacc ctgctgtgtg tgtaaaataa tgttagtagt tgattgtctt    48420
ttgtacatta ttttgtcact taaaatagct ggggtcagaa atgtttgact tcagtattaa    48480
aattcgtact gcaaactctg agtagagcct cctgaagaat ttcaagagtt cagtgtattg    48540
ttaatgtttt gaaatttttt tattgttttg ttagtgaata cctaatattg aatgaagcct    48600
gatgaggtat aaaaagtaaa atgaaaacaa atatccctgg tgaccgggta gtatactgtt    48660
tctttgataa ataaattata tgtttttagg gctccaaatg tgaagtacaa gtgaaaaatg    48720
gaggtatata tgaaggagtt tttaaaactt acagtccgaa ggtaattttt actttttttc    48780
tttttcttac aaagtaaaag aacatttca tagtcagtgt tttacctagt ttttaaagcc    48840
actttgaatg attttacttc tcagtttcaa atactgatta ttttatagac tggtttgtgt    48900
aatcagagag gcttcttgat gtgtgtgctt attaaaatat ttcaaccatt tttaagcatt    48960
gtgagctaat agagggatgt ggtggtttgt tttttcctct taaaaattat tattaatgta    49020
cttaagacaa accatagaaa caaaaaacat ttagatatga ggattttaa atgatggaat    49080 ggataataga tcatatgcct gggaaaaagg gtatgattct cttgagatta ttttttgtcaa   49140 aggcatataa gaactggtac cttgatgagc taaagaattc ctaacaaatt ttattttgta   49200
aaggtttgga gtacttactt gtgttttttca ttttagtgtg atttggtact tgatgccgca   49260
catgagaaaa gtacagaatc cagttcgggg ccgaaacgtg aagaaataat ggagagtatt   49320
ttgttcaaat gttcagactt tgttgtggta cagtttaaag atatgactc cagttatgca   49380 aaaagaggtg ggtttgatt tcctaaaatat gcctcatggt ttattagatt tattcaagca   49440
aagattttca cagtgatctt acaaactttt tttaaagaaa tatctgggct gggtatggcg   49500
gctcattcct gtaatcttag cacttaggga ggctgaggcg ggtggatcac ctgaggtcag   49560
```

```
gagttcgaga ccagcctggc caacatggcg aaaccccgtc tctactaaaa atacaaaaat    49620
ttattttttgt gtgtggtggc gtgcgcctat agtcctagct actagggagg ctgagacaga    49680
attgcttgaa cccaggaggc agaggttgca gtgagctgat accgcaccac tgcactccag    49740
cctgggtgac agagcaagac tccgtttcaa aaaaaaaag aaagaaaaaa gaaatatcta    49800
cttctagaa tagcccaagt aaggtaattt tttagaaaaa tgagaatgtt aatgcatttt    49860
tgttggaaaa caattagaac tttagagaaa aattaaatag agtttttgtg atctcttaaa    49920
aaattagttt gtaaagcatt ttctacagtt ttgtggtcaa gaatgctact gattatattc    49980
aactgaaaat ttcttgtccc atttggccta caatgcttta gtttataagt gggcatgtgg    50040
caaatctgga aagaaatcaa agtataaggc taaggaagaa aggtagagaa cggttggtag    50100
aaaacaattg tctaatgaaa atgaaaaagg gtgaagaagt agaacatacg tattttaaaa    50160
atattcagag tatgagacaa ggttttgaga atttaaaagc gattatgtag ttatattaaa    50220
aatttagtct ctttttaagt gtccattgat gaacaaagtg ggaattcctg ttactcattt    50280
gcaaggcatt attgagtgtt cagtaacacg ttgcaaggca cttctgggca atcctgaact    50340
tggttctcaa attctttttt tttttttttt tgagacggag tcttgttctg tcccctgggt    50400
ggagtgcagt ggcacgatct cggctcactg cagcctctgc ctcccaggtt caagcgattc    50460
tcctgcctca gcctcctgag tagctgggac tacaggcgtg tgccaccaca ccaagctaat    50520
ttttgtattt tttgtagaga cagggtttca ccatgttggc caggatggtc tcgattgttt    50580
gacctcgtga tccgcccgcc tcggcctccc aaagtgctgg aattacaggc atgagccact    50640
gcacccagcc ggttctaaaa ttcttttatt tatttgtata tgccaaattc tgtagtgaaa    50700
tacgtaattc tgttgtaaat tgtagttcag tacaatttga ttttcactat tcaaatctat    50760
accaaaagct gtttttattg ttgggctgat tcttctacac tgttacttgg aaataataat    50820
ataccaggat tctttctctt agacttagga gtctttctct ttgcttgctt tttcagaggc    50880
taacagtact gggtattctt taactgtctt gatatgctga tgaaagcaca gtgttctgtt    50940
tttgaatctt ctcaaatgtc cttgtctttg attcacaact ttttgtctta agaggccttc    51000
agcatcccat acaaggaaac aagtctttt ttagctgcta cctttggagt tgattttgtt    51060
tatgtctagg agcactaaat tatttatact tatactattg aaatattcct ctgttataaa    51120
ttcaaaaatt gactttggaa gataaaattt tagttgaatt taatacatag cactctggaa    51180
agagtattgg ccacaacaaa aaaaaaggtt ccctactcta ttggatacca ggtcatttaa    51240
cagccattta cggtatgcat tgtctttttg tttttatgat gaattgatat ttcccaaatg    51300
tggaagagtg aatattactt tgagatgttt gtgatagtcc attccttgct cctcttcaaa    51360
attaatgtca ttaaatttt attactttat tagatcttca tttctcagat aattttagtt    51420
cattatagaa aggcaagaaa atacagatca gagtgacaac tttgaaaatc tcactctact    51480
cataagggga tgggtgtatt ttgctatata ttacaaaatt agttttcttg atgaggacat    51540
ccactattgg agtaatttca ggtatcttat tttttctttt ctctctcttt ttttttttt    51600
ttttggagac ggagtttcgc tctgttgccc aggctggagt gcagtggcct gatctcggct    51660
caccgcaacc tctgcctcct gggttcaagc gattctcttg cctcagcctc ccgagtagct    51720
ggttactgag gcatgtgcca ccatgcccgg ctaattttg tatttttagt agagacgggg    51780
tttcactatg ttggccaggc tggtcttgaa ctcctgacct tgtgatcctc tgccttggc    51840
ctcccagagt gctgggatta taggcgtgag ccaccacgcc tggcaggta tcttatttca    51900
aaacttacag tggtttagtg aattatacaa ttgcgtccag tgcgtagtat cctgaaaata    51960
```

```
gtattaagtc atgtgtttag gacatcaggt ctcttaagct aagactatcc aggcagaaat    52020
tgccctcttc tataaaagaa gaaaagtatt aattaggaag tactatcagt atggagaaaa    52080
ccattttaga attattaatt ggcatggttt ccttctttt tttttttattt cgagatggag    52140 tctcactcta tttcccaggc tggagtgcag tggtgcgatc tcggctcact gcaacctctg    52200
cctcctgggt ttaagcgatt ctcctgcctc agcctcccga gtagctggga ttataggcac    52260
ataccaccat gccctgctaa ttttttttt tgtttgtatt cttagtacag actgggtttc    52320
accatgttgg ccaggccgca tggttttcct taataacaaa attaaggcat ttattactgc    52380
atctagattt tttttatttt ttattagaga cttactcaga ttactcccaa agtaaaggaa    52440
ggtatggttt aatcaatgct tcttaatgct gggttcacgt ttagtcacct ggggagtttt    52500
taaaaatgtt ctcacttcta gggatcctgg tttaattata attagcctgg gtgaggctct    52560
ggacagtcag ggtgtgagct atgggtttca tgtgatgaga tcccaggagt ggctctgttc    52620
tgtggccttg agaatttgtg ctttctaggc caggtgcggt ggctcactcc tgtaatctca    52680
ctttgggaga ccaaggtggg cagatcattt gaggtcagga gttcgagacc agcctggcca    52740
acatgttgaa accccgtctt tactaaaaaa gtaaaaaatt agccgggcgt gatggcacat    52800
gtctataatc ccagctactt ggggagaggc tgaggcagaa gaatcgcttg aacccgggag    52860
gcagagattg cgagatcatg ccactgcact ccagcctggg caacagaata aaaaagaat    52920 ttgtgcttta ttttcttgcc tcacagtccc ctttctgtct cagaattggc aactgcctga    52980
aatagtctct gctgttatca tttgatagta cttttccaca tcttgaatgg atagatagag    53040
tgttttttat aatagaagtg gatgaatgat tagagtatac taatatgaca ttgtattttc    53100
ctaaaagata tgaattgatt tcatttctga gcttttataa ttctcttctg taatagtctg    53160
tcaaattatt aaggttgata atattaacta aaatttgagt gcatattcta tgtgccagac    53220
tctgtgctaa cagatttacc tacatttgtt cacataatca tcacaagttg tttctgtagt    53280
agatacagct attatccacg tcatagatga ggaaacaggc atatttagga aacttgctaa    53340
agtgaggaca caaatctagc ttttctactc taactcatgt tcttaacatt atactgcagt    53400
gacataaatt atgtggtttg gtttgttgtt tatctcagtt gtcataagtc gaattaatgt    53460
ttgtttgttt gttttgagac agagtcttgc tctgtcgccc aggctgggta cagtggcgtg    53520
atcttggcgc actgcaacct ccacctcctg ggttcaagca gttatcttgc ttcagcctcc    53580
ctaataactg ggattacagg cacgtaccac cacacccggg taattttgt attttagta    53640 gagatggggt tttaccatgt tggccaggct gatttcaagc tcctgacctt aggtgatcca    53700
cccacctggg cctcccaaat tgctgggatt gtaggcatga accactgtgc ccagccagta    53760
agttccatgt tgttaaagg atttctccac aaataaagct aaaagtaaaa aaaaaaaaa    53820 aaaaaaaaa ttctcaagca atataagatg cagactatta tgttgttcaa gttttttttt    53880 tttttttta atctttggct ttattttgg ggaaacctttt ttttcttttt ttgttttcct    53940
tgggacggag ttttgctctt gtcgcccagg ctggagtgca atggtgcaat cttcgctcac    54000
tgcaacctcc gccttctggg ttcaagcgat tctcctatct cagcctcccg agtagctggg    54060
attacaggca tgtgccacca tgcccggcta actttgtatt tttagtagag actgggtttc    54120
tccacgttgg tcaggctggt cttgaactcc tgacctcagg tgatccacct gcctaggcct    54180
cccaaagtgc tgggatcaca agcgtgagcc accgcgccca gccagggaaa cctttatttt    54240
gaggcggagt ctcgctctgt cacccaggct ggagtgcagt ggcgtgatct cagctcactg    54300
```

-continued

```
caacctctgc ttcctaggtt caagcaattc ttctgcctaa gcctcccgag gagctgggat    54360
tataggcgtc tgccaccatg cccagctaat ttttatattt ttagtagaga cggggtttca    54420
ccatattggc caggctcttc tcaaattcct gacctcatga tccacccacc ttggcctccc    54480
aaagtgctag gattacaggc gtgagccacc acactcggct gctggggaaa ccttttaaca    54540
tgagtaaggt cagtgtgact tttaagttct tgatgctaac atcattgatt tcaataaagt    54600
ttaaaagtta tattcatgca tatatgcaaa tgaataaaag gctttgaaat agtgacttct    54660
tacggtacag tgaataagtt tcctttggtc tcttgaatgt tatacatgtt ccagtttgat    54720
ttactgagaa actgaaagta cctttacgtc atatgagctg tgagtcacct tggcacattc    54780
ataattagaa gagaccatca gattatcatt ggaaaatcag tttgtattta tcctttattt    54840
gaattccagt gcagacagat ctgaggttct cttcattttg ctaaaacttc ttagggcctt    54900
cagtcgcttt tggctctgta ttcgtgtatc tttggaattg tcctgttatc tctgcttgtt    54960
ttttacttga ttttccatcc atttccagta ttcctttctc ctctattttt ttccttcatt    55020
ttctttctgc tcttcctgtt gcgccattat tcatgttttc ctctttactc caactcaact    55080
atggctttac ttctgtttcc ttattccatt gttcctcata cttttttccta ctgcttcatt    55140 ttctttgcag tattctcagc ctagatgata ggggtcagca aatctgctca tcagtaaata    55200
aattttattg tagcatagct atgcccatgc gtttgtgcat tgtctatggc tgttttgatg    55260
gctgtagcca tagagttgag tagttgtagc tgactgtagg acttgcaaag ccagaaaatt    55320
tgactgtctc tttacagaaa agtttgccag ctcttggcct aaatcatatt ttccgctgca    55380
tttagggctt tttaggactg atcaaaaata catgctatac tggctttggt gaagtaacag    55440
aatgtgctct gtccttaaa cttacaacta attgcatgct ttgattctaa tactgtataa    55500
tatcctgcga ttcttattca tgaccattct aattggattt agtctgaaga attacttttg    55560
cttaacagat tctttgtcac atttagtgaa aaatcataaa aggggaaggt tggttaatgg    55620
aaaagatctc catcaactaa ccactacctt ccttatctac aaatttatct tcttcctccg    55680
tgccatcttt tttttttttt ttttcagatg atcttgctct gttgcccagg ctggagtgca    55740
gtgatgcaat cacagctcac tgcagcctcg acttcccagg ctcaggtgat cctctcacct    55800
caacctccta cataactggg actgtatgtg cacatcacta tgcctgacta attttttata    55860
tttatatttt ttgtagagat gggtttccc tgtattgcac aggctggtct caaactgctg    55920
ggcctaagag tcttcccacc ttggcctccc aaagtcctgg gattacatga gtcaccgcac    55980
ccggcctcat tattatttt cctctggttt tagtagagag gattttttaag ccaacttcaa    56040 tcatgccctt gactctctcc cttctactta cctccttgtt ctcttttttct tttttctttt    56100 ttttagatgg agtctcggtc tgtcacccag gctgaagtgc agtggcgtga tttcagctca    56160
ctgcagcctc agcctcctga gtagctgggg ctataggtgc ctgccaccac gcccggctaa    56220
tttttgtatt tttagtagag atggggtttc accatgttgg ccaggctggt ctcgaactcc    56280
tgacctcaag tgatcacctg cctcagcctc ccaaagtgct gggattacag gcgtgagcca    56340
ccacgcctgg ccatcttttt ttttctcctt gctctttat accacttctc tgtttctggg    56400
ctcttcaaca tctgccttc tagttaatct ttccctttag catgaaaacc tattcacttc    56460
ctgctcatcc taaaaaggat tctttttttgt tttgttttgt tttgttttt gagacagagt    56520 ctcgctcttg cccaggctgg agtgcagtgg cactatcttg gctcactgca agctccgcct    56580
cccgggttca cgccattctc ctgcctcagc ctcccgagta gctgggacta caggcacctg    56640
ccaccacgcc cagctaaatt tttgtatttt tagtagagat ggggtttcac cgtgttagct    56700
```

```
aggatggtct cgatctcctg accttgtgat ccatctgcct cggcctccca aagtgctggg    56760
attacaggca tgagccaccg cactgggccc aaaaggattc tttttaatcc tgaattcttc    56820
tagccattat cctgcctaag gctacgatta acctctaact gccaggtcct ttggaatctt    56880
tttctgtctt tattgctgca cttgaatgtt ggtttcaccc tccttcagaa tttcctcttc    56940 tgtattttt atgtttattg atcattcctt ccctgcctca ttcctgggct tcttttcctt    57000
cacacacccc ttagatgtgt gtccccagtg tttgtttctt tgcctgctgc tcttgccaca    57060
tgacacacac tgccagctac cacacacaag ttccctccta tcatgtgtgt atcattgccc    57120
ttataccatg ttgtattaaa attatatgct tgtctcccct gttacagttt gagctctttg    57180
tgctccaagt aaagacagtg atactgtctt tattatttat tctcatggtc tagtatagtg    57240
ctttggcaca tagtacaggc tcaatataaa tgtgtttgaa taaatgaaat tcagtgcctt    57300
aatacacttt tgtagaagca ttattttatg gaaagaatga aaaagctgta agtggtctta    57360
catatatagt catccagcag atacttagag agctctggga tgtgttcctt gctgtgcttg    57420
ttgctatgga cagtacggag aaatacaaga atctattttg ggtcccttt gagaacctag    57480 tgaaactgtg tacctagtga aactgtatac cctcaccct gaaaaattta cacacatgta    57540
gattttacat gtaattcttt taaaaattaa ttttttttct ttttttaaa gaaacagggt    57600 catgctctgt cactcaggct ggaatgcagt ggtgtgatca tggcttactg tagcctcgac    57660
ctcctggctc aagcgactct cccacctcag cctcccaagt agctgggct acaggtgcac    57720 gccgctatgc ccggctaatt tttaaaaata ttttatagac actggttctc actatgtttc    57780
ccaggctggc ctttacctcc tgggttcaag caatcctcta ccttggcctt caaaagtgat    57840
gggattatag gtgcaagcca ctgtgcccac gctaatgtaa tttcatggtg ttcacagttt    57900
cttcagggag ttcatatacg ccatgtactc tattctaagc attttagag ttagagatag    57960 caaagcacgt gaataaattc aagaaaaatg gaatgttgta ctgcatgaca ttgaatatca    58020
aatggagtca gcgatgcaaa taattgtcta gattttacaa aaaaaattag cctggtgtgc    58080
tggtgtgcgc ctctaatccc agctactcgg gaggctgaga caggagaatc atttgaaccc    58140
agaaggtgga ggttgcaatg agctgagatc gtaccactgc actccagcct gagtgacaga    58200
gcgagactcc atctcaaaaa taaaaaataa aagaattgtg tagattttag tagttggaag    58260
aagttggagt gttaatgtgt aattagagaa cagtgagaaa taaaattcta cagattgttt    58320
tattctggtg tgctgttgtg ttctcatatg gttgtctttt tggtcttgat agtgtatcag    58380
taacagagta cgagtaacaa acagggatct cttctgaacg gcgtgacatt agaaaagctg    58440
tttacggcct caactttgct gtggtttatt aagacacaga tatgtgttca ttctggggcc    58500
aagcagtaac tggagagtgg cacttattga ggccagtatg gaggcagtac agagattatt    58560
gagattaaaa gaaagaaaca ggtggaacgg atctatgtaa tggaaagcta aacagaatag    58620
ttcgtggtac acagtagaaa agcattacat gtttattaag atatggtcat cttccattta    58680
ttaaagttac atgttttata attttagag tatatagaaa ttctctaccc tatcatgttt    58740
gccaaagtca gaacaataac ttcatttatt aaatataaaa aaataaaaa cctctagcat    58800 aaaatagaat tttatttgga caaacgataa aaaaatactg tgtggtacta gtaagagtaa    58860
ggttgattca agatacatgg gagcagaatc caaagtgtag aaataggcca ggtgcagtgg    58920
ctcatgcctg taatttcaac acttttggag gctgaggcgg gaggatgagt tcaggagttc    58980
aagactcgcc ttggcaactt ggcaaaaccc catctctaca aaagtacaa aaattagccg    59040
```

```
ggtgtggtgg tgtactcctg taaacccagc tacttggtgg gctgaggtga gaggttcact    59100
tgcagccagt aagtcaaggc tgcagtgagc tgtggttatg ccacggcact ccagctgggt    59160
gacaagcaag accttgtctc aaaaacaaac cagccaggcg tggcggatca cctgaggtaa    59220
ggagttggag accagcctgg ccgacatggc tctactaaaa atacaaaaat tagctgggcg    59280
aggtgacggg cacctgtaat cccagctact tgggaggctg aggcaggaga atcgcttgaa    59340
tccaggagac ggagtttgca atgagccgag atggtggtgc tgcactccag cctgggtgac    59400
agagccagac tctgtctcaa aaacaaaaat aagcatagga catggggata aattgaagat    59460
ttatgaagac acagctgaag gagacataaa agtagatttg gctaaatgga aacatgccat    59520
actttgaatg gaattattta atactacaac gttgtcaatt ttcctcaaat aaatctctaa    59580
agataatata ttcagttttg gccgggcacg ttggctcacg cctgtaatcc cagcactttg    59640
gaaggctgag gtgggccgat cacttgagga cgggagtttg agaccagcct ggccaacatg    59700
gtgaaaccct gtctctacta aaaatacaaa aatcatctgg acatggtggc aggtaccagc    59760
tacttgggaa gctgaggcag gagaattact cgaaccccgt aggtgaggt tgcagtgagc    59820 tgagattgca ctccagccgg gtgactccat ctcaaaaaaa aaaaaatttt tataatatat    59880
atatatatat ccgtttttgt agaaattgac aaaatgattc taaagcttat tagattatgt    59940
gtattaacag aagaactttg gaatttttt tccacaagag tcataaagga ggacttgccc    60000
tacaaaatat gtcagaatta aaacataact tgtcagctgg gtgcggtggc tcacgcctat    60060
aattccagca ctttgggagg ctgaggcagg cagatcatga ccagcctgac caacatggag    60120
aaaccccgtc tctactaaaa atacaaaatt agccggtcat ggtggcgcat acctgtagtc    60180
ccagctactc gggaggctga ggcaggagaa tcgcttgaac tcgggaggtg gaggttgcag    60240
tgagccgaga tcgcgccatt gcactccagc ctgggcaaca agagtaaaac tctgtttcaa    60300 aaaaaaaaa aaaaaaaaa gaattataac tgtcacagtg gctacgtatg gagcatccaa    60360
aactgaattt atgtgggtat tttattaata tgcaatatag cactttaatt ctggaggaaa    60420
ggtggattat tcagtaaatg attctgggac attggggaca aattagatac ctacttcaca    60480
ctgataaata aaaccaaata gattaatgag aaaactgtga ttaaacaaaa caacacccag    60540
actacactgg agcaaatctg tgaatttgtt taattttgag tggagaagga ctttataagc    60600
atgactacca gagcaaaaaa atcatgaagt aaaagatcga tacctttgat tataaagaga    60660
ttaaagattt aggccgggtg tggtgctcac gcttgtaatc ccagcacttt gggaggccaa    60720
agcgggtgga tcacttgagg tcaggagttt gagaccaacc tggtcaacct ggtgaaaccc    60780
catctctact aaaaatacaa aaaattagt caggcatggt agcacatgcc tgtaatccca    60840
gctactcagg aggctaaggc aggagaattg cttgaatttg gaagtggag gttgcagtga    60900 gccgagattg tgccacatca ctccagcttg gcgacagag tgactccatc tcaaaaaaaa    60960
aaaaaaaaaa gacttagacg tgtccaaaag taccatacat ttaaaaagac atgccacaaa    61020
ctgggaaaag tagaaaaata gttttaaaaa tgaccagtga atgtatgaaa aggtggccct    61080
cctcacttgt aatgatttaa gaaatgcagt ttatttttat tttattgtat ttttaaagaa    61140 attcagttttt aaagcagtgg aatatgattg tctatcagct tgcgctgaat ggtaaatgtg    61200
agaaagatta ctactactta gtggtactga gggagttgca aaacacttaa cactgctagt    61260
gggatggttt aagtaaaaca agtagcattc ttaaactctc tattaggtaa agaataggta    61320
agtaatgcat atgtttccag gacattttca gtaagactgt ttactgatag ggttgtgtaa    61380
tgctaatata cttactatct agttttagta ttatttttttt ctcttgtctt ggatggtttc    61440
```

```
aatggagtct tatgcatgca gatatattaa aactagtaat aaagcaagag aaggaatgtg  61500
gataaattat ctctaatttc tattttgttc tatttctatt tcatactcct gggaaagaat  61560
attaagtggg catgtgtact tgaacagttg ttctgttttt tattagaaaa gaatccgaat  61620
ctataaaatg ttttacatat ttgccaggga aacagaaaag atatttgtac agctgtaaga  61680
attggaatta atttcatttt actgactttt ccttaaccta attctgaaca cttttgccat  61740
aggtttgaga ataagttgtt ataaaatgac tactattctt cactaatagt attggcattt  61800
caattcctaa attctgtttt ttgattcttg aacatttctg aatttacttt ttttgtctta  61860
gttcttctac agaatcattt tcttcttttt tcttttttta tttttatttt ttattttga  61920 gacagagtct tgctctgttg cccaggctgg agtgcagtag cgcgatctcg gctcactgca  61980
agctccgcct cccgggttca tgccatttc tcctgcctca gcctcccggg tagctgggac  62040
tagaggtacc cgccacagcg cccggctaat ttttttgtatt tttagtagag acggggtttc  62100
accgtgttag ccaaggtggt ctcaatctcc tgacctcgtg atccatccgc ctcggcctcc  62160
caaagtgctg ggattacagg catgagccat cgcacccggc cttcttttt tctttctctt  62220 taacttctga gctgaaaata gtacctttta taaagaagtg ctcaaacgat gattggactg  62280
atttctcctt atttctctct ttctctctgt ctctttcact ctcttttag aatttttctt  62340 ttttaagtag agacgaggtc ccactatgtt gcccaggctg tcttgaactc ctgagcccaa  62400
gcaatcctct ttgcctcagc ctcccaaagt gctcggatta caggcttaag ctatcacacc  62460
aggcctaggc taatttcata ttttgagatg cacaaattt ctttcaggta gctagctttt  62520
cctcctcctc cccacttaaa atagatcctg atccagaagc ctaatggaga aaatgaaaac  62580
agaatgttca cccataaaca gtatctttgt attggaatct tttctaaaac ttcttttgat  62640 cttttagga gatagtgtgg gaatcagcaa tctagtatta cgtacgtgga atctgtcacc  62700
ttgttttttt aaatacagca aacctcatga agtgaattc catatttttt cttgttcttg  62760
ttagttttgc accactcagg ctttgctgta gaatttgatg tatatttgat tctgtagagc  62820
atgggctatt gatcttcact cagctttcag aggaatctga ttagtaagtt tgagttttt  62880 attatttttt agttgatttt gaagtaaaat acagcaccat tttaactgat accatttcta  62940
aacaattttc agttcaaatt ttaagttagc taatttagag cttaagaaaa ttgctttaaa  63000
aacataaaat tactggctgg gtacagtggc tcattcctgt aatctcagca ctttgggagg  63060
ccaaggcaga tgaattgctt gagcccagta gttcaagacc agcctgggca atatggtgga  63120
accccgtttc tacaaaaaaa atacaaaaag tagccagaca cggtggtatg tacctgtagt  63180
cccagctatt cgggtggcag aggtgagagg atcatctgag cgcagggaga ttgaggctgc  63240
agtgagccaa gtgagaccct ggtttcaaaa aaaaaaaggt tactaattgc agtgcctttt  63300
atcttattta atgggcttag tcaaactaag atgatgtatt ttatcttata aatgttttcc  63360
cttgaatttt aactgaagaa tccaatttgt acctctcaca aacagaatgt attagtaagg  63420
aaaataaata ctgctttta ttacttaaat aggatatatt tttctcttag ggattttttt  63480 tctatttat ctcactttat cgtagtgcta gaaaatttaa tcattcattt gagataggga  63540
gaaaattagg tttttttttt tcttctattt tgagacaggg tctcatttg ttgtccaggc  63600 tggagtgcag tggcgccatc gtagctcacc ataacctcaa actcatgggt tcaggtgatt  63660
caccttagcc tcctgattaa gctgggactg cagatgtgta tcaccactcc tggctaattt  63720
ttgttgttat ttttgtttg atgaggtctc attatgttgc ccaggctggt ctcaaactct  63780
```

```
gggcctcaaa tgatcctcct gccccagcct cccaaagtgc tgggattaca ggcatgaacc    63840
tctgctccca gcccattttt taaaatatat tcacagcatt gtgcaaccat cactacaatc    63900
aatttacatt ttcatcaccc tgaaaagaaa ctctgaaccc cttagcagtt cctctctgtt    63960
tgtttcaatt ttccccagct ccaggcaact attgatttat tgtcttcata ggtttgccca    64020
ttctggacat tgcgtattaa tggaatcata taatatatag cctttttttt tctttttttt    64080
ttttgaaaca gagtctcact gtgtcgccca ggctggagcg cagtggcatg attgcagctc    64140
actgcatcct ctgcctccca ggttgaagcg attctcctgc ctcagcctct tgagtagctg    64200
ggactatagg cgcctgccac cacacctact aattttatat ttttagtaaa gacggggttg    64260
caccatgttg gccaggctgg tctcgaattc ctgacctcaa gtgatctgcc cacctcggac    64320
tcccaaagtg ctgggattgc agccatgagc caccgcatct ggccatatat attatgatag    64380
gcttgtttca cttagtatgt ttcttccatg ctgtagcatg tattagtact tctttctttt    64440
tcatggccaa atattccatt atacagttac acagtacac tacattttgt ttattcatca     64500
gttggtggac attttcattg tttccacctt ttgatttata cataatcctg ctgcgaacag    64560 tgactttaa agttttgtg tgggccgggt gtggtggctc atgcctctgt aatcccagca      64620
ctttgggagg ctggggctgg cagatcattt gaggccggga gttcgagacc agcctgccca    64680
acatggtgaa accctgtctc tactaaaaat acaaaaatga gctgggtgtg gtggcgtgca    64740
cctgtaatct cagctactag ggaggctgag gcagagaatc acttgaagct gggaagccga    64800
ggctacagtg agccgagatc acgccactgc actccagcct gggtgacaga gtgaaacttc    64860
atctcaaaaa aaaaaaaaa aaaaaaaac tgcgtgtgga cataggtttt caattctcat      64920
gggggtgtgt gtgtatgcat actcatacat acatacacat acctgcaaga taattgctgg    64980
ctcgtatgct aaatctatgt tgaaccttt acataactgt tgggctgttt tgttttcttt     65040
ttattatttt ttgaaaatag agttggggtc tcactgttgc acaggctgat ttcctgggca    65100
tagtggctgt atcattttac aatcctacat agctgtttcc aacgtagctg tatcatttta    65160
caatcctact agcagtgtct gaggtttctt atgttttca catcctcacc agcatttgtt     65220
attgtctgtc tctttgatta tacccatcct agtgggagag taagaagtag tatctcactg    65280 tagattttt ttttctgttt acaactttac tttaaaaatt atatatgcac acatggtaaa     65340
aagttcaaaa cgtgtgtacc aaaagattta acagtgaaaa tagaaaataa gtgtggtcct    65400
tgttttcttc caccaaggca aatattgtta taatctccta aacaacttgt cttccagatt    65460
tctcattttc agtcaatctt gggcattgac ataaagaaat tcttagacat tgcttttatt    65520
agatcatctc atcccttgct caaaatcttc agtggccact gttgtttaca gaataaagtt    65580
gggatgctat acagggccct tcccagtgga acttctcttt ttcaacctta tctctcatta    65640
tttcccaatg tttttttttt tttttttgag acggagtctc gctctgtcgc ccaggctgga    65700
gtgcagtggc gggatctcgg ctcactgcaa gctccgcctc ctgggttcac gccattctcc    65760
tgcctcagcc tcccaagtag ctgggactac aggcgcccgc cactacgccc ggctaatttt    65820
ttgtattttt agtagagacg gggtttcacc gttttagccg gatggtctc gatctcctga     65880 cctcgtgatc cgcccacctc ggcctcccaa agtgctggga ttacaggcgt gagccaccgc    65940
gcccggccta tttcccaatg ttaatctact tattgaccta ctaagctggc atgttctgtg    66000
tgttagacat caccaacttt gtgccttctt ttttgtttg ttttgagtt ggagtctcac      66060 tctgttgccc aggttggagt gcagtggcgc gatcttggct caccacaacc tctgcctccc    66120
gggttccagt gattctcctg cctgagcctc ccgagaagct gagacgacag gcgcgcgcca    66180
```

```
ccatgccctg ctaacttttg tattttagt agagatgggt ttcactgtgt tcccaggct    66240 ggtctcgaac tcctgacctt gtgatccacc tgccttgggc tcccaaattg ctgggattac   66300
aggcgtgagc caccgcggcc ccctgtgcct tcttctttta ctcctggatt taatcccaac  66360
gtgaagaatc taccttacta actagagttt tagatacttt ttcaaaacca agcccacatc  66420
tgtccttttt agagtcttct ctgaccttcc ctgctcattg tggtttgttt ttattgcctg   66480
taacaatggc tgttaaactt tacattttaa attaatttat gtttgtatgt atttatttgt   66540
tgagaaaggg tctctctctg tcaccccatac tagaatgcag tggcgccatc atggcttact   66600
gcttcctggg ctcaagctgt tctcccattt cagcctcccc atgcaccacc ctacctggct   66660 aattttttg tttgtttttt ttagtttagt ttttgtagag acagatgtct cactgtgttg    66720
cacaggctga tcttgaactc ctgggctcac ttgatcctcc catctcagcc tcccaagtg    66780 ctgggattac aggtgtgagt caccatgccc agactttaac attttctttt tagtatagaa   66840
taggtcagtt ttttcctc tgatgagatc ccatgctgac tcttagttaa aacaaggctt    66900
tggttggaag aagagctagt gatgtcctag ctccctactt actccacttt cccttgcctt   66960
ctggggtgtc ctgaagacat catagggtgt catgaagtac agttggagaa ccagtggtct   67020
ccatcatgta ccaaacactc atcttcacga agcagtatgt agtgtctttt ttaccggtat   67080 atttctctc tcccaatgca ttaaacttt ctggagttca gaaaacaaat ttatagaatt   67140
aaggaaatgc gtcccccca accatggtgt ctagtatata tacagtgact tacagataac   67200
aggtgttcaa catatatata ttcctttgat tgattttga aaagtttaca tgtatatatt   67260
ttttatatac ggggtctcac tctatcactg aggttggagt gtggtgatgc agatcttggc   67320
tcaccgcaac ctcctcctcc caggctcaag tgattctccc acctcagcct cccgagtacc  67380
tgggaccaca ggtgcgcatc accatgcctg gctaattttt tatattttg gtagagacag   67440 gattttgccg tgttgcccag gttggtttcg aactcctgag ctcaggcagt ccacctgcct   67500
tggcttccca agtgtgagcc accactgaaa tacttatat tttaaactta atttatttat    67560
atttattata ttttatgtt tttatatttt aaaaaatat tttatactca ctagacccaa    67620
ttttatactc ctaaaccagg gaataactgt ttttttttct cttacatagg catgatacca   67680
tagacaatga ttaaaattgt aattaccatt catttcttag ttttgtggct gggacactga    67740
tgtcttcaaa tgttagtttg caaatacagt cagccctctc tatccatggg ttacacagct  67800
gtgaattcaa ccaaccatgg atccaaaata tatgggaaat acgctggggc tgtgggtcac   67860
acctgtaatt ccagcactta gggaggctga ggcagatgga tcacctgagg tcaggagttc  67920
aagaccagcc tggccaacat ggcaaaaccc tagctctact ataagtacaa aaaattagct  67980
ggccatggta gtgcacatgt gtaatcccag ctactcgaga ggttgagaca agcaatttgc  68040
ttgaacctga gaagtagagg tttccatgag ctgagattgt gtcactgcac tccagcctgc  68100
gcaacagagt gtgagaagaa aagaaaaaaa actgtctgaa aagaaaaaaa aaattatat  68160 gggaaatcaa aagcatctat actgaacatg tacagacttt ttttcttgtc attattcctt  68220
aagcagtacc acaactattt ccgtagcatt tactttgtat taggtattat aggtaaccta  68280
gaggtttaaa gtatgcgaga gtatgcaaat actacaccac tttgtatcag ggacttaagc  68340
atccctggat tttggtatcc ctaggggta ttagaaccaa tcccccatag atgctgaagg   68400
acaactgtag tgtgtgttgg aataatttat tttcaaatgg atcatttgga gaacactatt  68460
ctttaggaaa catagcctcc taagttctgt tccatacatc cctttcacct ccacggcgtt  68520
```

| | |
|---|---|
| gtagcatcct gctttcatga ctgtgtcatc actcggaagg aactgcttct cttccagaat | 68580 |
| gcttttcaag atctactctg accacagcta taaactttac acttctattc tcttcttgcc | 68640 |
| cctcacagtg ttctctgttc ctctaagatc ttaaactctg tctactccta atccagcctg | 68700 |
| ctgggtgtgg ctggagaaag tcccactggg gggctgatta gttaggaatg tagggtttcc | 68760 |
| agctcttgct ggagcctcag aagagttcag cagactttt ttttttttt tttccttaaa | 68820 |
| cctatttctg cagccttgat gaccactcct tccagtccct cacctatttg ctttattcat | 68880 |
| ggcagaggct ctttcttcct gcttgtcagt acaaagaggc aggattcttc acctggatct | 68940 |
| gtggattctc aaagaatttg tggagagaat tcagggcatt gatgacctg gatgaagaga | 69000 |
| aatttacatc tttatttaca ctaaccttca agtgaaattt agcatttttt gccatttaaa | 69060 |
| aatatgggca acaaacaact agtagtatta gcagtattta tgacttaagc acctatagaa | 69120 |
| ctcagttaat ttcatatcgc ttgatgttat gggtatctca aattattatt ttatgtatat | 69180 |
| atattttga gatggagtct cgctctgtct cccaggctga gtgcagtggt gcagtctcag | 69240 |
| cccattgcaa cctctgcctc ctgggttcaa acgattctcc tgcctcagcc tcctgagtag | 69300 |
| ctgggattac aggcgcacac caccacgcct agctaatgtt tgtattttca gtagagaagg | 69360 |
| ggtttcacca tattggccag gctggtcacc aactcctgac ctcaagtgat ccgcctgcct | 69420 |
| tggcttccaa agtgctggga ttacaggtgt gagccaccgc acccggcctc aaattatttt | 69480 |
| tagaaacaga atcttgatat ggtatccgct ctggccttga acttgtgggc tcaggcagtc | 69540 |
| ctcccacctc agcctcctga gtagctggga ttataggcat gtgccactgc accaggcttc | 69600 |
| aaattattat gtatgttcat cacctcttta aatttataat agttattaaa cctgttactg | 69660 |
| gatcttaata tttaatgctt taattaagaa catgtatgtt actatgccaa cagatttttt | 69720 |
| tagttttga taactgcatt tcattgttac ttgttctcat ttgatttcct gtgtattta | 69780 |
| cgaatttaag tacattctga atacggtttc ataggcttcc ctaaaatatt gaaggggccc | 69840 |
| atggattaag aaaaaggcta agaatcccta atctagaggc tccccacagt cctcttttgt | 69900 |
| catcataccc ctaccccatt ctagcctgag gagcgtggct ccacctgtgc ccttggtttt | 69960 |
| gttgttccag tccatacatc ctgcacccctt aactgtgttt cttatcccca acttgtttct | 70020 |
| ttgtgttatt cttcagtatt atagtctta atataatctg tataatacat ggtgtagtag | 70080 |
| tatatgctcg tagtatacaa ttcagttaga acagatgagt attcaatgaa aagataatct | 70140 |
| cctctctaac ccccagtccc acttccctgg ggaagcctgt gttcttgtgt acaattcaga | 70200 |
| aaatgtttat acacatattt tttatttatt tattttttga gacggagtct cgctctcgcc | 70260 |
| aggttggagt gcagtggcgc aatcttggct cactacaacc tccgcctccc tagtagttca | 70320 |
| agcaattcaa ggttcaagca attcgcctgc ctcagcctcc cgagtagctg ggactatagg | 70380 |
| cgtgtaccac cacgcctacc taattttgt attttagta gagacagggt ttcaccatgt | 70440 |
| tggccaggat ggtctcgatc tcttgacctc atgatccacc cgcctcagcc tcccaaagtg | 70500 |
| ctgggattac agatgtgagc cactgtgccc agcctgttga tttaatttta aacagagttt | 70560 |
| cgctcttgtt acccaggctg gagtgcaatg gtgcgatctc ggctcaccgc agcctctgcc | 70620 |
| tcccaggttc aagtgattct cctgcttcag cctcccgagc agctgggatt acaggcatgc | 70680 |
| accaccatgc acagctatat ttagtagaga tgggggtttc tccatgttgg tcaggctggt | 70740 |
| ctcgaactcc ggacctcagg tgatccgccc gcctcggcct cccaaagtga tgggattaca | 70800 |
| ggcgtcagcc actgcacccc gcctatacac attttttgt ttttgtttt tttgagatgg | 70860 |
| agtctcgctc tgttgtccag gctggagtgc agtggcgcga tctctgctca ctgcaagctc | 70920 |

```
tgcctccctg gttcacacca ttctcctgcc tcagcctccc gagtagctgg gattacaggc   70980
gccggccact acgccatct aacttttttgt attttttagta gagatggggt ttcaccgtgt   71040
taaccaggat ggtcttgatc tcctgacctc gtgatctgcc tgactgggcc tcccaaaatg   71100
ctgagattac aggcgtgagc caccgctccc agctatacac gtattttttaa tgccactcca   71160 gtctatgttg gaaccatttt acttccccctt tcttattttc ttcttgtgtt cttgaaggcc   71220
tagatcagct gttgctgata ggctgtcact gtcactttag aaagcccaga gccttttgtt   71280
ccttagaact ttgttttttaa ttgtattgta gcactcattg tattcgattc taaaagattt   71340
gcttcatttc tgtaactagt ctcttacacc caggagctcc tagttcctac aggaaatgct   71400
gggaattgta tcagtcaaat gtgaatcccc acctcgtcca gacttatgag tgcattgtag   71460
gtactcagta agtgctaaaa atgactaaat agtcccactg ataccaatct atatactgat   71520
actttatata gtatatagat tggtccacat ataacgatga cacataatga gaactgtct   71580 taaaaagttg ttgaaagtgc cgcaggaata ggaattgatc aaaacaatat gattttttag   71640
gtttatatgg aactttgatg tttgagaaaa ggctgattta gttgagaaga aatggttagc   71700
tgaggatttt tgatgacttct ctggaagcac atttgagggt ttgtgatgtt aaatctgatg   71760
ttaatgatta tttcatccag ttttatgtca ttttatagtt tttatacatt taagtatatt   71820
tatttctaat gtttaacact accatttttag ttatttgacc attattctgg ccctttaaaa   71880
aatgctcaga caagtttgaa tgattttttca gaggcattat tggctcagag gtaaaagagg   71940
aaagattgag aagctgaata tgtactctgt ttcctgggta tggggctggg gatacccaga   72000
agaggttcac acgttggtcg agacatttct ttatgaccac cagcaggtgg catcaccggc   72060
ccaaaatgac taagtttctg cccagaatca gaagagaagg tgttgagagc ccactgctgt   72120
gggggtagca tggaggtggg atacaggggc tggaggtgat acaattttgt ttcttcctcc   72180
aacatcgcct gctagtctag aggcttttat aaattgaaaa actaattctt tatcatctca   72240
tctgatggtt tttatgtttt tccttttttc tctctatacc tgtagttcct tcagaaacag   72300
gtaacacttt tctaatagtc acgttgtatt cttgcatctt gttgttacaa tgcttttgtt   72360
tctcaccata ggggatgatg gaaaattaat attctttgac ttatggcatt ggtaaaatct   72420
gcatgcaaat tcccacagtt gcctgtagat tagagccagt tgttttttttc tcaactttgc   72480 aggaatcctg gttacaacat tgtactattt actaccaaca gtgttttttt tttttaaaat   72540
ccagacttgc tgggcatagt ggctcatgcc tgtaatctca gcgacttggg aggctgaggt   72600
gggaggattg cttgagccca gggctgcagt gattgcggca ctacactcca gcatgagtga   72660
caaagacccc atctctgaaa aacaaaaac aaaaacaaat ttttttttaaa gaaacagaaa   72720 caaaaatcca aacttgtaac cactgtaaaa caaatcagaa tttacgatag tggatattat   72780
taatagtgca gaatggatac ccagatcttg cttcctttct agctaatgat gcaatgttgg   72840
cctgaaatgc attacttata gccagggatt ttctcagcat cctgatgata tagcctcatt   72900
tcgtgctaac tctccacttc tgcacatctt cccctaagtc ctttactcat ctttagaaag   72960
agctactttt ggtgaaattt taaaaccaag gaatatcatt ctttatagaa tcacacttct   73020
gtgttttccc cttccccatt tctgtctcga aagcgacaga ctgctacata acctgtgaat   73080
actttttttt aaaaaaagtt tggtattgta aacagaagat ttaagattaa aatgtagcat   73140
tgagaaaaat agattatta ataatgccct cttaacacaa cctaaattct ggtcagtgga   73200
ataaagcctg ggtcctaaag ttttagacgc ttgcttgctt ttccacactg gctcttactt   73260
```

```
gggatccctt ttagaaattt gtttagaata atactgtaaa aacatattta agctactttg    73320
tgtgtacatt tgggatcttt tggtttgaag acggcttgac tcaagacttt ctaaatattt    73380
tcacacacac acacataccc tgtagtgaga aaaaaatccg tttatatggt tctataaaaa    73440
tctctagctg cttcgagctt taatttcttg aatcaaaaga gtattgtttt taatactgag    73500
cttctatcta aataaatgct ttatttactt aaatgtgtgc ttttcaaaaa ctagtatgat    73560
taagacatta acaggatctt agacgtaaag gaacagtcct gttgcttctt ccagaagata    73620
atatgactcg tttggaattt tcctatagtg tagttttttg tctagtgttg tgagaattaa    73680
agggatttca ggatcttaag gtaggttatt atttgatgtt ttcttggaac attttacatt    73740
cttgaaaata cacatggcta aattaatttt tgccagcaat ccacataact ttaagataat    73800
gtagagaaga acgtgattca ggttagtatc aaataaggtc agatttctag tgccatcagt    73860
agctttcagc aaagatgagg tgttggtaag atagcattag tctcttagaa tctcttagag    73920
agattttcca aaattcagcc atttctagtg aatgctccat tccaccccca gctgagtcct    73980
gctgctctgg ggaactccct cagcacactc ttggctctta gaattgctag caatgggagt    74040
agtgctgctg gtggagctgg cagctaagcc cagaggtgga ttaatgcttt tattccctga    74100
tgtacaggta cacacactca tacctaccca cacctagttt gggataagaa gaggttagaa    74160
ttagctaggc ttgaagttcc atgcttaaat ttgctggctc agatttctta ttttggcatc    74220
actttgccca ttagggagac aatgacagtt atagaagcat tgccaaataa aaaatccatc    74280
tggaataacc tcttttgtag gagtattgtg tgtttagttg ttgattcgtc ccttcctcct    74340
cttagtggca acttacagta ctgggaagga acagtggctg ggagcttata ttcctcagca    74400
gagccagatc agcagaagta ttactcctta gttcgtagta ggtggtaccc tatgggtcca    74460
gtcatttaaa tgcaagcctg tatctacaga gcgtttccta gtgccatcat tgcccagtgg    74520
gcctttattt agctgagtct aactcccaac tagagaaaat ttcctgtgcc agacagcagt    74580
atggtcagct aacatgtgga tgctacattt gctttcataa gtcagtactc ttcaataaca    74640
ttagtagaag agaagaggac acaaagtgag agtgtgttaa taggaagtcc aggtatgcct    74700
gctacctgaa ctttctgaga caggtaatac tgtagggcct gaactttgta gcagagtggt    74760
tatatatgaa gaagtgggtt ctgggagggg ttaaaccact tagaatggct tcatttacta    74820
atggcaagag tttgctggga tattgaccac tgtacataga catgaatatg gaaagttaaa    74880
aacaaaatcc acatatattt ggctgcaagt actccgaagg tatatctaat tagtgcatcc    74940
attaaacaaa agagatattt taggccgggc atggttgctc acacctgtaa tcccagcact    75000
ttgggaggcc aaggtgggtg gatcacctga ggtcaggagt tcgagaccag cctggccaac    75060
atggtgaaac cctgtctctg ctaaaaatac aaacattagc tgggcgtgtt ggtgggcgcc    75120
tgtaatctta gctacttggg aggctgaggc aggagattcc cttgaacctg gaaggtggat    75180
gttgcaggga gccgagatgg tgtcactgca ctccggtctg ggtgaaagag caagctccat    75240
ctcaaaaaag aaaaaaaaaa aagagatat ttttgatgga ttgatagaaa ttttctttt    75300
cttttttttt ttgagacagg gtctcactct gtcgccaggc tggagcacag tggcgtgatc    75360
tccattcatt gcaacctcca cctcccgggt tcaaacgatt ctccttcctc agcctcccga    75420
gtagctggga ctacaggcat gtgccaccat gcccaactaa ttttgtatt tttagtagag    75480
agagggtttc accatgttgg ccaggatggt ctcgatctct aacctcatg atccacctgc    75540
ctgggcctcc caaagtgctg gtattacagg catgagccac cacatctggc cagaaatttt    75600
cttggtcact tctgagacat gcagagtaat tacctgtaat ataatttaat gaattatgtc    75660
```

```
aatatattaa aatatgcttc atgtgggctg ggcatggtgg ctcatgcctg taatcccagc    75720
actttgggag gccaaggtgg gggtatcact aggtcaggag atcaagacca gcctggctaa    75780
cacggtgaaa ccccgtctac taaaaataca aaaaattatc cgggcgtggt ggtacacacc    75840
tgtagtccca gctactcggg agactgaggc aggagaatcg cttgaacccg ggaggcagag    75900
gttgcagtga gccgagatca cgccactgca ttccagcctg gcaacagaa cgagactcta    75960 tctcaaaaaa aaaaaaaaaa tgcttcgtgt ggcttaaaat tatatgaaaa gaaaatacct    76020
ttactgatag tcatctgtga ttccatttgc taaattaaac gtgaaagcat acttttactg    76080
aatactatat attccgtatc agtttagata gcagttatc ttcacataca taagttttaa     76140
gtttaccttt attatagtgc attggtcttt tgttttcatc aacctaaatt atgttcaata    76200
aatgtttctg ttagatttta agttaaacaa ttatgtgaaa ttcattttc gtaattgttt     76260 tttaacatat gtctttgttg gtaattcacg tgtgtgagtg taactgattg ccagattata    76320
taaactttca accaaaacca ttctttgcag atgcttttac tgactctgct atcagtgcta    76380
aagtgaatgg cgaacacaaa gagaaggacc tggagccctg ggatgcaggt gaactcacag    76440
ccaatgagga acttgaggct ttggaaaatg acgtagtaag taacatcttt gtaattattg    76500
ctagactctg gtcagtatga catcctgtca cttggttgta atttaaatgt gcttttgttg    76560
ttgttgttat tgtagtgagt gtatttagag cagcaggttt ttgtgtataac tagagacttt   76620 ctcccaagca atatataaag aaaaatgttt gtcattttac ttgtaggggt taagcaggag    76680
tactgtctgt tcttgtggat gctcatgaat tacttctttg tgattaaaat aaataataag    76740
aagtagctta aattaaaatt agaaaccatg ggaaatgccg gtgtgttttg ctttaacacc    76800
cagccaaata aggtagccta aggaaagtgg tgtcttaatt gttgacttca cctagagaag    76860
aggttgaagt aggacatttt aagcctcttg tctgaagaaa aggttgtcat taagataaat    76920
aattaggtta cattggaatt aaagcattac ataaatttct tggtcttaaa tttggattat    76980
tctccacaaa attcttttat ttctaaaacg cctcttgtca catactagtt ttgtttctct    77040 cttaatgca ttatctgtac ttgaagtgct tagctgggta tgctggcaca tgcctgcagt     77100
cccagctact tgggaggctg aagcaggagg atcacttgag cccaggagtt ggagtccagc    77160
ctgaatgaca taaggagacc ccttctctaa gaaataaaaa taaaaacaaa tacttaataa    77220
agactctgtc tttaggatag agagcataga gatataaagc aaagtgtctt gccaaaaatg    77280
agtgttatgg taccaatatt tgagtagaat gaagaatctt ccattgagta gaaagagaat    77340
ttgtaacata tctgtgtttg atgtttaagg cataacagct taataatgac actcttcctc    77400
agacaggaag cctgaaatgt cctactttga cctaaagtct agtaataaaa ctggacatac    77460
acaggcaaca tgtcattaat tctcaaactt taacaaatca tatataaccct aatataatgg   77520 ttctcaagtc tgtacatcac gtcacctgta tgaaaaatat gaggaaacag agacttcttt    77580
tacactattg gtgaggtgga taaattgata gagtctttct ggagagaatc tggcaatgct    77640
aatcaaaatt taaaatgcac atacactttg ttccagcagt tctatctcta gtaatttatt    77700 tttgcccctca tatatccata agacatgcaa ataattatat gtgaagattt ttttttttc    77760 tttttctgca gagacagggt tttaccatgt tgcccagggt gatctggaac tcctgagctc    77820
aggtaatcca cccacctcag cctcccaaag tgctgggatt acaggtgtga gccatcatgc    77880
ctgaccagga tttttttttt tttcagcatt atttcttttg ttgttgttgc tgttgttttg    77940
agagatggag tctcactctg tcacccagac tggagtgcag tggtgcgatc tcggctcccct   78000
```

```
gtaacctcca cctcctgggt tcaagtgatt ctactgcctc agctttccaa gcagctggga   78060
ctataggcgt gcgccaccac acccagctaa ttttttgtatt tttagtagag acggggtttc   78120
accatatgtt ggccaggctg gtcttgaact cctgacctca ggtgatctgc ccacctcggc   78180
ctcccaaagt gctgagatta taggcgtgaa ccaccatgcc tggccatagc attatttcta   78240
atagtgaaaa attggaaaca tgctaagtgt ctatcaatat agcatgagtt agatttatga   78300
tgtcaccatt caattgaaac actacatatc tcccaaaaag aatggtgttc caatatggaa   78360
agatatctaa gatttattaa gagaaaaagc acattgcaga acactgggat cctatttgct   78420
tttttttttc ttttttttgag acagagtctt gctctgtcac actgcaacct ccgcctcccg   78480
ggttcaagcg attctcctgc ctcagcctcc tgagtagctg ccaccatgcc cagctaattt   78540
ttgtgttttt agtagagaag gggtttcacc atgtttgtca ggctggtctt gaactcctga   78600
actcgtgatc cacctgcctc agcctcccaa agtgctgcga ttactggcat gagccaccgc   78660
acctggccat gaaattttt ttttttttta aagagctgtt catattctta ttgcctagaa   78720
gatgtctgaa attacaccca agaaactctt tttgagacgg agtcttgctc tgttgtccag   78780
gctggagtgc aatggcgtga tcttggctca ctgaaacctc tgccttccag gttcaagcga   78840
ttctcctgct tcagccttct gagtagctgg gactacaagc gcccgccacc acatctggct   78900
aatttttgt attttagta gagacagggt ttcaacatgt tggccaggct ggtcccgaac   78960
tcctaatctc aggtgatcca cccaccttgg cctctcaaag tgctgggatt acaggcatga   79020
gccactgcgc ccggctgaaa ctcttttttt ttcttttaag atggagtctc gctctgtcgc   79080
ccagacttga gtgcagtggt gtgatctcag ctcactgcaa gctctgcctc ccgggttcac   79140
accattctcc tgccctagcc tcccaagtag ctgggactac aggctcccgc caccacacct   79200
ggctaatttt ttgtattttt agtagagaca gggtttcacc atgttagcca gcatggtctc   79260
aatctcctga cttcgtgatc ctcctgcctc ggcctcccaa agtgctggga taccaggcat   79320
gagccaccgt gcccggccag aactcttaat agtagttatt tatgcacgct gggattggaa   79380
gacatttact ttttactgga tgtctttccg tattgtgtgc tttttttttt tttttttat    79440
gtagggcata cattacttaa gtaattttaa agcctccata agtaagtgtg atttcctgcc   79500
catgtgtttg gcaaaaggaa ttgcattggt ggtagactta cattatagtc ttacctggag   79560
tagcacagga ggacccaagg ttaataggtg aacttcgagg caagccttag cattgaggtt   79620
gccatcagca ttgcttggtt gatgtgttca ttcttctggg atggattaca accttactg    79680
gactttatac ttttcaccag taaggcttta aaaaggagt tgaaacatta gagataatt     79740
atccaggcag taatattcac tggtaaatag tcttccagcc tgtggcccaa ttggttgatt   79800
cttttacgtt aaagaatgca gcctcagctg ctctgcctat ggagtaggat tcttttattt   79860
actttcttaa taaacttgct tgccctggc tcccccac caaaaaaga aggcagcctc        79920
ccttttgcga atggtaattt cctatagttt cctcgtagaa ttgtggagtt acctatgctg   79980
aggttatagg ttagggtatt gagatccaga gttgccactt ctgaggtgtc acaactgcta   80040
atggtaaaac catttctaaa gcccagttct tgtgactttg tccagtgatt gcctgttcac   80100
cgtttcatgc tgccttccca tttgagcatt cccaggagga aggggaggtt gccagggacc   80160
tagtaccata gtccgacctt ggaatcgttg aatatgaggg aaagcgttgg cttctccctt   80220
ctttctccca acattggaa gtattttggg ctgttaaaaa gcaccccttg ttccatgtgg    80280
aatcccttgt ttaaaagaag taaaatatgt acctcctgtc ctccacagac ctgaggacca   80340
gtgtgatctc aagaaggtta caggtaaatg tagatgtctc taactgaaag gtggctttta   80400
```

```
caggttagag aaaagagaga accctgatct gaaggctatt ttatgaagta attaaaatgt  80460
tctaaactttt aaaaataact gctcaaataa ttgtgttgta tagttactta tcaactggag  80520
gggctgataa gtattttttct aaaacattttt taaggaaatt ttttcctatt ttctaatttg  80580
ctaattttgc tcaagtagtt tgttagatat tgttaatata gatgttggtt ataactgaat  80640
gaaagggaac aactactttg acattttgaa aaacaagctt cattttcttc tagtctaatg  80700
gatgggatcc caatgatatg tttcgatata atgaagaaaa ttatggtgta gtgtctacgt  80760
atgatagcag tttatcttcg tatacgtaag tttgaaaagt ttgttttttat tttagtgcat  80820
ttgtctttga ttttcatcag cttaattttat gatgaataaa tgtttgttag ttttttaagtt  80880
aaacaattac atgaaataat ttttctctta ttaccaactg tgataaatttt ccattaaaaa  80940
aagggaataa atgtagtttg cctatacccct gtttttatgc tctaaacaaa ttttggtttt  81000
gtctttttttt ttcttttgag agggaatctc gctgtgtctc caggctggag tgcagtggtg  81060
caatctcggc tcactgcaac ctctgcatcc cgggttcaag cgattctcct gcctcagcct  81120
cccgagtagc tgggactata ggcgcgtgct accatgccca tctaattttct gtattttttag  81180
tagagacggg gtttcaccat gttggccagg atagtctcga tctcttcacc tcgtgatcca  81240
cctgcctcgg cctcccaaag tgctgggatt acaggtgtga gccactgtgc ctggccggtt  81300
ttgtcttcta agttgttaaa aaatatctaa atttgcaagg gcagagatta tggtgaacag  81360
tttaaccagt ttttgaaata tgttcctctg gagaaaaggt aacagaaaaa aaagttagaa  81420
ttttgattta taaatacaca gatcactata acttttagtt ttagttttag ttttagtttc  81480
tgtttttacc agtattctaa actctaaact ttcttagtag ttgattatga cagatacata  81540
aactgtggct ttaaaggact catttttgctt ttcttttcct catgtttcag agtgcccctta  81600
gaaagagata actcagaaga atttttaaaa cgggaagcaa gggcaaacca gttagcagaa  81660
gaaattgagt caagtgccca gtacaaagct cgagtggccc tggaaaatga tgataggagt  81720
gaggaagaaa aatacacagc agttcagaga aattccagtg aacgtgaggg gcacagcata  81780
aacactaggt atttaaagga aatcatgatg cagtatttttg gatacacaac tcaaggtctg  81840
tgtgagacgg tgtattgtta ttatatttttcc tcttccttta atatagctta ggtagagaat  81900
gcaagtagaa ttggtttaag atctgttaga gaaaaggtta tggtgatctt ggaaaatatg  81960
cttttgagag taagctctgt ggagccaagt gttggtatat cacggtgagc aatccaagat  82020
cttgaagagc ttgttaaaat agttatctgg tgggggacac gtgtaacaat cacagcagta  82080
caatatgatt tgcttggtta aaggcatgtt caaagtacta ggaacataca gaatgaggag  82140
gagctagcat aacctgtaga gtcagagaaa acctcattga ggaggtgaca ttttgtgata  82200
agataatagg gtctttgaca cttagagaag agttgggaga agagtttatc acctgatgaa  82260
aagccatgta caagcatggc tatgagaaaa tttggccagc tcaggagagg gctggttgtt  82320
gcatgtgtct ggaacacagg atctgtgtca ggtgcagcag tggcagttga tagtaggaac  82380
tgaggtcatt aaaggacttg gcatgtcatg ctaaagagca ccctgttgga aggagatggg  82440
gtgaataaac cctggggcat tgaggactgg ctgagacaca gagaacagtt agtgcactga  82500
aatagttcaa ctgtgagaat ttggtaacca cctagttaag gatgagcct gaggtttatt  82560
tgataactaa gtgacttaat ggatgtactg gtaagagaga gaggaaacat ggagcaagtt  82620
tgaggggaaa aacagtgact ccgtttgtgc agctaattgc atatgtgggc ttgtgggtct  82680
ttcatttatt cataaacgtg ttgagaaata cctgctacct atctagtaaa gtaagagatg  82740
```

```
catcctctct taaaggcagt cagcttagag tctggtgatt tgaattgaca tgtccactga   82800
tagatgttga cactgtgaga ctggcggttc agtttgaggt ttcatcagca ttgccgatat   82860
tggagccatg aaaaaccaaa gaacagccag tgagagaaga gatctcagag aaaataaaat   82920
tgagaaagtg aaggacaaaa aatgttgtga agatagacca agattgatgg aatcagccat   82980
agagaggtca agtgggatga gaatgagcac gcatctgtta aactttgtgc ttaggagcag   83040
aatctaaggg aagggacagt ccagaggtta gaactcaggg taagatggaa gaacaggggc   83100
atctgggagt gaggcagttt ggtttagtgt agaacctttt tgtaacaagc attcccttct   83160
gtctagatga cttttagata tgtttcattg gcttggtacc ttttagaata aaatgattta   83220
gaggatctct cattttcagg gaaaataaat atattcctcc tggacaaaga aatagagaag   83280
tcatatcctg gggaagtggg agacagaatt caccgcgtat gggccagcct ggatcgggct   83340
ccatgccatc aagatccact tctcacactt cagatttcaa cccgaattct ggttcagacc   83400
aaagagtagt taatggaggc aagtattttg accagacttg tcaatatcat tgataaaata   83460
gttttctaaa tacttaaaat acttaaaata gtttacataa ctgatatgaa tgtgcacttt   83520
aatgatttgg tgagtagctt tcacttcagc attacttaaa attggctttt gtggatatta   83580
aattagtaaa acattgtata tgtcattgac atatatatta tttagcatga tgaaatattc   83640
atgatgtact aagataaagt gctacattta acccaagaca atcacttggc caaaaacact   83700
tcacatataa agaaattgga aactttgggt aggttctcaa ttttaaaaac actggataat   83760
aaaatttttt agacataatt tatatggaaa attctaacct atgtgcaaca ctgtggttaa   83820
tatagatcaa ttttcattat ttgtttctat attatgctta cttcaagaaa ggatctgagg   83880
taacttataa tacaagacat gatcaagagt catgtgaaga aagtgactag agaaatttgc   83940
ttaaaaaaca acaaaaacaa cccttagtct aagggtggat gttacagttt agcaacttaa   84000
gtaaaagaaa cctgaatctt tagtaggaag acatttttta ctctacctct aaatctaggt   84060
tgaatatatc ttgtaggttg tggatctttt ccataaatca gggatactga acaacagttc   84120
tatggatggt atggaaatag taatagcaat agtatgttac taactttgtg ggaaaagagt   84180
ggacattcaa ttttagctat ttaaatttgg aaagttagat gaaaatagag aacactaagt   84240
ttccaatttc atttgttttc attgagtctt ttctccagaa ttcctctcca aatggacact   84300
cttgagtatt ttcagtactt aatattgggg gtgaaatttc tttgctcact gaggaaagat   84360
tttagttgtt tataaacaga atttttaaagt taaaaaacct gaaggggggct gagaaatata   84420
tgatacttaa gtgtgtggaa ccctatggag aggagacctg gactgtttga taagattaag   84480
gtaagtgata tgtaatgtta aatactagct gtatctttac ctaggcatat ccatcagtat   84540
aaatttattt ggtgatgact gctttgtagt tgcagtattt attaagcagt cgcttagata   84600
agtgtttaac tgtataaatt atttagaagg tctcccttttt tctagtttaa tgaggtcaag   84660
acttttttt tgaaatagca atgaatatta tcatttgata ctcacaggag tcacaaactc   84720
tagaagagta atgtttatt tctacttaaa tgggacttgc ttaataagat tccaaactga   84780
gttctgggtt caagtgtaaa cctgatgaaa atcatagata attgtaagga accagcattt   84840
ctaattggat ataatagcta ctgcttattt tcgttatgcc tcagagttaa aactaataca   84900
gtaaataatc ttactcctga gtaggaatta ttgtgattta ttatgtgaaa ttatctagtg   84960
tatgttatat tccttttaaac aaccagttac tgagaaacag ttatagaagc aggattaata   85020
ggcaaagtct taactgtctt cttcaatagt gtgtatagat cctaattaac cctttgggaa   85080
cgtgtattca tttaaacaga cttaatctta aggaggttaa agtaaaatgt gaatttatgt   85140
```

```
cagttaagtt atgctaaaac ttatcacaaa tcaaatgact gtcctcaaag ggttaaaatg   85200
tacaagaaat catttttgtc attttacttt ttttctgttt actttttcc  ctcattttt    85260 tctttagttt ttatactttc cttcatatca tttgttctgt caggtgttcc ctggccatcg   85320
ccttgcccat ctccttcctc tcgcccacct tctcgctacc agtcaggtcc caactctctt   85380
ccacctcggg cagccacccc tacacggccg ccctccaggc cccctcgcg  gccatccaga   85440 cccccgtctc acccctctgc tcatggttct ccagctcctg tctctactat gcctaaacgc   85500
atgtcttcag aaggtacaat accacaattt gttcatgttt ttgtttgtct ttgtttaact   85560
cctatgtgag tttataatta caaaatagtt tcctcttcat tatttaataa cctataattt   85620
ctgtgtttta actttagttt attaaaacta tttctattaa cctttttgttc attagagaga  85680 aatttgataa atgtgtgaag ctataaactc tcttgaattg ttgttaaaaa gggggtttat   85740
ctctgcctga taattatgct tctttacagc cccagaaggg tctgcccac  agccttcccc   85800 ctccttattt gcactgtata cagtagttaa acaaatgaac tttcttcagc cagtcttgaa   85860
cttaggttca ttttacagct ctttggccaa ggtcctagtg aaccttccta ttggccataa   85920
gcagggatgg tgttttctgg gtcttttttg agagcgacag cccatgtagc tgactttgcg   85980
tgtctgccct tagattaaag tagttgattt ttagaatgcc agaagaattc taaatttaac   86040
tgagtaattt ttttaaagtt agcttttgcaa tcttacatag tgaaaggctg ctttaatctg   86100
gaagaagtcc ttgatctgag ataaaattga taaaaacgac atatgaattt gaatatttag   86160 ctatttctttt cctcgtcaaa aataagaata aaatcttgta attcttattc agtatttggc   86220
gctaaatcca tcattgccac atatcaaata cagggatatg ttgtagaaag gtaacattct   86280
aatttaaatg ccacccatat attaaaaacc tgtttttctga atcataatgt ccttttgata   86340
ctagttctga atatttgtgt taaaatttta atctgatttg ttcattaaaa ttagttaata   86400
ttgcttatgt tgggactaat aaagttttcc gcacaaaatg tgtttctcct gcttccctgg   86460
agaaaactgt attggctact tttaaataaa ttgttaccat ctaagcaggc aggtcatatg   86520
actttgactg aagcatctaa ccttgaagag caagttccac tgattttcaa ggtgacttct   86580
ttgctcaaaa gggccttaat agtggtcact aaatgcaaaa ttctgttgat attttttcttg  86640 tagtccatca tttgagtaag cgatgtttat ttaatgagaa tatattaaat aaaacatgat   86700
cattaatgac tgtgaacatc tttattacat taagatttaa ggactgctca tgtattaact   86760
tcacacagaa atatactttc tgtgtcattc agagatgttg aatatttcca tttgaaaatt   86820
atagtgtata acattagcat tcttctaaag atcatgttcg tgtttaaatt cctgttggaa   86880
gccaggcatg gtggctaacg cctgtaatct cagcactttg ggaggctgag gcaggtggat   86940
cacttgaggt caggagtttg agaccagcct ggccaacatg gtgaaacctc gtctctacta   87000
aaaatcccca gctacttggg aggctgaggc aggagaatca cttgaacctg ggaggcagag   87060
gttgcagtga gttgagatcg taccactgca ctccagcctg ggcgacagag acagactctg   87120
tcttataaaa ataaaaataa aataataatt ctattggcaa catatattaa tttgaagttc   87180
taaagagttt ggcagccggg tgagagagtg aggagatttg ctttgacat  tagggaagtt   87240 ttcgcttggt gttaacacca gtaggcttct ctgatgaggg ccattctgtc cactcttta    87300 cctgatagat tggtctaatg cacagtagac tgatttagaa agagtagtca ctagtggcat   87360
ggcagaatca ataatgtaga attttgacaa ttcatatagt gctgatttct ccccaaatg    87420 tcagttattt tggtcatcta ttaatagact aatacaagtc atcccttttaa tagaattttc  87480
```

```
agctcacagc ctgctaagcc taagaaactg cttacaggtt actgcttact gttttaagcc   87540
gagtttaaaa attgatgatc atgatagaag agataaataa actaaaattt tagagaaatt   87600
taagaagggt atgtacatat gttttagtgg tatcggggtg tatagggatt aatagtcttc   87660
tgtttaaatt tttttttttct aattttagaa gtaatgtaga aaattcgggt cagggaaagg   87720
taaaatatat ggaaagttaa aaatatttta tcatgtagtc ataatttcta gtaacatatt   87780
tctttacaaa taagacatag ttgaaacaga ttgctacagt tcttttaaga gttgacatct   87840
tattgttgat ttcttaccac caacttcatc cctcccttc tttaaaaata aagggaaata   87900
ataaaattta tttataaaac tttgtggcat tccacaaaat aattctgaaa gaattagtat   87960
ggccaaaaaa atatgtatgg tgttttttt ttttctattt ttaaccaagg aaaaactgta   88020
gagtgagtga gtgtgtgtgc atgtgtgtgt gaatgggtgt atttagcaga aaagtagtac   88080
tgatgaatat catggaattt atgtgatgtt cactgtttct tccttagggc ctccaaggat   88140
gtccccaaag gcccagcgac atcctcgaaa tcacagagtt tctgctggga ggggttccat   88200
atccagtggc ctagaatttg tatcccacaa cccacccagt gaagcagcta ctcctccagt   88260
agcaaggacc agtccctcgg ggggaacgtg gtcatcagtg gtcagtgggg gtaggtaaca   88320
cttgggcata atgatggtac tcattttgtc attacactag atataaagag ggctgagcta   88380
caactctgtt tgaggaagtg taagtatgta tatgttaaaa atagtagaat caccaggaat   88440
tgggaaaccc atattttat tctgggctct accacttatt catcatatat taaagcaagt   88500
cagacactca ttctgaagtt gagatttcgc agtgagtaaa gtgttaataa ttcttgccta   88560
gtctacatta tgggattgtg atgagattcc tataaggttc ataaatacag atatattgta   88620
aaactataaa gttttgtaaa gtacctctct aatatgaggc aaacacagta tgtaacacta   88680
tttggaggga ccgtatttcc ttatcttttt agcagctttg tttatcagta cattctataa   88740
acatttattt ttggcttaca ttgtagtgtg tttctatagc atctgtatat ggcactaatt   88800
cccaactata tttccataat aaggaatatc aaatacaaat aaagggtcca agttttattt   88860
gtgattagca taaggaatat gctgacagca gctataaaag tataaaaatt aggctgggtg   88920
tggtggctca cgcctgtaat cccagcactt tgggaggctg aggtgggcgg atcacaaggt   88980
caggagatcg agaccatcct ggctaacacg gtgaaacccc gtccctacta aaagtacaaa   89040
aaaaattagc cgggcatggt ggcgggtgcc tgtagtccca gctacttggg aggctgaggc   89100
aggagaatgg catgaactcg ggaagcggag cttgcagtta gctgagatca cgccattgca   89160
ctccagcatg gcaacagag caagactctg tctcaaaaaa aaaaaaaaaa aaaaagttta   89220
aaaactagac gttgacatga ttttacaata aggctgactg cttttgctac tttgccaatc   89280
agtccttagt gctttgttcc cataactgtg gtaagcaaga gcttacaaag aatacttaaa   89340
acaaacaaac aaacaaacaa aaaaaacact ttttctcttt taatcagtcc agagaacctt   89400
taaaagaaac aagatcggcc agttgctgtg gctcatgcct gtaatcccag cactttggga   89460
ggctgaggtg ggtggatcac ttgaggtcag gagttcaaga ctggcctgac caacatgatg   89520
aaaccccatc tctactaaaa atacaaaatt agctgagtgt ggtggctatt tgagaggctg   89580
aggcaggaga atcatttgaa cccaggaggt gaaggttgca gtgagccaag atcacaccat   89640
tgcactccag tctgggtgac aagagcgaaa ctctatctca aaaaaagaa aaagaaaca   89700 agatcttcaa gcttaaggaa acaaaaacaa aactcagctg tgttaaatct gttttagtt   89760 gctatacatt tctgctcagc ttcatgtgat gcacattcat gtaattgtat cctaaattcc   89820
tttgtacttt ttattttctt ccttggtctt caattatctt aagactacca agaaaacaaa   89880
```

```
aattttaaaa atcttcttca gccggtcagg cgcagtggct cacgctgta atcccagcac   89940
ttggggaggc tgaggcgggt ggatcacgag gtcaggagtt caacaccagc ctggccaaca   90000
tggtgaaacg tcgtctctac taaaaataca aaaattagct gggcattgtg gcgcgttctt   90060
gtaatcccag ctgctcagga ggctgaggca ggagaattgc ttgaaccagg acccgggagg   90120
tgtaggttgc ggtgagcgga gatcgcgcca ctgcactcca gcctgggcta tagagtgaga   90180
ctccatttca aaaaaaaaa aaaaaatctg cttcagctat tctgttaatc ttttgacatt   90240
acttagatgg tctggaaata aattttgaga ataacatgat tagaagtgag agagtataag   90300
catagttttg gagatacact cagaatagca ttatagattt tctcttttta ctaattggaa   90360
aaatggcagt tgttgaataa tagttttctt ccgtgaccct tgtgacttaa aaaaaaaaa   90420
acactgaaat gaaataatcg aaccattttc tctaaacctt tgaatctgag ctctgcagtt   90480
aggtttataa tggtatatga aacctattag atatatactt ggaagtcata tgggatacaa   90540
accctgcttt tattatcttc ccctttgac taacttgggt ctcaagtttc cttaattact   90600
gcacagtgga ccttgatgtt gctataaaga atgtgtaggg ctgggcatgg tggctcatgc   90660
ctgtaatccc agcactttgg gaggccaagg taggcagatc acctgaggtc aggagtttga   90720
gaccagcctg gccagcatgg tgaaacccg tctctactaa aaatacaaaa aaattagctg   90780
gttgtggtgg cgagtgcctt taatcccagc tactccagag gctgaggcag gagaatcact   90840
tgatacattt agttaggaga gaaaatcata cttatgttag taattgctgc tgttcttcat   90900
atacttgtgg ttttgattgc cagcaaattc ctaacatttt ggaaaagaaa acagtaatgg   90960
gataaaggat aagggctaga gaggacagtt ttatttacct agatcttcag agaagcctga   91020
agcctctttt aggaagtaac atttgaactg agaatgtaat aaatacattt tcccttttctt  91080
ctagttccaa gattatcccc taaaactcat agacccaggt ctcccagaca gaacagtatt   91140
ggaaataccc ccagtgggcc agttcttgct tctccccaag ctggtattat tccaactgaa   91200
gctgttgcca tgcctattcc agctgcatct cctacgcctg ctagtcctgc atcgaacaga   91260
gctgttaccc cttctagtga gggtatgtaa caaagggctt ctggatccat aatctcagct   91320
gtgaaattga atgttagagg gtgatattat atgaaaaaat tctaggttat ttttattcat   91380
agacaagtat ttttagtgca catttaaaag tttatgtaaa ttttgatgtt gtttaatact   91440
actaatttaa tatagtgtct gtgttacaaa ggttaacatt cctgggtgtc aaatacctac   91500
ataaataaaa ttattggtgt ttcatatgac atctgcaaag gaaaaaaagc ctctgtttaa   91560
atgaaagcat tattttccaa aaacatagga aatcaaaatt attgttcagt gttttcttgt   91620
tttgcttttc taacttatct gaattttttt taaaaaattg ttttctagct aaagattcca   91680
ggcttcaaga tcgaggcag aactctcctg cagggaataa agaaaatatt aaacccaatg   91740
aaacatcacc tagcttctca aaagctgaaa acaaaggtta gagtttaaag agtcattaag   91800
cttaactgta ggaataggaa gaagtatgtc taatttcatg cccatacaga atattttgt    91860
tcaacatttc ttcttactat tgtgatagat aaatgtattg cttgacaaat tccaaaatcc   91920
aaatttaata tttgaaatta ttttctgatc ttatatctta ttctaatttc tatcatctca   91980
tactaaaaag aatgtgatgt taaagtttaa aaataaacct gtgtcttaac agttcttaat   92040
tttacaggta tatcaccagt tgtttctgaa catagaaaac agattgatga tttaaagaaa   92100
tttaagaatg attttagggt aagtattgta ctaactgatg aatttgagtt ttagaaaata   92160
agcattacta aagatttatc tatttataaa aatgcgttat gtatacagtc agaaacatca   92220
```

| | | | | | |
|---|---|---|---|---|---|
| aaccatatat | gtagaaagca | gaacattttt | aaagtggtct | ttgcctatcc | tttaagtggg | 92280 |
| ataactaaaa | tcatgagatt | tggtaacaac | aatatgtagg | tatcaaatga | gagtatagcc | 92340 |
| ctgacatttg | aaaccaccat | agcacagctt | actatttgat | ggtcatttgt | actttgttca | 92400 |
| gtgaagctag | atattagtag | agcaaggcca | agtcattaat | aatctagtgt | ggcaaatgga | 92460 |
| agatgtactg | gactctggtg | ttctgaggta | gttggagatt | tatactttgt | acacaaatat | 92520 |
| attgtggtca | aaatctttct | gtaacattat | ttctctgtct | tagcacaggc | tttacttaac | 92580 |
| atctctcctt | gattgtcatt | tcattctttt | gcatgttatt | tactataggt | atcgaggtag | 92640 |
| attttgagac | caaccaataa | atcttcttga | aacttagctt | cttagaaagg | aaaatctaaa | 92700 |
| taccagcctt | ttaaaaaaag | tagctgaatt | aaaggatgag | tgaaccaaag | gcaaaggtag | 92760 |
| cctttcctca | gcctgtgttt | tagctttcta | aatgttaaca | atagcttcat | tcttgactta | 92820 |
| ttggtaacat | tcaaaatact | acttattatt | tcatacttta | gcacatgtat | ctattcagct | 92880 |
| ttaatgctat | taacagttgt | taacctaagt | tttcatttgt | tggcgggcac | ggtggctcac | 92940 |
| acctgtaatc | ctagcacttt | gggaggccga | ggtgggcaga | tcacctaagg | tcaggagttc | 93000 |
| gagaccagcc | tggtcaacat | ggtgaaaccc | tgtcttgacc | aaaaatagaa | aaattagcta | 93060 |
| ggcatggtgg | cgcacacttg | taatcccagc | tacttggcag | gctgaggcag | gataatcgct | 93120 |
| tgaacccagg | agacagaggt | tgcagtgagc | cgagatcaca | ccactccact | ccatcctggg | 93180 |
| cgacagagca | agactgcatc | tcaaaaaaaa | aaaaaaaaa | aaaagtttt | tcaatttgtt | 93240 |
| aaacaatagt | taacacatac | aaatgataca | agaatattg | aatatgatca | tgtgcccact | 93300 |
| acccagctta | gtaaataaag | cattctaaca | cagttaaact | cctcttatgt | atctgccct | 93360 |
| cctcagctgc | ttcccctgt | ttccttccaa | aaggaagggt | ttctttctg | tgcagttctt | 93420 |
| tatatttata | ctgcatatga | atatatctgt | gagcaataga | tgatattttg | cataatctta | 93480 |
| aatttgctat | aaagtctttt | tttttttttt | aattgatcat | tcttgggtgt | ttctcgcaga | 93540 |
| ggggatttg | gcagggtcat | aggacaatag | tggaggaag | gtcagcagat | aaaaagtgaa | 93600 |
| caaaggtctc | tggttttcct | aggcagagga | ccctgcggcc | ttccgcagtg | tttgtgtccc | 93660 |
| tgggtacttg | agattaggga | gtggtgatga | ctcttaacga | gcatgctgcc | ttcaagcatc | 93720 |
| tgtttaacaa | agcacatctt | gcaccgccct | taatccattt | aaccctgagt | gacacagcac | 93780 |
| atgtttcaga | gagcacaggg | ttgggggtaa | ggtcatagat | caacaggatc | caaggcaga | 93840 |
| agaatctttc | ttagtacaga | acaaaatgaa | aagtctacca | tgtctacttc | tttctccaca | 93900 |
| gacgcagcaa | ccatccgatt | tctcaatctt | ttccccacct | ttccccctt | tctattccac | 93960 |
| aaagccgcca | ttgtcatcat | ggcccgttct | caataagctg | ttgggtacac | ctcccagacg | 94020 |
| gggtggtggc | cgggcagagg | ggctcctcac | ttcccagaag | gggcggccgg | gcagaggtgc | 94080 |
| cccccacctc | ccggacgggg | cggctggctg | ggcggggct | gacccccac | ctccctcccg | 94140 |
| gatgggcgg | ctggcgggc | ggggctgac | cccacctcc | ctcccggacg | ggttggctgc | 94200 |
| cgggtggaga | tgctcctcac | ttcccagacg | gggtggctgc | caggcggagg | ggcttctcac | 94260 |
| ttctcagacg | gggcggctgc | cgggcagagg | ggctcctcac | ttctcagacg | gggcggccag | 94320 |
| gcagagacgc | tcctcacctc | ccagacgggg | tcgcggccgg | gcagaggcgc | tcctcacatc | 94380 |
| ccagacgggg | cagcggggca | gaggcgctcc | ccacatctca | gacgacgggt | ggcgggcag | 94440 |
| agacgctcct | cacttcctag | acgggatggc | ggcggaag | aggtgctcct | cacttcccag | 94500 |
| actgggcagc | cggcagagg | ggctcctcac | atcccagacg | atgggtggcc | aggcagagac | 94560 |
| gctcctcact | tcccagacgg | ggtggcggcc | gggcagaggc | tgcaatctcg | gcactttggg | 94620 |

```
aggccaaggc aggtggctgg gaggtggagg ttgtagcgag ccgagatcac gccactgcac    94680
tccagcctgg gcaccattga gcactgagtg aacgagactc cgtctgcaat cccggcacct    94740
cgggaggccg aggctggcag atcactcgcg gttaggagct ggagaccagc ccggccaaca    94800
cagcgaaacc ccgtctccac caaaaaaata cgaaaaccag tcaggcgtgg cggcgcgggc    94860
ctgcaatcac aggcactagg caggctgagg caggagaatc aggcagggag gttgcagtga    94920
gccgagatgg cagcagtaca gtctagcttc ggctcggcat cagagggaga ccgtggaaag    94980
agagggagag ggagaccgtg gggagaagga gaaggagggg gaggggagg ggggagagg    95040 gagagggaca atgatgtctt gctgtaggta ttcttcccca tttgaatttt ttcctcagca    95100
ttattttttt taacatcatt cagtctcctc ttatactaca cttggattga atttaatatc    95160
tcatgaagaa aaaacatttc tactttgaag catgtgaatt agcatgtttt tataacagct    95220
ttattgagat ataatttaca tatataaata aaccgtttaa agtgtataaa tcagtggttt    95280
ttaatgagat ataatttaca tatataaatc aaccatttaa agtgtataaa tcagtggttt    95340
ttaaaatatt cacaatgttg tacaaccgtc ttctcagttg attttaaaac atactcttca    95400
cccccaaaag aaacccgtg cccagtttag cagtcgttcc acatttgcct ccagcccttc    95460
tctttcccct actcccaacc ctaagcaacc gttaatctac tttctgtctc tatggatggg    95520
cttatttggg gcaaattcca tttcatacaa atggaataat aaaatatgtg gcttttatga    95580
ctggcttctt tcactcagag tagtgttata aaagttcatc catgttggag catgtttcag    95640
tacttcattt cttttgtga ctgactaata ttccttgatg tggataatac cacatttgt    95700 ttatccatta atcagtttgt agctatttgt ggtgttctca ctgtttgact attctgaata    95760
acactgccac aaacatgagt gtgcagtttt tttctcgtcc tatcttttca tttcttttgt    95820
gtacctacct aggagttgaa ttgctgggtc atatggcaac tgtgtttaac cttttgagga    95880
actaccaagc tatttgccaa gatatctaca ctattttaca ttcccaccag cagggtatga    95940
gggtttctgt ttctccacat ccttgctaac acttattgtc ttgtcttttt tgattatagt    96000
catccttgtg ggtgtgaagt gttaacctca ttgtggcttt aatgtgcagt tctttcatgg    96060
ctaatgatgt tgaacatctt ttgtgtttat tggccattta tatatcttct ttggattgat    96120
gtctgttcaa atctttaccc attttaaaaa ttgagttgtc tttttattat tgggttgtgg    96180
gagttcttta tatattgtgt gtacaagtcc ctgttagata catggtttgc aaatgttttc    96240
tcctgttctg ttggttgtct ttttactttt tcatcccttg aagcacaaaa attttaatt    96300 ttgatgaagt ccaatttatc tgattttgaa gtaagctttt ggtgtcgtat ctaagaaaat    96360
actgtttcat caatcattaa ggtttattac tcttctgggt ttttttaaga attacattta    96420
gaggtgtgat ccatttggag caactttttt tttcttttga cacagaatct cgctcttttg    96480
cttaggctgg agggcagtgg tgcaatcttg gctcacagca gcctcagcct cctgggctca    96540
aatgagtagc tggtactaca ggtgtgcacc accacacctt gctattaata acttttgtat    96600
ttttttgtag agacagaatt cgccatgtt gcccaggctg gtctcaaaca cttggactca    96660
agtgacacgc ccacctcagc ctcccaaagt gaaaaattgc tttcaccttg cactgcggac    96720
tcgccctgaa ttctttcttg tgcaagatcc aagagccctc tctgggggtc tggatcggga    96780 ccccttttcct ataacaatat tatgagaata acatttgatt tttttaagt gaaacaaatt    96840 gttattaaaa aattaaaaaa ggtcatagga gagtgacttg gtgctcagcc cattttgagc    96900
agttatttaa tatagcataa ggtggggttc aaattcattc tttatattaa tttttttatttt    96960
```

```
ctaattgaca cataaccata cacttataac cattttttact gtgtaagttc agattcattc    97020
ttccgtatgt aggtattagt tgtcccagca ccatctgtta aaaagactat tcttggccag    97080
gcacagtggc tctcaacgcc tgtaatccca gcactttggg agtcccaagc aggcagatca    97140
catgaggtca ggagttcgaa accagtctga ccaaatggtg aaaccgcatg tctactaaaa    97200
atacaaaaat tacctgggtg tggtggcgca cacctgtagt ctagtcccac tactgtagtg    97260
gctgaggcag gagattcgct tgaacccagg aggtagaggt tgcagtgagc tgagatcatg    97320
cactccagtg tgggcgacag agtgagactc catctcaaaa aaaagactat tctttcctcc    97380
attgaattat cttcacatgc ttgttggaag tctgttgact acaaatgtga aagtttatta    97440
ctggactctg aattgtcctc cactgaatct ctatgtctta tccttatggc agtaccatac    97500
tgtcttgatt agagttactg tattttaaaa ggctgtactt tttcagttag cagaaaacat    97560
tttagctatc agcacaactt tctgtaaacc ttcattaatg cttgacttaa attccaagaa    97620
ggagcaacat aaaaagtctt atctctttag gagttttagt cttactactt ttaggtgcct    97680
gaataaccaa atgtattatt tagcctctta ctaataactc cttgatccat aggggcatac    97740
caggaagaaa agaagtggtt tttaaaaaat gagagtgggc cgggcacggt ggctgatacc    97800
tataatccta acactttggg aggctgaggc gggtggatca cttgaggtca ggagtttgag    97860
accagcctgg ataacatggc gaaaccctat ctttattaaa aatatataaa ttagccgggc    97920
atggtggcac atgcctgtaa tcccagctac tcaggaggct gaggcaggag aatcacttga    97980
atccaggagg tggaggttgc agtgatccga gattgcatca gtgggcgaca gagcgagaat    98040
ctgtctcaaa gaaaaaaaaa gagagtgaaa aaaaaaaata tgtgtcccag aacttaaatt    98100
ttaattaaaa aaaaataaaa gagtgaactt tctaattgtt ctcttcagat aatataatgt    98160
tattctctta tgttttattg cgtatttcct gtgtaccaga tgctgttctt catgcttgta    98220
tgttaaatct tgtctaacat ctctgtcaag caagttctgt ttgtatctgc actgtgtata    98280
ttaggcagct tgggcaaaga gaagttaagt aatctgccca aactcacatg gctagtaagt    98340
aagagggctg accatctggt gtttaagctt ctagcagtgc tttgaatagt aactaatgca    98400
tagtgcatgc tgcactgtca gtcagtgatt cattagagct aacttcatga catgctcata    98460
gccccaaact gcatttgttc acaaatatct gtagtccttc atttaggcag aaatagaaat    98520
accttgtgtg tttgttgttc cttcccttttt gagccatatg cagagtgctg atagctttat    98580
ttgtgtaaga attgctagta atttgatctg tttttgggtta ataatgtggg ttttagaggt    98640
aaatggacct aggtttgaat gttggcctct atacatcatg tgcgtaacat tgtggcatgc    98700
tatctacttc ccccaagcca aaatgggtta attttagaac ctgcttcata gtgttcctgt    98760
gagagctcga tgagatattg cctataaagt gtttagcata gtgcctagca catggtatgt    98820
attcaataca tgttcattct tactagcaaa atatagatga cccagtattg tacagagtat    98880
gtacaatggt gtcattgtac catttcatgt ggagtcacat aagaatttca gttttctgct    98940
gggcatgatg gctcactcct gtaatcccag cactttggga ggctgaggtg gatggatcag    99000
ctgaggtcag gagttccaga ccagcctggc cgacatgatg aaaccccatc tctactaaaa    99060
atacaaaaaa ttagccaggc gtggtggcag gtgcctgtaa tcccagctac tcgcaagact    99120
gaggcaggag aaatgcttga acccgggagg cggtggttgc catgagttaa gatcgtgccg    99180
ctgcactcca gcctgggcaa taagagcgaa actccgtctc caaaaaaaag aaaaaaaaag    99240
aacttaagtt ttccattaga tttagtatag tgcagagagg aaaatacagca gagtgctata    99300 ttccatatat agcaatatag cattagaaca atatattcca atacagcaga gtgctatatt    99360
```

```
cagataccaa ctagtggact tgctatttgt aagatggcaa taatagtatc tacatcaaat   99420
agggctgttg tgaagactaa atgaataagt ctataaatag tttagaacag tgtctggaca   99480
ggtacagtgg ctcatgcctg aatcttagca ctttgggagg ctgagacagg tggatagctt   99540
gagctcaggc attaaagacc aacctgggta acatggtaaa accctgtttc tacaaaaaaa   99600
tacacacatt agccaggtgt ggtggcacat gctaatagta ccagctactc aggaggctga   99660
ggtgggagaa tcacttgagc ctgggagatg gaggttgcag tgaggtgagc ttgcaccact   99720
gcgctccagt ctgggcaacg gagtcagacc ctgtttggaa aaaaaaaaa aagtgtccaa   99780 cccatagtaa gaaatgcaga tgtgtttgac attgtaagaa aaagcaacac caaaagtctg   99840
atttttgcct tcactcaaga actcttatga taattaaact ccgaagtcct tggcaatata   99900
tatagttggt ctgttatgtg gatcgcctct actaaagatt tttgtgaaca aatgaaagtt   99960
taagtagtaa gttcctacat cgtgacttaa attgccagtg tgcccacata aatacccgt   100020 caacatttgc ccttagccac ttgactcttt agctatattg gtaatgcagt aaagcttgcg  100080
atgcgccaga gttgcataat gctgtttgcc atgacaccaa gagccttggt aatgaaacca  100140
ttgaaattgg tttgcctata ctgaggctga agaggtatct tggctctcta attttaaggc  100200
aacctttttg gctgtgtagg tttctcttta gcttgtttct caccacctgg ggctgtggct  100260
taggtccgtt gtcctaacct gtggcttagg ttctgttttt gttgcttgta cttgctcccc  100320
cttttttcag ccattcctgt tttctttctt ttgtagagga tgccatctta aatcatcttc  100380
agccagtggt agcattttat ttttctggt ctgcaaactt aaaaacctca tcacttattt  100440
tgctaatatc tttgtcttct gttcttttg atggtccttg gttttgcagt ctacttaaa   100500 ggttttatt tttttatggg tacatagtag acgtattatt catagggtct gtgagatatt  100560
tagataaagg catataatgt gtaataatca cattagggta aatgggtat ccatcaccat    100620 catcattcat catttctttg tgtaatgaac gttgcaattg tactccctca gttattctaa  100680
aaagtacaac aaattaatgc tgactgtagt caccctgctt tgttgtcaaa tactagatct  100740
tattcattct ttatttaact ttttaaattt taaacttatt ttatttattt attttttagac 100800 ggagtctcac tctgtcgcca ggctggagtg cggtggcgca gtctcaactc actgcaacct  100860
ccgcctccag ggttcaagtg attctcctgc ctcagcctcc tgactagctg aactacagg   100920 cacgtgccac cacgcccagc taattttgt attttttagta gagacggggt ttcactatgt  100980
tggctgggat ggtcttgatc tcttgacctt gtgatccggc tgccacagcc tcccaaagtg  101040
ctggggttgc aggcgtgagc caccgtgccc ggcctttaaa attattttaa atcattttaa  101100
tatctttttc atttctgcct ccggtcctgc agagttctta ttcgttcttt ctaaatttc   101160 tttgcaccca ctaatcacct catttccctt cttctcccca ttaccttcc caacttctgg    101220 taaccattct gctatctcca tgtgttcaat tgttttatt tttagtgcct gcaaacgagt   101280
aagaatatgc aaagtttatc tttctgtccc tggcttattt tacttaacat aatgtcctcc  101340
agtgccatct acattgctgc aaatgacagg atctcattct tttttatggc tgaatggtaa  101400
tctattgtgt atatatacca cattttcttt ctccatttgt ctgtcagtgg acacgtaggt  101460
tgattccaaa tcttggctgt tgtgtatata gtgccgtagt aaacatggga gtgcagatat  101520
tccttcaata aactgatttc ctttctgagt atatacctag cagtgcaatt gctggatcat  101580
atggtagctc tattttagt ttttgagga atttccatac tgttctccat agtggtttta   101640
ccaatttaca tgtccaccaa cagtgtgtga aggttcccct ttatccacat cgttaccagc  101700
```

```
atttgttatt gcctgtcttt tggataaaag ccattttaac tggggtgaga tgatatcttg   101760
ttgtagtttt aatttccatt tttctggtga tcagtagtat tgaataccTT tcatataccT    101820
gtttgccatt cataaataac gatgaggtct tgctgtttgg cccaggctgg tctcgaactc   101880
ctgggctcaa gcaatcctcc caccttggct tcccaaaatg ctgaaattat agttgtgagc   101940
cactgcacct ggccttgtat gtcttccttt ttttttTGTT ttgttttgtt tttgagacag   102000
agtctcactt tgttgcccag gctggagcgt agtggtgtga tcttggctca ctgcgccta    102060
cacctcccgg attcaagcaa ttctcctgcc tcctgccacc atgtctgcct aattttTGTA   102120
tttttagtag agacgggatt tctccttgtt gcccaggctg gtcttgaact cctaacctca   102180
ggtgatttac ctgcctcagc ctcccaaagt gctaggatta caggcgtgag ctgctgcgcc   102240
cagcctgtat gtcgtctttt gagaaatgtc tattcagatc ttttgcccat ttttaattga   102300
gttactaaaa ttttccctat ggagttgctt gagtgccttt tatattctgg ttattgatcc   102360
cttgtcagat gagtagtttg caaatatttt ctcccattct gtgggctgtc tcttcactTT   102420
gttgatggtt tcctttgctg tgcagaagct ttttaacttg atgtgatccc atttgtccat   102480
ctttgctttg gttgcctgta cttttgggGT attactcaag aaatctttgc ccagagtaat   102540
gtccctggga gtttaatgtt ttcttttagt agtttcatag tttgaggtct tagatttaaa   102600
tctttagtcc atttTGATTT GATTTTTTTT taatatggtg ggacacaggg gtctggtttc   102660
attcttctgc atatggatat ccagttttcc cagcaccatt tattgaagag actgtccttt   102720
ccccagtgta tgttcatggc ttctttgtgg aaaatgagtt cacttagacg tatggattca   102780
tttctgagtt ctctgttctg tttcattgat ctatatcttt ttttatgcca gtaccatgcc   102840
attttggtta caataatttg aagtcagata atgattcctc ccgtttTGTT cattTTGCTC   102900
agtatgGCTT ttgctctttt gggccttTTG tggttcccta caaattttag aattatttTT   102960
gtctacttct gtgaggaatg tcattggtat tttgataggg attgcactga atctgtagat   103020
tgctttgagt attatcaaca ttttagcaat attaattctt ctaatccata aacatggaat   103080
ctctttTCAT gttttttctg tgtcatcaat ttcagtgttt taaagttgtc attatagaaa   103140
tcttttactc atttggTTAA gtttattcct aagtatttta ttatatttgt agctattgta   103200
aatgggattg cgtttaaaaa attttTCAGA ttgtttgctg ttaaatataa aaatgctcct   103260
gattttTGTG tgttgatttt tgtatcctgc aatTTTACTG aatttgtttg tcagttctaa   103320
taggttTTTc ttttttggag tctaggtttt tccaaatgta agatcatatt atctgcaaac   103380
aaggataatt tgacttcttc cattccagtg tggatgcttt ttatttcttt ctgttgtctg   103440
attgctccaa ttaggacttc cgagtattat gttgaataac aatggtgaaa gtgggcatcc   103500
ttgtcttgtt ccagatctta gaggaaagcc tttcagtttt tcccttttca gtatggtact   103560
agttatgggt ctgtcatata tggcttctgt tttgttgagg tatattcctt ctatacccag   103620
ttctttgggg ttttttTGTT tgtttgtttt tgagatggag tctcactctg tcacccaggc   103680
tggagtgcag tggcgcaatg ttggctcact gcaagctcca cctcctgggt tcatgccgtt   103740
ctcctgcctc agcctcccga gtagctggga ctacaggtgt ccgctaacac gcccggctaa   103800
tttTTTGTAT tttTAGTAGA gacgggtttt caccgtgtta gccaggatgg tctcgaactc   103860
ctgacctcat gatctgcccg tctcagcctc ccaaagtgct gggattacag gcgtgagcca   103920
ccacgcccgg ccaagggttt taatcataag gggatgtggc attttatgtg atataaatta   103980
tatatttata tcatgtgata tatatttata tcatacacag tataaataat atatatatat   104040
atttttTAGT ctttgtctTT tattctgtta agatgtacca tgtttattga tttgcgtatg   104100
```

```
tcgaaccatc cttgcatccc tgggatgaat cccacttagt catgatgaat gatcttttta    104160
atgtgttact gaattcggtt tgctagtatt atattgagga ttttttgcata atgttcttca   104220 gagacactgg cttctagttt tccctttttg atgtgtcctt tggttttgta tagggtaata   104280
gtggccttgt agaatgagtt tagaagtatt ccctcttcct gtattgtgtt ggaatagttt   104340
gagtaggatt ggtattagtt cttctttaaa ggtttagtag aattcagcag tgaagccatc   104400
aggtccatgg cttttctttg ctgggagact atttcttata gctttgatct cgttacttgt   104460
tattggtctc gttacttgtt attgtatttg ggttttggat ttctttgtgg ttcagtcttg   104520
gtaggttgta tgtgtctagg aatttatcca tttcttcaag gttttccaat gtatcagcat   104580
atagatgctc atagtagtct ctaatgatcc tttgaatttc ggtggtaaca attataatgt   104640 ctccttttc atctctcatt ttattatttg ggttttctct tttttttctg agtctggcta    104700
aaggtttgtc agttttgttt atctcttcaa aacaatttac tgttttattg atcttttgta   104760
ttttcttcat ttcaatttta tttatttctg ctttgatttt ttttatttct tctactgatt   104820
ttaggttttg tccttgcttt tctagttctt taggatgtat tggcagatga agttttttcca  104880 cttttttgat gtaggcactt actgctgtaa acattcctct tattgttgct tttactgtat   104940
cctataggtt ttgataagct gtgtttccat tttcattgt ttcaaggaat tttccagttt    105000
tcttcttaat ttcttcatgg acccactggt cattcaggag catattgctt aattttcatg   105060
tatttgtata cttttccaaag ttcctcttgt tatctagtgt tattttattt tatttttatt  105120
tttgtttttt tgagatggag tctcgctctg tcacccatgc tggagtgtag tggcgcgatc   105180
tcggcttact gcaacctctg cctccccagt tcaagtgatt cttctgcctc agcctcctga   105240
gtagctggga ttacaggcat gtaccaccac tcctggctaa ttttttttttg tattttagt   105300 agagaggggg tttcaccatg ttggtcaagc tgatctcgaa ctcctgacct cagatgatcc   105360
acccaccttg gcctcctaaa gtgctggaat tacaggcatg agccaccgtg cccggcctct   105420
agtgttatct tattgtgatc agagaagata gttgatatga ttttaacttt tttgaatttt   105480
tatttattta tttgtttgtt tgtttgtttg tttgtaacag agtctcactc tgttacccag   105540
gctggagtac atgtcatgat cttggctcac ctgcaacctc cgccttcctg gctcaagcaa   105600
tcctcccacc ttagccttcc aagtagctgg gactacaggc acatgccgtc acatatggct   105660
gatatttttg gatttttttt tttttttgtag agatgggggct ttgcgatgtg tcccagggtt  105720
gtttcgaact cctgagctca agcaatccac ctatttcggc ctcccaaggt gctgggatta   105780
cagacatgag ccactgtgcc acgtcaaatc tttagacttg ttttgtggct taacataggg   105840
tctatctttg agagcaatcc atatgttgag gagaagaatg tgtattctat agctgttgga   105900
cacaatgttc tgtaaatatg tattgggcct atttggtcta tagagcaaat taggtctaat   105960
gtttctttgt tgattttctg tctgaatgat ctgtccattg ctgagagtgg ggtgttgaag   106020
tttccgactg ttactgaggt ctgtttctct tttttgctct aataatgttt gctttatata   106080
tctggatgct ccagtattgg ttgcatatgt atttatactt gttataacct cttgccgaat   106140
tgatcccttt atcattatac aataatcttc tttgtctgtt tttatagact ttgtctcaaa   106200
atctatttta tctaagcata gctactcctg ttcttttctg gttccatttt gcatggaata   106260
ttgttttcca gctcttcaat tttagtctat gtgtgatttt ataggtaaag tgtgtttctt   106320
gtaggcaatg gatctttggt tttttttttt ttttttttga acagagtttt tgctattgtt   106380
gcccaggctg gagggcaatg gcgctatctc agctcactgc aacctccgcc tcctgagttc   106440
```

```
aagcgattct cctgcctcag cctcccaagt agctgggatt acaggcgcct gccaccaagc   106500
ccagctaaat ttttgtatt ttcagtagag atggggtttc agtatgttcg tcaggctgtt   106560
cttgaactcc taacctcagg tgatttgcct gccttggcct cccaaagtcc tgggattaca   106620
ggcgtgagcc accgcaccca gcctttttt taaatccatt tagccactct gtatcttttg   106680
attggagagt ttagtcgatt tacattcagt gttgttactg attagtgagg acttaactac   106740
taccattttg ttacttatta tctggttgtt ttgtagtcct actccctccc ttccccttc   106800
tttttttactt cctcttcgct cctttttttcc ctccctccct tccttgtttt gaaagtgatt   106860
ttctctggtg gtatgtttta atttcctgct ttatatttt tgtgtatctg ttgtaggtgt   106920
ttttgattta agatcaccat gacagctggg tgcagtggtt cacacctgta atcccagcac   106980
tttgggaggc cgaggtgggt ggatcaagag gtcaggagat tgagaccagc ctggctaaca   107040
tggtgaaacc ccatctctac taaaaataca aaacttagcc aggcgtggag gcacgtgcct   107100
gtaatctcag atactcagga ggctgaggca ggagaattgc ttgaacccag gaggcagagg   107160
ttgcagtgag tcaatattgt gccactgcac cccagcctgg gcgacagagt gagactccgt   107220
ctcaaaaaaa aaaaaaaaa agagatcaca taagggttgc aaataacatt ttataaccca   107280
ttattttaaa ccaatgacaa cttgaaactt tgattgcaaa acaagcaag caaagagaaa   107340
actaataaaa actctacact tcatctgccc gcttttaac ttttgttgtt tttatttata   107400
tctttattat actatgtctt aaaaaactgt agttataagc caggcgcagt ggttcacgtg   107460
tgtaatccca gcactttggg aggctgaggt gggcggatca cctaaggtca ggagttcgag   107520
accagcctag ccaatatggc aaaaccccct ctctactaaa aatagaaaaa ttagccggac   107580
atggtggcgg gtgcctgtaa tcccagctac tcggaggctg aggcaggaga atcacttgaa   107640
cccaggaggc caggttgca gtgagccgag agtgcgccac tgcactccag tctgggcaac   107700
agagtaagac tgtctcaaaa aacaatacaa acaaaacaa accctggcc tagtggctca   107760
cgcctaatcc cagcactttg gaaggcaaag gtggggcgaa tcacaaggtt aggagttcga   107820
gaccagcctg accaacgtgg tgaaactctg tctctactaa aaatacaaaa attagccagg   107880
cgtggtggca cgcacctgta atcctagcta ctcaggaggc tgaggcagga gaatcgcttg   107940
aacctgggag gcggaggttg cagttagccg agatcgcgcc actgccgtcc agcctgggca   108000
gcagagcaag actctgtctc acaaaaaaaa aaaaaattgt agttcttatt tttgaaaggt   108060
tcattttta ttcttcctgc tcaaaatatg agtagtagtt tatacaccac aattacagtg   108120
ttacaatatt ctgtattttt ctgtgtactt gttaccagtg agtttttgca ccttcaggtg   108180
atttattatt gtttgttaac atccttttct tgcagattga agaactttt ttttttttt   108240
tttttttga acagagtca tgctctgtta ccagcctgga gtgcagtggt gccatcttgg   108300
ctcactacaa cctccaactc ccaggttcaa gcgattcttc tgcctcagcc tcccaagtag   108360
ctgggattac aagcatgtgc caccacgccc agctactttt tgtattttta gtaaagacgg   108420
ggttttgcca tatttgccag gctggtcttg agctcctgac ctcagggtga tccgcccgcc   108480
ttggcatcct aaagtgctag gattataagc gtgagtcatc gtgcccaact tggttgttta   108540
ttttcaaata gcctgaattc aagctcacta atgtttctg ctgcttgata catttctgct   108600
attgagagac tgatgcattt tcagtttgt caattgaatt tttccacttt gggatttctg   108660
cttgattctt tttactaata attattgcag tctcttttt aaatttatag gattctgaat   108720
ttgttctctg tattatcttg gatttcgttg aactttctca aagcattcag cttgaattct   108780
gtctgaaagt tcacatatct cttatcactt gggaattggt cactggtgtc ctttatttt   108840
```

```
agttcatttg gtgaggtcat gttttctcag atggccttga tgcttgtgga tgttcatcag 108900
tgtctgggca ttgaagagtt gggtattctg ttctttgtag tctggttttg tttgtacgca 108960 ttctttttt tttttttctg tttttgagac agagtctcgc tctgtcgccc aggctggagt 109020
gcagtggcac agtctttgct caccgcaacc tccgtctccc ggattcaagc aattctcctg 109080
cctcagcctc ctgagtagct gggattacag gtgcgtgcca ccacgcctgg ctaattttg 109140 tattttagt aaatatggtg tttcaccatg ttggtcaggc tggtctcgaa ctcctaacct 109200
cgtgatctgt ccgccttggc ctctcagagt gttgggatta caggcgttag ccactgcatc 109260
cggctcccat tcttcttgag aaggttttc aagtattcaa agggaattaa gtgttgtcat 109320
ctaagtcttc gctcactgca gccatacatg cattagaggg caccccaaga ctagtaatgt 109380
tgtgactctg tagaggtatc accttggtag tcttggggaa gatctgggag aattccctgt 109440
attaccaggc agtctcttgt cctcttacat ttctccaaac aaatggagtc tctctttgtg 109500
ctgagctgct tggagtttgg ggaagggtga cacaagcact gccatggcca ccgtcactgg 109560
aactgtactt ggtctcaccc aaggcctgtg gcagctattt tctggccacc actgatgtta 109620
atttaaggcc caagggtgct ttagtcagta ggtgaagaat cctgcaagaa ctgggtcttt 109680
actttcagtg cagcaggttc ccttctggcc cagggtgtgt ctagaaatgc tgcccaggag 109740
ccagggcctg ggatcgggag ctttaggaat ctgctttatt gtactgggc tgagctggca 109800 cccacttgca agataaagtc cttttactc ttctctcacc tcaagcaggt gggtctcccc 109860
atggacacca cagctgtgaa tgtgcggggt catatctgaa gctggcacaa tacgacatgg 109920
caccttgttt tttattcaag gcacaagggc tctttagtca gctggtggtg aatcctacta 109980
ggactaggta tttcccttca aggcaatggg ttcccttctg gtccagaata tgtctagaaa 110040
tgtcatctgg gagctatggc ctagaattga ggcttcagaa ctatgcttgg tgctttattt 110100
tactgtggct gaactagtat ccacattgca agacaaagtc ctccctactc ttccctctcc 110160
tcccagagct gtgagctgtg gtacctggag ttgggggaag gctggcacaa gcactcccctt 110220 ggccacccta gctggtgtct cagtgggtca catgtacccc aagtccactg actatgagcc 110280
cagcacagta ccatgacttg tccaggaatt gcagtccttc tggtctagac tgcctttcaa 110340
gtttatttag daccccagag dacttaccc acggtggtgg ggcttaccaa aattaagatt 110400
cttttggttt tttttggcag agtttcgctc ttattgccca ggctggagta tagtgacgca 110460
atctcagctc accacaacct ccgcctcccg ggttcaaata attctcctac ctcagcctcc 110520
tgagtagctg ggattaccgg catgcgctac cacctctggc taattttttt gttttttagt 110580
agagatgagg tttctccatg ttggtcaggc tggtcttgaa ctcccgacct caggttatcc 110640
gtccgcctcg gcctcccaaa gtgctgggat tacagaccat agtgcccagc cgaaattca 110700 gattctaatc actgggatgg acaattcccc tctgactagg gctagtctaa atactccctc 110760
tgtgggtgct ggctgaattc tgtcctatgc tgctttccac tgtgacaggg cagcactgag 110820
tttcaatgca aaatcccaca gtcatttctc tctctctccc ccgagcacac agattctttc 110880
tccaccccac actgcattgt gggggaatgt caggggtgtt ggaggggcag ttcaagacta 110940
tcttccttat cttttttggt gtcttttcc ttgataggat gtcaaaactg ggtactgtga 111000
tcgcttacct aattttggt tcttatgaag gtgctttctt gtgtggatag ttgttcaatt 111060
tggtgctcct tgttggggat gatcactgga aggttctgtt tggccaccat gctctgtctc 111120
ttctcccctg ccatctcctt tttttactta ggggtttaga atgtctaact gaccaatatg 111180
```

```
tacagtcagg tctcattctg aattcaccta cttaatgacc ttccaagctg actaggccca   111240
gcgcttagtc cagcctccat gacggtccct ccacatccta attagcctcc ctccagttca   111300
tttcacacaa agctgctgtg ttcaccttc tgaactataa atctgcccag tactctaccc    111360
tacttaaaat tccgtataga ctgcccattt gccctgagaa ttaaaagcca aagtcctaaa   111420
cgtagctttt taaaactttt tttttttttt ttttaatttt tagatggagt cttgctctgt   111480
cacccaggct ggagtgcagt ggtgtgatct tggctcactg caacctccgc ctcctgggtt   111540
caagcaattc tcatatgtca gcctcccaag tagctgggat ttacacgtgt gccatcacgc   111600
ctggctaatt ttttttttt atctttagta gagacggagt ttcaccatgt tggccagtct   111660
ggtcttaaac tcctgacctc aagtgatcca cctgccttgg cttcccaaag tgctaggatg   111720
ataggtgtta gccactgcac gcagccctga acatagcttt taagttcctt tattgtcata   111780
ttccttttga cgagtctatc attttctgac tcacttgtac atgtgtgtct cacccttggt   111840
ccagccattg gtgcttttct ttacttcttt atttttgtta ttttatttta ttttattatt   111900 atttttttaaa tgagacaggg tatcactatg ttgcccaggc tggtcttgaa ctcctgagct   111960
taagcagtct gcttgtctca gcctcccaaa gggctggaat tacagtgatg agctactgtg   112020
cccagctcat tggtgctatc tttttttttt tttttgagac ggagtctcgc tctgtcaccc   112080
aggctggagt gcagtggcgt gatcttggct cactgcagct ccacttccca ggttcacacc   112140
attctcctac ctcagcctcc cgagtagcag ggactatagg cgcctgccac catgcctggc   112200
taatttttgt attttagta gagatggggt ttcagcgtgt gagccaagat ggtctcgatc   112260
tcctgacctc gtgatccgcc tgccttggcc tcccaaagtg ctgggattac aggcgtgagc   112320
caccgtgccc ggccccccatt ggtgctattg ttttatgtga tagagccagc ttctcccttt   112380
tctttggatt tttaaacata ctcttccttt tacttagact attctccatc ccaacacctt   112440
tcctaaactt ctttcacacc ttagactagc tgacacttta ctgagaaacc tttctttttt   112500
ataggttgct ttttctatag actctcttag catttactca ttttattgtg aagtgtctga   112560
tcttatttaa atgacaagta taagaggata gaaactatt catatttttc tcacccagca   112620
ggcacaattt ctgacatgtg gtaagcactc agtaaatatt gaactttaga ggctaggaca   112680
tttgagtgct ttggtgactg tggttgtgct atataggtac tctgttattg ttagtttata   112740
gtaaaagcat tactcttaaa gtatgaaaaa agccttattc agaacatttc atgcgtatag   112800
ttaatattac gtagcttgtg ctcatggcaa aaatgtatta ctaaagttat ttaagatatt   112860
taagtataat tgtttccttt atttagttac agccaagttc tacttctgaa tctatggatc   112920
aactactaaa caaaaataga gagggagaaa atcaagaga tttgatcaaa gacaaaattg    112980
aaccaagtgc taaggattct ttcattgaaa atagcagcag caactgtacc agtggcagca   113040
gcaagccgaa tagccccagc atttccctt caatacttag taacacggag cacaagaggg    113100
gacctgaggt cacttcccaa ggggttcaga cttccagccc agcatgtaaa caagagaaag   113160
acgataagga agagaagaaa gacgcagctg agtgagtaaa cctggaactt agaccatcct   113220
gttactcaat taacttttt ttttttaaag gcatttaggt ccttccaact gtgaagaatc    113280
catctggact tttagactac tttatacatt gccttagtt tacaaacagc tagtccaaac    113340
aaatgacatc ttaagtaaat gaggttattg caccctgtgc tactcttctg ttcttcccct   113400
tttttgtacc ccagggctag aaaaacaagg cataaattaa gaaagttttt tctgtaaatg   113460
aacaggagtt gaaaaattat caattcaggg gacctatctt tactggattc cactcattag   113520
tcaccctcac tgtgctgcta ggttgaaaaa ctgccactgt caaggagaga agcatgcggt   113580
```

```
gcttctactt ggaattcaaa atatttttca tcagaaactg tgttttagtt aatgtttaga  113640
tttgttaaga tagacttaat tctgcacatt cagtatatta attaaatgga cttttagggg  113700
ctaacctcag aacttaacta ccattgactt aggtgtttgg gtaccaaaca atccagttaa  113760
agctgaagtt ttggaatgca gcttattgat aaattgggga ctgcttattc ttgatttgag  113820 gcaattttt tttacagcca tgactttttc caggtatgtc atgtaaaata tcttctcaca  113880
taagaattac tgcatgctag aatattggta tgttgactgg tagctcatac ctataatccc  113940
agcactctgg gaggtccaag caggtagatt acttgaggtt aggagttgaa gaccagcctg  114000
gccaacatgt gaaaccctgt ctgtactaaa aatacaaaaa ttagccaggc atggtggtag  114060
gtgcctgtat cccagctact cgggaggctg aggcaggaga attgcttgaa cccagaaggt  114120
ggaggctgca gtgagccgag atcatgccac tgcactccag cctgggtgac agagcgagac  114180
tctgtctcaa aataaataa ataaataaat aaaggatac tgttatgtta agaattgctt  114240
ttaaggatat ttcataagta gctactgtct tttcagctca agtgtttgtt gattggccag  114300
gcgtggtagc tcatacctgt aatcccagca ctttgggagg ctgagtcagg cagatcactt  114360
aaggtcagcg tggccaaaat ggtgaaaccc catctttact aaaaataaat attaaaaaaa  114420
attagctggg cgtggtggca gtctcctgta atcccagcta atcaggaggc taaggcaaga  114480
gaatggctta aactcgggag gcagaggttg cagtgagcca agattgcact gctgcactcc  114540
aacctgagca acagagtggg actctgtgaa ggaaaaaaaa aaagtatttt ttgattgcct  114600
ttgagaggaa cggttgtata ttactcagat tttaaaaaa ttgttctttt atggctgtat  114660
tctttaaggg attaaggaat gggcaatata agtgtatatg tttcaataaa aacgattagt  114720
gatcttctag tgagaacagt ttaaatctat atttagcaat ttttttttaaa ttgtcaggta  114780 tggaagattt tagagcaacg taaagtccat gtagatttca ctggccttta tatttttttt  114840
aggcaagtta ggaaatcaac attgaatccc aatgcaaagg agttcaaccc acgttccttc  114900
tctcaggtag gtttattact ttctttgagg ttatctagtc ccaaaaaaag aaaaattatt  114960
agtaatagtc cttcttccat acctgccatc tgaattttgt tttagtgtgc tgaaccaacc  115020
ttctttcttt tttttacatg gccattaatg aatacttttt aaacattaaa aaaaggtctt  115080
tgttttgtca tcaattagat gtgatcttgg gcaaatcttt gaatttctct gacccagaat  115140
ttgacgatgg ttggctagct aggctgtcag gtttatagat acgtcctctg cacctgaggg  115200
ttttgcatca ctggattcaa ccaaccatgg atcaaaaaca tagttaggat aatctatact  115260
gaacacatgc agacgtttcc ttgtcattat tccaaaacaa tacagtaaag catttacctt  115320
gttttaggta ttataaataa tctagagatg atgtaaagta tataggagga tatgcatagg  115380
ttgtatgcga atactacatg attttatgta agggacttga gcattccaag actttggtat  115440
cttcacaggg tactgtaacc aatcccccac agatactaag agatgactgt actattgtta  115500
ttattcgact gagatcataa gaagatatat ttattttaa ttttaaaaa cacttccatc  115560 agtttcttaa aaatagctgc cactgttttt aatatttttt aattgacaaa gttttaagtt  115620
cctactgaaa catttttct tttattgaaa tgtgaaaatt tatgtgctgt gttttgtttt  115680
tcaataaaag ggacatagtt aaagcaagta aaattagaaa gactgggaaa atccgtcttt  115740
aaattgcaat aatagttcat ctgttacctt gagataattg aatttattgt tgttttgta  115800 gccaaagcct tctactaccc caacttcacc tcggcctcaa gcacaaccta gcccatctat  115860
ggtgggtcat caacagccaa ctccagttta tactcagcct gtttgttttg caccaaatat  115920
```

```
gatgtatcca gtcccagtga gcccaggcgt gcaagtaagt catagaattt gatgttcact    115980
tagcctcccc aattgtttgt atctgacacc aagcactctt taggttttca gtgacttgag    116040
ggtgtgatgg ttatgcatat gcatttgaaa cagacaggca tgcagagatt cagtgtgttg    116100
ttaagtatga ggacctaaat ctgagaatgt tttctgtgaa aaagatggtt tagatttact    116160
gtagtttggg gtttgttcct tttagctgtg ggtatgatct aatttttttaa tgactaatgg    116220
agaatcagga aaccttctca tgcctagctc tctagcaata taaaactaag agtgacagaa    116280
taccttgtta ttatcatagg tgcctaatgt taatttttttt tttaattctc tcaagccttt    116340
atacccaata cctatgacgc ccatgccagt gaatcaagcc aagacatata gagcaggtaa    116400
aggtgagaat aatcctgcct gtgtttgctt gtagtttgca tgctgcatga attgagtaac    116460
taagtttata atgaataaat agttgtagtt tagctctgac ttttttgatga ggctatgcat    116520
tggcttttga tgaacaacat tacatagata ttcacatgga tttttatgaag aaaaacaggg    116580
gagaaaaaat gcccatcagt tgtgattata tagtatcctc ttcaaaaaga gtaattggag    116640
gcctggtgtg atggctcaca cctgtaattt tagcactttg ggaggccaag gcaggaggat    116700
tgcttgagct caggagccca agatcagcct ggacaacaga gactttgtct ctactaaaat    116760
tcaaaaaaat tagctgggca tggtggcata tgcctgtagc cccagctgtt tgggggactg    116820
aggcgagagg atcacttgag cccaggaagt agaggctgca gtgagctgtg attatgccac    116880
tgccctccag cctgggcgac agagtgagac cccgtctcaa acataaatac tggctgggca    116940
tggtggctta tgcctgtaat cccagcactt tgggaggccg aggtgggtgt atcacctgag    117000
gtcagtagtt tgagaccagc ctggccaaca tggcgaaacc ccatctctac taaaatacaa    117060
aaattagccg gacatggtgg cacctgccgc ctgtaatccc agctactagg tggggctgag    117120
gcaggagaat tgcttgaacc cgggaggcag gggttgcagt gagccaagat cgtgccactg    117180
cacttcagcc tgggcaacag agtgagactc catctcaaaa caaacaaaca aacaaaaaac    117240
aaacaaacaa aaaaaccaga ctaattggct ggacacagtg gctccatgcc tgatatccca    117300
gctggaggat gacttgaacc catgagttcg agagcagcat gggcaatata gtgagaccct    117360
atctcaaaaa aaaaaaaaaa agttaattcc aaagcttttt gatctgaaat ctgatttaaa    117420
tctgaactta aatttgaaga agagggtttg ctagattaat ttactagatt gctaaccttg    117480
ctttatatat acctcagtt atttccccaa agccagaatt tcttttgaag cagagggca    117540
actaacttca accaatgtta agatcctatt agaaggatgt ttcggctagg cttggtggct    117600
cacgtgtaat tccagcactt tgagaggctg aggtgggcag atcacatgac cgggagtttt    117660
aagaccagcc tgggcaacat ggcaaaaacc tatctctgca aaaaaaaaat agaaatctta    117720
gccagccgtc atggtgtgct cctgtagtcc tagctacttg ggagactgag gtgggaggat    117780
caattgaaac cagaaggtcc aggctgcagg gaactgtgac tgcaccactg ggctccagct    117840
tgggtgaaag agcgaaaccc tgcctcaaaa agaaaaataa gatggatgtt tctgcattaa    117900
aattagggag ttgtcgtata atgtagttgc ataaactagt attctgtgct tgtgtggtta    117960
aagagccttc gtagaaaaaa tcccacattt ttcttaaaag gaaatctttt ggccaggtgt    118020
ggtggctcac atctgtaagc ccaacactct gggaagccga ggtgggcaga tcacttgagg    118080
tcaggagtac aaaaccatcc tggccaacat ggtgaaaacc cgtctctact aaaatacaa    118140
agatcagctg gcatggtggt tgcgtgcctg ggtgacagag cgagactccg tccaaaaaaa    118200
aaaaaaaaaa aaaagagttc ttttaatgtt ggaaaatgct aaagggtttt tttttgcca    118260
accagttaat ttagagtgat taactgctat cagttgagaa actatagaaa gtagaataat    118320
```

```
ttatacagaa aagacatttc tcagtgccca ataattgcct ttctgacata aagttttcat    118380
ttttcctgaa ttaataagat ttcctcaatg tgttttttg ggtgttttgt gtgtgtgtgt    118440
gtgtgtgtgt gtgtgtgtgt gtgtgtgtgt gtatgtgttt gatacagggt cttgctttgc    118500
tgctgaggct ggaacgcagt ggcgctatca tggctcaatg cagccttgac ctcctgggct    118560
caagcgatcc tcccttctca gtcccctgga tagcggggc tacaggtgca caccaccaca    118620
cctagctaat ttttgtattt tttgtagaga tgggttttgc catgttgcct aggctggtct    118680
caaactcctg ggctcaagcg atctgcctgg ctctgcttcc caaagtgcct gcgcccagcc    118740
aattttctcc atgtttgacc taattgtgat ttcatagatg ttaactaaaa ctcttaattt    118800
tcgttttctc agtatgctat tttttttttt tttagccttg aacatatga acctgttgaa    118860 agaactctgc ctgaaataat gtaatcaaat tatagagttt aatcttattt tgagggcctt    118920
tagaaattct gagaagaaag tgggttttt tttttactgc catttaatg tagtgttaag    118980 gtgttcatgt atcaccagca ggtgtagctg ttttcaatga ttacttaaaa caatgcaatg    119040 ggaactttt gttgtcatta aaatataaaa ggttactgta gtaagagcaa gcatgacagt    119100
ttggctatct gatgggagag tcacattcta acttcaggag gtactgtctt tttaatagaa    119160
atgatatact cagagtctgg gcacggtggc tcacgcctgt aatccagcac tttgggaggc    119220
cgaggtgggc agatcacgag gtcaggagat caagaccatc ctggctaata cagtgaaacc    119280
gtgtctctac taaaaataca aacaattagc tgagcgtggt ggcaggtgcc tatagtccca    119340
gctactcggg aggctgaggc aggagaatgg catgaacctg ggaggcagag ctggcagtga    119400
gctgagatgg tgccactgca ctccagcctg ggtgacagag cgagactccg tctcaaaaaa    119460
aaaaaaaaaa aaaaaatagt agagaaaggg ctttgccatg ttggccgggc tggtcttgaa    119520
ctcctggcct caagtgatcc acctccctcg gcctcccaaa gtgctgggat tacaggtgtg    119580
agccactgct cctggcctga atataccact tttacctatc atcagttgat gaacatttgg    119640
attatttcct ttttctggca atgagtaatg cttttgtgga ttttcatgta caaattttca    119700
tatgaggctg ggagcagtgg ctcatgccta taatcccagc agtctgggag ctgaggtgg    119760 gcagatgact tgaggtcagg agtttgagac cagcctggcc aacatggtga aatcccatct    119820
ctactaaaaa tacaaaaatt acactggcat ggtagcgtgc acctataatc ccagctattc    119880
aggaggctga ggcaggagca tcagaatcgc ttgaacctgg gaggcggagg ctgcagtgag    119940
ctgagatcac accactgcac cccagcctga gtgaaagagt gagtctcaaa aataaaaaa    120000 taaaattttt tttcatgtgg ccttagattt tcatttctcc taaagtagaa atgctgtgat    120060
ggaactgcca aacttttcca aagcagctgc atcattttgt atttctacca gtaatgtaca    120120
agtgttccag tttctccaca tcctcataaa taaccgatat gtctttggtt tgggttatgt    120180
ccattctagt ggttatgaag tgtcattgtg gttttttgtt tttttgtatt gttttgagat    120240
cgtgcccagg ctggagcaca gtggcacaat ctcggctcac tgcagccttc gcttcctggg    120300
ttcaagcaat tctcctgcct caccctccca gatagctggg gctgcaggca tacgccacca    120360
caccaggcta atttttatat ttttgtaga gatggagctt ctccgtgctt cccaggctgg    120420
tctcgaattc ctgagctcaa gcgatccccc tgcgtcagcc tccagagtag ctgggggttat    120480 aggcgtgcac caccgcgctc ggcccatttt tgtatttta gtagagatgg aatttcacca    120540
tgttggccag gctggtcttg aactcctgac ctcaaatgat ccgcctgcct caccttccca    120600
aagtgctgag atttagacg cgaaccacca tgccctgact ataggttatc ttttacttg    120660
```

```
cttgatggtg ttctttgtaa cacagttttt aattttgatg aagttcaatt tatctgtttg    120720 tttttttcttt tgttgctgtt gctcctgatg tcatatcaga caaagcattg cctaactcaa    120780
ggccacagag atttactcct atgaaacgcc tataaaactc ctatgatttt tatagtttag    120840
ctcttaacat ttaagtctac aatctctttt gagttaattt ttgtgtatga gatgagagta    120900
gtggtccagg ttttttccttt tgcttgtgga tatccgttgt ccccacctca tttgttgaaa    120960
agactattct ttcctcttaa attgtttgtt tgtttattta ttttttgagat ggagtgtcgc    121020 tctgatggag tggcgctaac ttagcttcac tgcaacctcc gcctctcaga ttcaagcgat    121080 tccccctgcct cagcctcctg agtagctgga attacagggg tgcgccacca cacccagcta    121140
atttttgtat ttttagtaga gacggggttt taccgtgttg gtcaggctgg tctcgaactc    121200
ctgatctcgt gatctgcctg tctcctggca ccctgggagg ctgagaggct gaggtgggag    121260
gatcacttga gctcaggagt ttgagaccag cctgtaccat tatgcctggc taattttaga    121320 attatctta aagtataaaa tgtgaatcca atttatcttg ttctaaatga ctatccaaaa    121380
tgttttaacc agttttatta gtctgtaatt tacatacaag aaaatgctca tcttttatg    121440 tttacatttt aatgagtttt gacaaatata tttgctcatg taactacttg cttcatcagt    121500
gaagatggaa aacattgtgc ctgttcctct tctctgtcca actgtacttt attaccacta    121560
gctccagtta accagtaatc tgccttcttt tactatagat tagatttatc ctctttagat    121620
ttctttttct tttttttttt ttgattaggt ttttttttttt ctttttttac gtaaaaaaat    121680 cttttttttgg agacgtctca ttatattgcc caggttggtc tcgaactctt gagctcacct    121740
cagcctccca gagtgctagg attacagatg tgagccacct cagccagccc ctagattttt    121800
tttttttttt taataaatgg aatcaaacag cgtgtaacag aggtgttcaa tcttttggct    121860
tccctgggtc atattggaag aagaattgtg ttgggccaca cataaaatac agtaacacta    121920
atgatagctg atgaacaaaa caaaaaaaaa tagcaaaact tataatgttt taagaaagtt    121980
tatgaatttg tgttgggcca cattcaaagc cgtcccagga cgcaagttgg acaagcttgg    122040
tatataattt catatgtgtg tcctaaacag tgtagtaatt tgaatttcat gttagtatca    122100
gcttattcct ttttgtttgt ttgtttgttt ttgagatgga gtcttgttct gtgtcccaga    122160
attggtctgc aattccactg cctcagcctc ccaagtagct gggattacag gcacgtgcca    122220
ccacacctgg ctaattttg tctctctctc tttttttttt tttttttttt ttttttagca    122280
gagacgggat ttcaccatgt tggccaggct ggtctcaaac tcctgacccc aaatgatcca    122340
cctgccttgg cctcccaaag tgctgggatt acaggtgtga gtcaccgtgc ccagccagct    122400 tattccttttt tattgctggg tagcatttca ttttatgatt ataccacagt taatttaccc    122460
attactagtc gatgggcatt tgagttattg ccagcttttg gctattatga atgaagctgc    122520
tgtgagcatt tgtgtacaag tgtttgtgtt tttatttctt ttagttaaat acctagaatt    122580
ggaattgctg aggtatggta agtgcatatt tcattttttt aaaaaattta ttttattttt    122640
tatttattta ttttttttga gatgaagtct cactctgttg cccaggctgg agttcagtgg    122700
cgtgatttca gctcatggca acctccctgt cccgggttca agcaattctc cgcctcagc    122760 ctcccaagta gctgggatta caggcgcgca ccaccatgcc tggctaattt ttttgtattt    122820
ttagtagaga cggggtttca ccacgttggc caggctggtc tcgaactcct gaccacaagt    122880
gatccacccg ccccagcctc ccaaagtgtt gggattacag atgtgagcca ccacacactg    122940
cctggtaaat acatatttca attaataaga aactagcaat cttctaaagt gattgtgtca    123000
ttttacattc caactgatca ggtacatgtg taggttccat gtgttctgca tccttgccaa    123060
```

```
cacttggtat tgtgttatct ttttaatttc aacaggtcta atgggtgtct tatggtatct   123120
cattgtgatc ttaaatgtac atttctctga tgatgactga tccaggagca cctcatcatg   123180
tgtgtgtttg ttttcagctg tcaaccttt tttagtaaat ggttcaaatc ttttttccat    123240
tttatttatt tatttattta tttgatggaa tctcactcta ttgcccaggc tggaacgcag   123300
tggtgccatc ttggctcact gcaacctccg cctcccaggt tcaagcaatt cttacgcctt   123360
agcctcccaa gtagctggga ttacaggcat gcgccaccat gcctggctaa ttttgtattt   123420
ttagtgtagg tggggtttca ccatgttggt catgctggtc tctaactcct gacctcaggt   123480
gatctacctg cctcggcctc ccaaagtgct gagattacag gtgtgagcca ctgcgcctgt   123540
cctaataatt tcttttttgtc tcaatgtttc tgcctgggtg cactggctca cgcctgtaat   123600
tccagcactt tgggaggcca acctggatgg atcatttgag ccaacagttt gagaccagcc   123660
tgaggaacat gacaaaaccc tgtctttgca aaaaaaaaa agaaaaaaga aaattagcc    123720 aggcacagaa gcgcattcct atggtcccag ctactgggg ggctgaggtg ggacaatcgc   123780
ttgagcgagg ttgcgggggt ttggagggcg atggaggggt gatcgaggtt gcagtgagct   123840
gagattgcac tactgcactc cagcctgggc aatagagcca gaccctgtct cacaaaaaaa   123900
agaaaaaaaa gtcatgtttc ttttcttact gtgaaaataa agttactact tttagtaaat   123960 tatttttaagt tatttatata ttctggttac aagtccttc tcagaatatt gtgaatattt    124020
tctcccagtc tgcggttttt tttgaagagc cagtattgtt aattttaatg aagccttatt   124080
tatcaagctt ttctcttaag gttcatgctt ttttgtatca taataagaaa tcttttacgt   124140
accctaggtt atgaatgttt ttatggttag gtatatggtt gatttcaggt taggttttgt   124200
gtagggtgtg atgtaaaggt ctagcttcat tttctccacc ataaatattt actcggtttc   124260
tctggcacca gcctctgttt tccattggtg gctttatttt ttttctgttc ttgaaacaag   124320
agtctcgatc ttgttaccca ggctggagtg cagtagtgtg accttggctc actgcaacct   124380
ccacttccca gggtcaagcg attctgcctc agcctctcga gtagctagga ttacaggtgc   124440
ccgccactac acccagctaa tttgtatttt ttttttttt tttttttagta gagacagggt   124500 ctcaccatgt tggccaggct agtctcgaac tcctgacctc aggtgatctg ctcatctcag   124560
cctcccaaag ttctgggatt acaggcatga gccactgcgc ccagccatag tagctttatt   124620
gaattcagtt gactgtattg tatgtgtgtc tatttgtgaa ctgtttttgtt gtattgatct   124680 ttgtatatat ccttatgcca attctctctt tattgctgtt actttgtaac caacctttaa   124740
gttcatatga gtctcccagt tttattctcg tcaaaattac tcttattctg cgttctttga   124800
atttgcaaat aaattttaga atcagcttgg gattgtgcac tgaatcttta tatcagttct   124860
gggagaaata tcttaacaat atggaatctt cattgaggtc atcatatact gctccattta   124920
tttaagtctt aagtttcacc agtgtttct agttttcttt gtatcagttt tgtgcctgct   124980
ttcttaaatt tatcccttaa tatttcatct gtttgtgct gttgtgagtt atattttaaa   125040
aactttcaac gtttgtttat tcgtaaatag agatgcactt gattttttgaa tattgacctt   125100 gtgtcttgat gtgttggtaa acccactgtt tctggcagcc ctttaagact taaacataca   125160
atcatgatct aatcaccatg ttggtgtttt tgggttttt tttttgtct tattgtactg     125220 gtgcattact gaaaaaggca tgagattttg ccatgctccc attttaggg gtgagacatt    125280 gtctttcact attaagcata cagttaggtg ttacttcagt tcctaatttg cagaggtggg    125340 tttgtttttct ttttaatcat gaatggttgt tggattatgt tcaaatactt atcatctact   125400
```

```
aagtatatca tattgaccag gaacagtggc tcatacctgt aacctcagag ctttgggagg   125460
ccaaggcagg aggatcgctt gaggccagga gttcaagacc aacctgggtg atgtaggaaa   125520
accccatatc tacaaaacaa tttaaaaatt tgctgggtgt ggtggcacac acctgtagtc   125580
ctaactactt gagaggctga ggaaggagaa ttgcttgagc ccagtagttt aaagcagcag   125640
tgagctgtga ttgtaccact gtactccagc ctgggtgaca aaggagacc ctgtatttaa    125700 agtgtgtgtg tatgcgtgcg catagatgga tagataataa tgtaattcca ttatggtcat   125760
acaaactgat atgaaatgcc attttatcat ataacaagtg tcttttttgtg gttgaatttg   125820 tttctggatt tttcactctg cttcactaat ctaataggac taccttctca tccactcact   125880
gccaacattg atttttttt tcagattacc ttgaattttc tgtttatttt tccatatgaa    125940
ctctataatt aacttactac taaaaaaatc agttgccttt ttaaaaccaa ctgatcttta   126000
aaatatatct tggctgggcc cggtggcagg cacctgtaat tctagctact tgggagactg   126060
aggcagaaga attgcttgaa cccaggaggc ggaagttgta gttgagttga gattgcgcac   126120
ctgtactcca gcctgggtga cagagcaaga ttccctctta aaaaaaaaa aaaaaaaaag   126180 aaacagaaaa gataaatctt tttacaataa tttgttccaa ttagggtcca agtcaggctt   126240
gcaatttgga tttgtttata tgttgaagtc tttttttttt tttaattgtt tcatattgtg   126300
gtaacttttt tttttttttt ttgagatgga atcttggctc tgtcacctag gctggagtac   126360
agtggcacaa tctcaactca ctgcaacctc cccctctggg gttcaagcaa ttctcctgcc   126420
tcagcctccc aagtagccca gcctttttt tttgagacag agtctcgctc tgttgcccag    126480
gctggagtgc agtgatgcga tctcggctca ctgcaagctc cgcctcttgg gttcatgcca   126540
ttctcctgcc tcagcctcct gagtagctgg gactacattc gcccgccacc acacccggct   126600
aatttttttg tattttagt agagacaggg tttcaccgtg ttagccagga tggtatcgat    126660
ctcctgacct cgtgatccgc ccgcctcggc ctcccaaagt gctgggatta caggtgtgag   126720
ccactgcgcc cggccttgta tttttaatag agatgggggtt tcaccatgtt ggccagcccg   126780
gtcttgaact cctgacctca aatgatccac ccgcctcggc ctcccaaagt gctgggatta   126840
caggtgtgag ccatcgctct cagccttgcg gtaactttt attacgaatg tattgagaca   126900
ttaataacct aggccagtca tgtttcatcc ctacccattg tctcttaaaa gctttgagtc   126960
cactggatta ttctgaagca aattctagac attgcatcag tttatccacc aacatttag    127020 tgtgtatctt taagttggtt ttggttttgt tttttgtttt tgagatgggg tctggctttg   127080
ttgcccaggc ttggagtgca gtagtgcaat catagctcac tgctgctgcg aattcctggt   127140
ctcaaaggat cctccctcct cagcctctca agtaactgtg actacaggca catgccacct   127200
tgccagcttt tctttctttg tcttgtcttt ctcttctttt gtttttttgt ttgttttttg   127260 ttttttttg agacagagtc tcaccatctt tctatcttgc ccaggctagt cctaaattcc    127320
agggcttaag ttatctttct acctcagcct cctaaagtgc taggattaca ggccagcact   127380
ttaggaggtg ctggatgagc catcacaccc agccaagtca taggtttttt tgtttgtttg   127440 tttttttgaga cagtgtctaa ctctgtcacc caagctggag tgcagtggca tgatttcagc   127500
tcagtgcagt ctctaccaat tgggcttagg tggtcctccc acctcaacct cccaagtagc   127560
tgggactaaa ggtgcgcgcc accatacctg gctaattttt gtatttttg tagagacagg    127620 gtttcgaatt cctgagctca agcagtctgc ctgccttgac tcccaaggtg ccaggattac   127680
aggcatgagc cactgcactc agccctcaca gttttaatta cagttttcc cttagttttt    127740 gtcttgttca tatccagctt gtcttgtatt ttttttccac gatctgaatt ttgctgactg   127800
```

```
tatccctgtg ttgatattta aagtagactt ctgtcccctg taatctttgt aaactgatag 127860
taaataatga aggcttgatc agattgggtt tttttttttt ttccccaatg tttcacagat 127920
gtgtgtactt tcagtgagga gtcatgtaat cagtctttt cctgatagga gtagtcagtg 127980
agttcctaga tgttttatct atccaggaga taatatgtcc ctttagcgcc ttaattttt 128040 tggtgtgttt tttagcagcc attgatgata attgtctagc ccaagatcag ttatttcctt 128100
aggggttgta aaatggtgac attcttttcc tttcatccct tcttcaatta ttgcctggaa 128160
tatttctata aagaaaaact ttcccatatc cagctgtttg gttaccctga ggtatagctt 128220
tcttaggaaa agtaatttaa aatgttaatc atttcccttt ttaaggcagt cttcaaaata 128280
atgagttggt tttctgttat cctccaaagg taaccagtga ggtggttttt ttgtcgttgg 128340
ttcttactat cagtataaac ttctggaatt tttttttttt ttttaattttt ttggagacaa 128400 ggtctggctc tgttacctag gctggagtgc agtgggatga tctgggcata ctgcagcctc 128460
aacttcccga gctaaggcaa tccccccacc tcagcctccc aagtagctgg gactacaggc 128520
aagcaccacc gtgcctggct taattttttgt atattttgca gagacagggt ttcaccatgt 128580
tgcccaggct ggtgtcgaac tcctgagctc aagcagtctg cctgtgtcag cctcacaaag 128640
tggtgggact acaggcatga gccaccatgg caggccagaa tcacaataaa cttataaatt 128700
aacttgagaa gaaatgattg atgtcttcat gatgttgagt cttcctgttc aagaacaaag 128760
tataccttca atagcatatt aaagtttatc cttggctgga tgcagtggct gacgcctgta 128820
atcccacctc tttgggaggc agaggtgggc agatcacctg aggtctggag ttcgagacca 128880
gcctggccaa catggtgaaa ccccgtctct actaaaaata ttttaaaaaa agtattagct 128940
gggtgtggtg tgcacctgta gtcccagcta ctctggaggc tgaggtagga gaatcgcttg 129000
aacccaggag gcagagagtg cagtgagtca agattgcacc actgcactcc agcttgggca 129060
accgagcgac actctgtctc aaagaaaata aataaataaa aataaagttt atctttaagg 129120
ttttgtacat ttttttcagt gtatgcctta ggtaggttct tttttaatgt tagtgtaacc 129180
cagggacttc tcttccattg catcttctaa gtaattactt atgaagtacc atatatgaag 129240
gctattgctg tttatatgtt agttttttacc ctgctccttt actaaattcc aatcctttga 129300
ggtattggat aaaaatattt ttagcatttt tcaaataaca ggcagagtca agggcttggt 129360 ttctttttctt cccctcctgt cccctaccct cccctttttt gagacagggt ctcacttctt 129420
cgccgaggct ggagtgcagt ggtgcagtta cggcttaccg cggcatctgc ctccctggct 129480
gaaaagttcc tcccacctca gcctcctgag tagctgggac catagatgca cagcaccgca 129540
gctggctaat atttttgtat tttttgtgga ggcagtgtct ccccatgttg cccagggtgg 129600
tcccaaactc atgagctcaa gcagtccgct cgccctggcc tcctaaagtg tagggattat 129660
aagcgtgagc cactgcgcct ggcctgggga tcatgtttta acatgagaat tagtggagac 129720
aaacacatga tatctaaata atagcaccat agtatacttg actagctttt taattatttt 129780
ttaaatatac aggaaggtaa taagtaacaa agtaataata gtgaatagtt taagctcagt 129840
tagcataatc gggcaaactt tcatttgata aaagtgataa gtagttttca gtggcttttt 129900
tgtttaccag aaggaggtgg ttttttaaata cgtgcatcca agataaaata taaaaaaatg 129960
ttcaggtttg ctttcctaca tagataaaat aatatgtaac tagctctccc aaatttcagc 130020
aacagttagt gaatgtttag ccacaaattt gcagttaatt atataatcag ttcttaggat 130080
tttatgaaca agttctatat tctttgtgcc ttataccttag ttgtaagcag tcattccaca 130140
```

```
attattttcc tgaagtggct tggttaatgc cacaccagaa acaggtcaca gacaatagtg   130200
ctgtaagaaa tgtgtgagga aagaggcaca tgggaagtag ctagctcgtg ctggaggaac   130260
tggaaaaaaa cctcacatgg gagatgacag ttgagctgaa ttcttaacta gagttgtaac   130320
agggcgaggc ccttacatgc agaccacctg tgtggattaa gataagacat aaagtaatct   130380
tttaaaagaa ctattattta gaaacctggt atatgctaca tggtgctgtg ttatactggg   130440
tttgagaaaa aatgggaagt gttacaagga ttcagtggtt ggaaattaag gaagatagaa   130500
agttagtgtt ggatctgttt tggctctttg gtcatgcctt tgttttctc aaaatgaatg    130560 cagtgcccgt cccagaaaat accatatgag aagcgatttc ataatgctgt gagagtctgt   130620
tacagggact tgatcaagtc tgagggccat gagagaaagt ccctctgagg aagttgcttt   130680
caagctgaca cctgaaggat gaagcagaat tatcccagct gggatttggg aactggtgtt   130740
tgaggctgag gactagcatg catgatagga aaataaccca gagtggcaga agtgggagtg   130800
gtatgagatg gcatcagaga cgcagattca gggtcaaatc attcagagcc tcctagacca   130860
tgtgaacaca tgtattatgc tgtggagata ctgtttaata ggcagtctgc ttttttttct   130920
gcagtaccaa atatgcccca acagcggcaa gaccagcatc atcagagtgc catgatgcac   130980
ccagcgtcag cagcgggccc accgattgca gccaccccac cagcttactc cacgcaatat   131040
gttgcctaca gtcctcagca gttcccaaat cagccccttg ttcagcatgt gccacattat   131100
cagtctcagg taaggctggt aaggcctaac tcttaatttt tgtaccatat aaaaaaactt   131160
ttaatatggt aaagggattt tcctttataa ttttttgcttt tgtgtgatgg tagggtagat   131220
agctaaggac ttggggaccc ttttcaatat atattcgaag gttactgatg attgtaagag   131280
gttcagagga aacagccaag aaagatttga gagtttacag ctgtttctgg aaatctggaa   131340
accatggagt taaaaatctt aactaaagtc tgcttggctc tatttgcagt gttaatgtgc   131400
tttctttatt ttttgtttga acacagcatc ctcatgtcta tagtcctgta atacagggta   131460
atgctagaat gatggcacca ccaacacacg cccagcctgg tttagtatct tcttcagcaa   131520
ctcagtacgg ggctcatgag cagacgcatg cgatgtatgg taggaagcac tttgtttgtc   131580
tcttccagtg tgtgtgactc ttcttaattt aagtttctga aaacatactc tatctaagaa   131640
taacctgacc ttttatgaca ttgagggtca agaatctgaa ggaaaagatg aacccatttc   131700
tttgcctgac ttgctttata acttttggca aatagtttct acttctgtac ctggtcttca   131760
gatctctttc ctgctttaac taaaatgtaa tgatgtatat aatggcaaag catctttgtg   131820
gagaaaggta cctttctcct cttcctcatc aatattatgc tttggtatat cctgcctacg   131880
acatgcaaga gaattttata ataataaaag cataaaggtg ttctccagca tgaaaacatt   131940
ttgcttcact acttgatctg agggtcactg gcattacata ttttttttgc tgtttgttat   132000
aatgataata ctatgtttct acatcatgct gtattttaat ggttgaatat tatgtcatat   132060
tagatatatt ttagacatga gtcacacttt aaatataacc aatgtgaaca gaatgctgaa   132120
atgaaaatga gaagtatttt atgtaaaact aagcagtatt tatatgtgag aataataagc   132180
aaaaaaaccc atcttcgttt tgtgactaaa cagagaaatt tgtgtagatc aacttagcag   132240
ctgtctaaag taccaaaata atagattttt cactgttgat aatttaaaat aaaatgtcca   132300
tttgtatatc ttatgataca gaattaatgg attgcttcaa atgttttca gaatatgttt     132360 ttaaatagta ctgatttcat taagatgttt tgttctgaat atttctgaga actaccgtag   132420
tgtcgtttag ttttcctatt tgcgttttg gttgtttgga gtaggggata attttggttt     132480
attcatacag ttgaaaagtg tactgctatg agaatgagat tatggttaca tgtaactaca   132540
```

```
tgggcatttc attttaaag cctctttgaa cttttgaaa tactaagaat ataaaattt  132600
tattttaa  gtttagatgt cctgaacgag tatgttagg  caaaattgag ttatttaaga 132660
atttataggc tgggcgcagt ggctcacgcc tgtaatccca gcactttggg aggccaaggc 132720
tggcggatca tgaggtcagg agatcgagac cagcctggcc aacatggtga accccatct  132780
ctactaaaaa tccaaaaaat tggccgggtg tggtggcatg tgcctgtagt cccggctact 132840
tcggaggctg aggcaacaga attgcttgaa cccgggaggc agaggttgca gtgagccgag 132900
atcgcgccac tacactctag cctgagcgac agagtgagac tccatctcca aaaaaaaaa  132960
aaaaaaaaa  gaatttacag atttctggca aaccttcttc ttgagacatt actacttttc 133020
ataccacctc tgtccttttt gaagaataaa agttttaaca ttccgtaggt taatgagaat 133080
aggacttggg cagcagcaat catccttcct gtcacctgta acccacagct tatgctttct 133140
tcctggaggt tcttgtctgc cacaaaggct cactgctgat aggaatttgt atatgatcaa 133200
aggtgtttag tttataaaa  cagttaagtc cagtcttaat tttccacatt atcactttca 133260
attttgtatt gtggattacg cattttaaat aaaaaattgt gtgattgcta cattttggaa 133320
aacattttt  tcaagaggcc catccgtaat ttaattgtaa aagatactga caaactaact 133380
tggtttatta ttttggttat gaccccgtca tttgacttgt ctttagttgt cttaacgggg 133440
actgaatatg cgtgcaaagg cacgattgat ttatcatgct ggcttttatg caacttgtat 133500
atattttaac aattttcctg tttgctaaag gcttaggtta aaagttcatt atgattgttt 133560
atacatttct ggtgaataca tcatgattta acaagtggaa agaacatctc tttccttcca 133620
tttctggca  tactcccctt ggaatcagat ctgaaacttt taagctaaaa tttccattgc 133680
atttggagag tagttatttg tgtatgcatg cttttgagac attgtagcaa taatactgta 133740
atgttgagcc gaatctttct cctcattgtg ttcattcact gccaacatct ggcttcatct 133800
tttggatgaa tgttcattgg ttttgaaaca gcctataggg taaatactgt gtttgaggta 133860
cagatgattt tcataactac ttcctagaac atgtccattt gaagagcagt ggggccttag 133920
accccaaagt ccatttatgt gtgggcaaat aggaaatgtt gcaaacaaaa caaagcacta 133980
gatctaatgt ccagtgaaat ctggaatgaa ctagtcatta gagccggttc tttcatgcca 134040
ggaaaaagtt actcagccaa atctgaacta ctctcctgca gtttacacag gtggtattta 134100
attgctgtct gtatgcaggc aggctaggag caaggctgtg gacttgttgt gattgtcact 134160
agttaatcaa gattcccttt gtggtgctta agaccctaaa aaggacacta ggagctgggc 134220
atggtggctg acacctgtaa tccaagaact tggggaggct gaagtggagg atcgcttagc 134280
ccaggtgttc aagaccagtc taggcaagat ggcgagatcc catctctacc aaaaaaaaaa 134340
aaaaaaaaa  aaaaaaaag  cccagtcatg gtggcacatg cctgtagtcc cacctacaca 134400
ggaagctgag atgggaggat cacttgagtc caggactttg aggctacagt gagctatcat 134460
ggcaccactg taatccagcc tgggtgacag agcaagaccc tgtctctatt taaaaaaaag 134520
aaaacataag aaagaattgt tttgttctat gccatcataa gccataattt aatctgctta 134580
agcatgttct tcattaaatc tgcagtgatt tatttgaatt attagacttt caaagcctta 134640
ttatatcaaa tataaacaaa atttgaagta cattcttata aactacaaca aacttacata 134700
gaagtgttaa ttttatactc atcttccctg aacaatttat attttataaa tatattaaat 134760
atattgtaat aaattttctc aaaggaacca aatactttga gtatgaattg tgcttttctt 134820
tttaagctac atcatatcta ggttttaaa  acatttaatg caaacagaag aacatgcacc 134880
```

```
cagatgttgg tgacaatttt atgtcacctt ttctcattca ttaattgtta tagccatagc    134940
caaaggcatt gaaaacatag gaccactaat gactgcaaaa tgaaatcctg attattgttt    135000
ttaaatttttt agtatgttta atacacatat gctaacatta ctgaacagtt aaatgataaa   135060
ataggataat tattttattc taaaaaagta ttgaccttga cctctttcta gctatcttag    135120
aaagggcttt tgtcaaaaac cttatctctt tgatgtctct ttttttgaga tggagtctct    135180
ccctgtcgcc caggctggag tgcagtggcg tgatctcagc tcactgcacg ctccgcctcc    135240
tgcgttcacg ccattctcct acctcagcct cccgagtagc taggactaca ggcgcccgcc    135300
accatgcccg ctaattttt tgtatttttgt ttagtagaga tggggtttca ctgtgttagc    135360
caggatggtc ttgatctcct gacctcgtga tccgcctgcc tcagcctccc aaagtgctgg    135420
gattacaggc gtgagccact gtgcccagcc tcttttttttt ttttttatttt ttatttattt   135480
tttatttttt ttttaattttt tgagaaggag tctccctctg ccacccaggc tggagtgcag    135540
tggcgcgatc tcagctccct gcaaactccg cctcctgggt tcaagcagtt ctcctgcctc    135600
agcctcctga gtagctggga ctacaggtgc ccgccaccac acctggctaa tttttgtgtt    135660
tttagtagag acagggtttc accatgttgg tcaggctggt cttgaattcc cgacctcagg    135720
tgatccacce acctcagcct cccaaagtgc tgggattaca ggcgtgagcc actgccccgg    135780
cctcttgat gtctcttaat ctaacttcca tcattgcctc taccccatcc cttctaagaa    135840
gttactttaa ttttttttcc tctcacatct actcttttt tttttttttt ttttttttg     135900
aggtagtctc actctgtcac ccattctgaa gtgcagcggt gcgatctcag ctcactgcaa    135960
catctgcctc ccaggttcaa gcggttttc tgcctcagcc tcccgagtag gtgggactac    136020
aggtgtgcgc caccacgacc ggccaatttt tgtatttta gtagagacgg ggtttcaccg    136080
tcttggccag gctgatctcg aacttctgac cttgtgattt gtctgcctag gcctcccaaa    136140
gtgctgggat tacagatgtg agccaccacg cccagcctca catctactct tctaatccat    136200
ctaattttgt tttatggtga tgcttttacc tttcagaaac agtaataata caacttttcc    136260
gactaactag agccattagg aagaattaga tccagaatcc ttttttgatt tgttttggt     136320
agtttaatgc agataagtaa gaaaatatag ttaagttaaa aaaaaaaaaa atgaaaagca    136380
tccataatcc ctccacctga caactgcctt ttaacatttt gatgtgtatc cttccaggtg    136440
tatttaaata cactcaaata ccctacccct ttatgtagac atgttttaat aagaaataat    136500
attcatgttt atattcttgc tatgatccta aattttgga tccattacta gataatcttt     136560
caggataatg acatttccat tagtaatgtt tttgcaaaat tgtgtgtcta ttgaattaaa    136620
cttgtaaaat agttttattt tggtacatga tttatatcaa ggttgttcag tagaatgcca    136680
tgttggtgtt tttattagat aatgatttta ttccttttac ttttaagcaa gtcagcatga    136740
caacttgaca cctaagtaca aagaacagt gtcttccggt ttagtccttt ctttttaaaat    136800
tctgtagcag tgtttaaagt gcttgtcatc tcttatgaaa atgaattatg catgaataca    136860
aaaagaaatt actaatatgt caacctttcc agaaatttg gaaatgcac acctcaaaag    136920
gctaatttac ctttctattt cccaaattca gcatgtccca aattaccata caacaaggag    136980
acaagccctt cttctactt tgccagtgag ttgggttttt tatactaatt tttaattgta    137040
cagtaaaaca cttttttaaag gatacatgtt aagggagtag acttgttgaa caatattttc    137100
cttgtgccag tcaaattatt gaaagtactt atatatataa ataattcagt ttttaaaatg    137160
gaaatacccca atttaagaag gctggagtta atgaaaaatg gagttgtttc agaaatcaat    137220
ttttgcatac caagcaaatg tgactgggaa atgcctaata ttttccttgt tagagaaact    137280
```

```
tcctaaacag ctttatacac acacacacac acacacacac acacacacac aaacacacac    137340
acccaagcca caagcttggt ataaatttaa aatgtttatt tatacacaca cacacacaca    137400
cacacacaca cacacacacc ccaagccaca agcttggtat aaacttaaaa tgtttattta    137460
tattctgata agatgaaatt tatgcctacc aggatttta attgaatagg attgatgaaa     137520
tactaaggga aaaacttttc agtcctgtgc atggctaaag gtttaaaata ctcaggaagg    137580
gccaggcacg gtggctcaca cctgtaatcc cagtgctttg ggaggctgag gcgggtggat    137640
catctgaggt cagcagttca agaccagcct agccaacatg gtaaaactcc atctctacta    137700
aaaaatacaa aaatcagcca tgcatgctgg catgcgccta taatctcagc tactagggag    137760
gctgagacag gagaattgct tgaacttggg aggcagaggt tgcagtgagc cgaagtcgtg    137820
ccactccact ccagcctggg tggcagagcg aaattctgtc tcaaaaaata aaatattcag    137880
gaagcagacc cctcaggata tcttgagctt aagcaagaga tcatgacctc tcaggtcatt    137940
atcttggaca gcacaggtcc cctctcccca cctggcaaaa agtacagaaa tagttgctcc    138000
ttcatggaga aagtctgggc agagctttct tctggaaatg aacttttaag gtacatttt     138060
cctatttgta gggcaattg taaaaataag gccggacgt ggtggctcac gcctgtaatc      138120
ccagtacttt gggaggccga ggtgggtgga ttgcttgagg ccaggagttc gagaacagcc    138180
tggccaacat ggtgaaaccc tatctctacc aaagcatggt ggcacgcacc tgtagtccca    138240
gctacttggg aggcggaggc acaagagttc catgaaccct ggaggtggag gttgcagtga    138300
gctgagattg taccactgca ctcaggcctg ggcaacagag agagactctg tctcaaaata    138360
aaaaataaaa ataaggctag tcttggactt tggtatttaa ataggaagga gtactaatat    138420
ttgtagaaat cctttagaaa tttgtgccat taatattgtc accttgtatg aaatgttgtg    138480
ttctagagga tattaaggat tcaaatttta tgttaggcac attttgagtt attttggggt    138540
gactcaatgt ctgactctac taaatgccat attagcattt aaaatgcatt tgaccttaaa    138600
tctttgttaa ttatgccatg acttggtatc caaaaataag ctgatacata catacataca    138660
tatatgtgtg tgtgtgtgtg tgtgtgtgta tatatatata tatgtatgtg tgtatatata    138720
atttatttgg tgctaggaaa tgttaaattt aatcctttaa tagatgctct ttaaaaagga    138780
gtcttgctgt atgtatatac tattaaaggg gaaactatgt ctgtgattgt agtgtgtaaa    138840
agatagtagg tgatttatt atgtactcaa tttgaggtct caaatgtagt tatcctcacc     138900
atcttactgt ctctgttagt agtttggtgt tgttttcctg gtaagtagct aaggtcctta    138960
atcattaaca cctaagcctt aattgcctta gcacaacttc ccctaaaagg gagtatcagt    139020
acttttaaa agaaactaac agttgggctg ctaatttaat ctgctgcttc atttcccct      139080
gttctaagcc attttatgat ggtttggtca agttgccttt tattcccctt ttagagtttt    139140
caactttcct tcacttccct ttttctgaat ttaacatcag atttacaagt tggaagattt    139200
tgttttgttt tataagtttt gcaatgctgg tgatctctta tgacttgtgc atccaaagtc    139260
aaaatgacaa aacctagtta caaattaaac acacagcttt ctgtacttaa tttgcttcag    139320
tgagatcaca gctgaggaaa ctagttctgg aatgtggtta gtgttattaa ggatttttga    139380
ctgatcatat gtttagaatc ttaaatattt atgtcaagga acactgagtg ggaaacttct    139440
ggactaggtc tggaccaaag aagcatatgt ctttgattat cttaatctaaaa agattta     139500
tgaagactaa agttttataa atagaagttt aactgatgaa taaatcagta ttacaaataa    139560
aattaacttt attttaacc tctctgggat ctttagccag aatgagcata tataacaaaa     139620
```

```
gcagtgaaat aatatgtgtg ggtcagaacc cactgcccct cccactccac tctccttttc 139680
cctgattctc ctgtgttttt tccttcttta ccttatcttg gttccttttt tttttttttt 139740
cttttgagat ggagtctcac tctgtcgtcc aggctggagt gcagtggtgc gatctcggct 139800
cactgcaacc tccgcctcct aggttcaagc aattctctgc ctcagcttcc agagtagctg 139860
ggattacagg cgcctgctgc cacacccagc taatttttt tgtattttta gtagagacag 139920
ggtttcacca tcttggccag gctggtcttg aactcctgac ctcgtgatca cctacctcgg 139980
cccctggttc cttttttgtc tctcttgtct tccaagctat ttttttcctt ggcttttaaa 140040
ttttcttcct accctgcttt gtgtcactgt cacttaactg gcctatcaag gaaccgaact 140100
gtattttgt tactagtatt gatttaaagt ataagtttca catttctccc aatttattat 140160
tattatttat ttatttatttt gtttatttta tttttgaga cggagtttcg ctcttgttgc 140220
ccaagctgga gtgcaatggt gtgatgtcgg ttcactgcaa cctccacctc ccggttcaa 140280
gctattctcc ttccccactc tccctagtag ctgtgattac aggtgcctgc caccacgccc 140340
agctaatttt tgtatttta gtagagacag ggtttcgccg tgttgccaa gctggtctcg 140400
aactcctaac ctcaggtgat ccgcccgcct cggcctccca aaatgctggg attacaagcg 140460
tgagccaccg tgcccggctc catttctccc aatttcaaat tcaaggagga aaagaattcc 140520
tgattaaggt acttctttca gatcttttga gctagaacaa aaaacaaag ggaaatattt 140580
ctaattaact cttttaaat tttgtttaca acgtatgata catattttac acatcctttg 140640
tggttttgt tcgtcttgtt tttaatcaat gccttgcaag tttaccggta tttaggtagg 140700
gaaaggattt tgttttgtt tttttaaaca agcctatgt acattcactc agcttgggta 140760
tttgtgctat gcatgcaaat tagctataga ttagaaaacc gtattatagt ctttaaatac 140820
tggtaaactt aaattgcaga gatgcctttt aaaaatgcat agtaaaaata tttcatcttt 140880
actttctct tcaaatgatt ttaagatttt tacattttc cagttgatga ataacttaaa 140940
ttatgagatt tcatgggcat aattattttc tatatttatt gttactttttt aatattctta 141000
atactttgct tagaaggtat ttaaaagtga aatttcaaac ttttttagtac aaaatttctt 141060
gaataaataa agttacaaaa aaaaaacaaa aacctctgag attccgtact gtatcttat 141120
gaacctccat gaacagaatt tgggatttgg gaattgcttt tccttagaca gatttagatt 141180
gttacaaatg acattttaa gaggctgggg tggcggtagg ggttagtgct aatgttaa 141240
cagtagggga ccatggacaa ctgtagacat cactatccag tagaacattt tgtggctggg 141300
cgcggtggct cacgcctgta gtcccagcac tttgggaggc caagacaagt ggatcacctg 141360
aggtcaggag ttcaagacca gccagaccaa catggtgaaa ccctgtctct actaaaaata 141420
caaaaaagtt agccaggcgc gcctgtagtc ctagctactc aggaggctga cacaggagaa 141480
tcgcttgaac ccgggaggca gaggttgcgg tgagctgata tcacgccact gcactccacc 141540
ctgggcaaca gagcgagact ccgtctcaaa acaacaacaa aactgcactg tccaccgtat 141600
tagctactta gctacatgtg gctttttat tattcaaaaa taattttta ggccgggtgc 141660
agttgctcac acctgtaatc ccaacacttt gggaggccga gatggacgga tcacttgagg 141720
ccaggagttt gagaccagcc tggccaacat ggtgaaaccc cgtctctact aaaaatacaa 141780
aaattagcca ggtaatccca gctactcaga ggctgaagca ggagtatcac tttaacccag 141840
gaggcggagg ctgcagtgag ccgagatcgc tccactgcac tccagcctgg gtgacagcaa 141900
gactgggtct caaaaataaa caaacatggc cgggcgcagt ggctcatgcc tgtaatccca 141960
gcactttggg aggccgaggc ggatggatca cttgaggcca gtagttcgag accagcctgg 142020
```

```
ccaacatggt gaaacccgtc tctactaaaa atacaaaaat cagccaggca tggtgatgct   142080
tgcctatagt tccagctact cggcaggctg aggcaggaga atcgcttgaa cccgggaggc   142140
ggaggttgca gtgagccgag atggtgcccc tgcactccag cctgggcaac agagcgagac   142200
tctgtcaaaa attaaacaaa taaatacatt tttaaaatga acgtaagatt tttacaagta   142260
caacaaactc aggttcgaaa tttacatcaa atcttttaga ccaagtcagt gcctatacaa   142320
cttggaggag ctggaagtaa acttaatgag tatgatgatg atggagggcc tgttaataag   142380
ccaccaagtt agaaaaaaag gactgtctta tagacttatg ggactgtgaa gctcaggaag   142440
gcttcatcgt ttgtacatca tttgttctag ctcccagaag acgttcacta ctcttaaaaa   142500
cattcagaga ctatgttgcc acagttttct tgttaaaata ttctggcata tgttaattcc   142560
tacagtctgg aaaattttcc cagtgtataa acaaagctgc tgtatccagt ctaaactgga   142620
tatgaaggaa tattaatgcc agctgtggca ttggcagtgg atgcacaggt gatcctagaa   142680
ctggctcttt gccttgccct ttcccctgct aagagatagc tttgcagctg gagacgtaac   142740
tgttagggct ggagagttgg tggcccttag ccctacaaca cctaggatta tagaactgct   142800
ccatgtgcct agcctaaccc tctgcacacc atttacgtgg aatatacccca gagccgtcta   142860 tgctggtgac tcggcagcct tgcctaccag actgctggaa ctagggtgcc tcttcccaaa   142920
gctgtgcttg cttctctcac caatcagtcc tgcatatgtc tgtgtttgct aacacgttat   142980
atgaagaatg tggggaacta ttttggaatc atttctgtgt atgggcttat tatcttgagg   143040
gattttagga tttgtttctc aagagagggc tgggaactat accttgctag agttgtcttg   143100
agaacgctct attctcagct cattgcctcg tggaggttag tttttttatca tcggtgtgct   143160 gtccatagtc actggaagca gtgaacacat cctactctgc ttctgattct caacttactg   143220
tttttgaagc acatgaacag gccaggcacg gtggctcacg tctgtaatcc cagcactttg   143280
ggaggctgaa gtgggcggat catttgaggt caggagtttg agatcagcct ggccagcatg   143340
gcgaaacccc atctctacta aaaatacaaa aattagctgg gcgtggtggc acatgcctgt   143400
aatctcagct actcgggagg ctgaggcagg agaattgctt gaacctggga ggcagaggtt   143460
gcagtgagcc tgggcaacag agtgagtgag acttatatct caaaaaaaaa caaaaaacaa   143520
aaaactgaaa gacatgaaga aatggttttt gtaccaaggt ttggcccacg ctgagattca   143580
caaagaactg gctttcagtt cttatcttta ttttgattta aactggccca tcatgttgtc   143640
ctttgaagtt agtctagtaa atttctttcc aaagggctgg ggcactcaga agggagttta   143700
cttttctata tttatttcat aaagcaaaga tgggagatcc tccattaggg cttgggaaag   143760
taaactgagt ggcagaaggg ctcctgtgat tagctgagag agactgtggt ccttcggccc   143820
tgatgataga tccctggcct tgccacatac catacacagt gcccgcaccc catccccca    143880 ccacacccaa tatagtctgt gccctcagga cattgctcca gggcagtagc atggtgaggt   143940
tagcctgatg atggccttga gctaaagagt gtgcacctaa aatgcacttg tttgagtagt   144000
ttctgcctat gccttcaagt tgccttttg ggaaaaccta gtgaccgtta agagtaaatg    144060
caaactaatt tgattttaat atcatatgta gagctgtatt atatgaacca aatgctagtc   144120
tgttaagcaa tagctacact tattttttca agacaatgga tggtttaaat ggagtcatct   144180
atagaaattg gtagtggcgt gagttatgca ttgtaaccat caagaaagtt cagttgatga   144240
agtgtagagg agcgatggag gttgtcagac atccggttgtg tacatgctcc tttttctttc   144300
actttagttt ccacgggctc ccttgctcag cagtatgcgc accctaacgc tacccctgcac  144360
```

```
ccacatactc cacaccctca gccttcagct accccactg gacagcagca aagccaacat 144420
ggtggaagtc atcctgcacc cagtcctgtt caggtaaggg caactcagag gtctgcatgg 144480
agtggcttct ttatcctagt atctgagtgc tttcttcagg tgccaggtat cgcatcgtca 144540
gaacacatgg catgtccacc ctcgtgaaga tggatacagc tgtgccctg gggtggtggt 144600 tttaagaatc acatttaaag gctgggcgca gtggctcacg cctgtaatcc caccactttg 144660
ggaggccgag gcgggtggat cacgaggtca ggagattgag accatcctgg cgaacactgt 144720
gaaactccgt ctctaataaa aatacaaaaa aattagccgg gcgtggtggt gggcgcctgt 144780
agtcccagct tctcgggagg ctgaggaagg agaatggcgt gaacccggga ggcggagctt 144840
gcagtgagca gagatcgcgc cactgcactc cagcttggac aacagcgaga ctctgtctca 144900
aaaaaataaa aaattaaaaa aaatcacatt taagatacat gttgataata aggtgattgg 144960
ataagctctg gaaacttgca gtaatgaaaa atcaaattta acataaagtt cataaggcaa 145020
attcctattt gcttgggact ttttaatttc taaggtttat gtgatgaggt tattttccta 145080
tgagcttctt gaattatgtt tgctaatgga ggcagttaaa gatgtctttg atatctatca 145140
gttccctggg gcagtagtct tttttgactt tagtatgtat gctcagaagt ttctaactgc 145200
cagactgaga atcaggcttc tgtaccctag aaaggagttg tccagatggg aggcacctcc 145260
agccttgctc ttaccaccct gtacattctc ctgtactttc cagtgaccct catcataggc 145320
ccaagtgtgc aaagcttagc tttgtgggta tcccttggct gcttttcatt aaagaagttt 145380
tcctctcaat tctttcctgt cgctttgcag caccatcagc accaggccgc ccaggctctc 145440
catctggcca gtccacagca gcagtcagcc atttaccacg cggggcttgc gccaactcca 145500
ccctccatga cacctgcctc caacacgcag tcgccacaga atagtttccc agcagcacaa 145560
cagactgtct ttacgatcca tccttctcac gttcagccgg cgtataccaa cccaccccac 145620
atggcccacg tacctcaggt aataccagct ttagccaact ttctgtgaag gccaagtaga 145680
atgtgaaggt tatcagtaag cagctagagg ctctcccagc taggaaaccc tgtgtgtcat 145740
gccatttgcc tgtctcccct tccctctcaa atacacgtga tctggcccta agggaatgtt 145800
tgtgtggttt tgtcatggga tcagtgaagg tgctgattgg tcagtccttt agttttccaa 145860
ctgagacctt aaaaatatct ttgactctgg aatgcaaccc agtccttctt tccttttctgt 145920 gtctgctttg ctatgtctat atagcctcac tactatatat atgtgtacat atatattccc 145980
ctacacactt accttggaag ccaggcaggg atgatggcct tcacagagtc tcagctctcc 146040
gaagtgacta ccggggcctg tcaacttgat tgttactcac atgagttcca gacacatctc 146100
tccaattgtt ttccctggtt atccatatat ctgctttgac cataagttgt actcttgaga 146160
gggcttggcc ttggacattg gtgcagtgta actagaagct ggaagcaccc aggtggtccc 146220
attttctttt aagagcagcc ctggaagcac tttggagctc acctccagtg taagctgcta 146280
caggtgaaag gtgtgcttgc catctcagtg gttgctgtct gcatcagctg ctgacaaagg 146340
tccctgcact ccagggccca ggggattgtc ttaatgagga gaaggagctg cactgaagtt 146400
gggctctaac gctggccttg aggccctccc tggggctgtt acgggtgaat tggctgtatt 146460
agatgtctct gctactttca taacagaact ctctgaggcg gtctaagtg agacctgcca 146520 caatgaattc catttcctgt taaatagtgc gccagtgagg ctctggcaag gtgtgggcta 146580
gagatgcgac tcagtggat ctatctctca gaaggctacc ttgtaagtag agttccacag 146640
ctctgggaag tttgggcgtc ctcaccctgc aaagtttagg ttctgtggtg tagcgcactg 146700
cagttgattt gcttttttgat agtggggagg gaagccggtt tggtccgtgt gggccagcgt 146760
```

```
ggtttggtgg agtcagcttc ataagagctg gggtcctgta ggtgtctacc agaggctggt  146820
ggctaagtag gcatgtgaac ttacatgtaa gtcagggatc cctaaaacct cactctgttt  146880
ttgtgctgaa agggcaaaaa ggttaacaca gggaagctca aatttgccat gtgcccgttt  146940
gaatatgtga gagtaaaaac ggcatttcat ccaaggctta tcgtagtcta gaacagtgca  147000
cagtgtggga aaaggaaac  aagggctctt cctggccctg ccaacccccct gcagagctgg  147060 aatccagctg tttgggctga ctaaaatcac ctttccaact tgacagtgag tgagaccagg  147120
ttgaacttgg tacagagacg ctgggctggc ccagatgact tcaggttact cctttccatc  147180
tcactggagc cattaaaaac tccaactcct cctcctcctc ctgctccatc agcatatctc  147240
tgagagagtc acgggggcct aagagtctct tttcactgcc tggtgagcag accagaagca  147300
gagggagaga ggcaaatgaa cagaggtcca agtaattcac atacttgact gtgacagtct  147360
ctgcttatta atgtaatctg ttttcctatt tgaaagggat gttatctgca aaactacctc  147420 aggcccaca  tggcagcctg attctgaagc atcattgaat cttgtatgat attaagttga  147480
gaaagctgcc cttggatcca gtgtctaatc tttgtgaaga tcttacccca tacatagaat  147540
acaatgatca gaaatgtcaa gggttaggac agcacagccc tgacttctac ccaggctcac  147600
ttgttgcctg ctccctgacc cttgcaggat ctgcccaaag gtgaagcgcg tcttcaggtc  147660
aatagataat ctactagaga ttgtccccag agaacagaac tgggccctga ggcccaccgt  147720 tgcccttttcc tgagagtccc agcccagtga aggaacaca gttgacatgt tgttgaagcc  147780
ggagatgttg cctgtatgcg taaaagagct ctctgtttca ggctcatgta cagtcaggaa  147840
tggttccttc tcatccaact gcccatgcgc caatgatgct aatgacgaca cagccacccg  147900
gcggtcccca ggccgccctc gctcaaagtg cactacagcc cattccagtc tcgacaacag  147960
cgcatttccc ctatatgacg caccccttcag gtgaggcgtg tgtgtgcagg ggccgccggg  148020
gcaccccaaa gcattctgct cgcacaggtg gaatggcagg cagggccagt gcttcaagcc  148080
ccgcatttga gaactagcaa gacccgtcca ggagtgtgca caggagggac tgtgacgatc  148140
agttcagcat cagggcctga ggcttccggg agccgagtct gtgtgtgttc tgatggtata  148200
caggatttgg cttgatgaga agcagcagca gcagcaacag cagcctgatg catgcctagg  148260
actcagttgg ccttccttgt tatgacaggc tggacagggc agtgttttcc ttcctgagtc  148320
ccaaaagtct gacatgtggg gggttattac catggcagag tttgattgta gctctggaga  148380
agatactgct gagaaagcgc tgtggatgga ctggctttga gtgtagcgtt agccccagcc  148440
cctgaacagg ggagagcgcc ctgtgattgt gctctactac ttgatggctg ccatggcgat  148500
acttcacagt ctgacctgtt attctgaaag caatactggt gcttggctaa tatttgggga  148560
gggggtttgt taaggccttt ttttctaccc catgaacaag tcttctggga gttttatctg  148620
aagtggtttt acgtctgact ggtttgtttc tacccaccca cccaaccctc cccactttgg  148680
tgcagatggg aggggaaaa gcgaattcaa ttttgagttt tgttcagcta gcacgaggat  148740
agtttacaat catgtgctgc agagacacta ggctgatgtg tggtgttgcc agttttctgt  148800
ttcaatgttc gcttttcttt ttacagtaca agcccaccac caacagcagt tgtaaggctg  148860
ccctggagga accgaaaggc caaattccct cctcccttct actgcttcta ccaactgaa   148920 gcacagaaaa ctagaatttc atttattttg ttttaaaat atatatgttg atttcttgta   148980
acatccaata ggaatgctaa cagttcactt gcagtggaag atacttggac cgagtagagg  149040
catttaggaa cttgggggct attccataat tccatatgct gtttcagagt cccgcaggta  149100
```

```
ccccagctct gcttgccgaa actggaagtt atttattttt taataaccct tgaaagtcat    149160
gaacacatca gctagcaaaa gaagtaacaa gagtgattct tgctgctatt actgctaaaa    149220
aaaaaaaaaa aaaaaaatca agacttggaa cgcccttta  ctaaacttga caaagtttca    149280
gtaaattctt accgtcaaac tgacggatta ttatttataa atcaagtttg atgaggtgat    149340
cactgtctac agtggttcaa cttttaagtt aagggaaaaa cttttacttt gtagataata    149400
taaaataaaa acttaaaaaa aatttaaaaa ataaaaaaag ttttaaaaac tgatcaagtt    149460
agtgtgtgtc tgtataagct acttctttgt aggatactta atatcaaagc aggtgtgcta    149520
agggtgcatt ttgaatatcc cggaaggtag ctgtgaaatg attttctc  ttcaccctta     149580
gttctggttc aaggtatctc tagaaaaaga caagactgag ctattctctt tggtggatta    149640
gagatctgct tcaggaggag gaaggttggc cagagttggg cagcactgaa attccacatc    149700
ctcgggctga caccgattct gtaagcttcc tttttaatat ctcctgaacc aaaatgagtg    149760
tcattagctg gaagttccca attcgggcat ttttctactt taccagtagg gggcaggaga    149820
cactcagaaa aaaattgcaa taagaaatc  cagagggcat gaaggctgaa aagatacaaa    149880
gatgtacaaa gctgcttatt gacatggatg gactcataag catttgttag tattcccaga    149940
ttgcaacggg gaggacaaag ggaagagcga gtatttgggc agggcaagga ttttgtagag    150000
acaccatggt cttaatagag cctttaaata ttatgacagc aaatcaagat tctgaaaact    150060
ttttaattca catatagcaa tttgtacatt atagcaaaat ttgcattatt caagaataag    150120
ttacttgtac agtacataaa acaatacata aaaatttgcc aaatacccttc tgcctataat    150180
gatacaagat gaatccactt tatgttatca caatgtgctg tatattctaa ccaaacacag    150240
gatgtcagat gtgtccttgt taatatactc gcaagttcct ctagcttgtg ggagatgtta    150300
gagctaacac atttgcagta agggacttag tcctgaatag aaagcatgaa ggaatctcag    150360
gcaaccctca gggaagagtc caaggccttg actttaggtt aagaaactgt tatgtaaaaa    150420
tagtgttctc tggcccaaga ttttaatgat tgctattcct ttttcctacg gtccagaaat    150480
gatcaaaggc agaagattta taccagataa agccatatgg attgctggtc taaaattcaa    150540
ggcaggttag ttgacttaat tctttggtgc tggtgactgt tagtttgtaa aagttcaata    150600
agtcagatga aggaagggat ggtgccggga gctgtcaagc tgtactggtg gggtctgtaa    150660
ttagagctaa ctgagggat catgatgtct actgtccagt ttggtgttga gccatggctc    150720
tcggtagaag ttgccggctg gggcctggtc aggactggaa ggagagtggt gggatgtgct    150780
gtgcctatgg tgggctagct gcagccagtg gggtgcctgc cccacactgc tgcccacccc    150840
ttcatcagct gattctgctc ccacataaag aaaggtgttg gcttagtgtc acttcttcct    150900
agagccatgg gagttttctg tcagcatgtt tttgagctgt cctggtaact tggacgggaa    150960
gcagtctgga ggtgggtgcc ttccaaatct ctgccacaga a                       151001
```

<210> SEQ ID NO 3
<211> LENGTH: 863
<212> TYPE: DNA
<213> ORGANISM: homo sapiens
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature

```
<222> LOCATION: (50)..(50)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t

<400> SEQUENCE: 3
gtctgtcggg gctctctccc cgccccctcc ggatcctggg naagnacggn ggacggggtg      60
gagacaagtg ggccttggcc cccgcacccc tctgcgttcg tgtccgaggc ggcggcgggg     120
gctcccgaac tcccctgaaa tcgtggggct ccatgtggcc tccggcagcg ttccaccctc     180
ccccacctgg ggaagggaag gggtgggggag tgcccggccc cgtcccggcc ttcctccttc    240
ccccgccaga cctctccggc gcgcgggtgg tggccgatcc gcattgctgt tcgaggccgc     300
agtggagaag gcgcctgtgg aacatcgagg tcgaaacagt aacaaaggac tgcctcagtc     360
tacgatttct tttgatggaa tctatgcaaa tatgaggatg gttcatatac ttacatcagt     420
tgttggctcc aaatgtgaag tacaagtgaa aaatggaggt atatatgaag gagttttaa     480
aacttacagt ccgaagtgtg atttggtact tgatgccgca catgagaaaa gtacagaatc    540
cagttcgggg ccgaaacgtg aagaaataat ggagagtatt tgttcaaat gttcagactt     600
tgttgtggta cagtttaaag atatggactc cagttatgca aaaagagatg cttttactga    660
ctctgctatc agtgctaaag tgaatggcga acacaaagag aaggaccctg cagcccctgg    720
atgcaggtga actcacagcc aatgagggaa ctggaggctt tgnaaaatga cgtatctaat    780
ggatggaacc caaagatatg tttcgtttaa tgaaaaaat tatggcgcag gggccaccgt     840
tgaaagcagt ttatttcgga tac                                             863

<210> SEQ ID NO 4

<400> SEQUENCE: 4

000

<210> SEQ ID NO 5
<211> LENGTH: 27
<212> TYPE: DNA
<213> ORGANISM: Artificial sequence
<220> FEATURE:
<223> OTHER INFORMATION: Primer

<400> SEQUENCE: 5
accaaagagt agttaatgga ggtgttc                                          27

<210> SEQ ID NO 6
<211> LENGTH: 19
<212> TYPE: DNA
<213> ORGANISM: Artificial sequence
<220> FEATURE:
<223> OTHER INFORMATION: Primer

<400> SEQUENCE: 6
agaaggtggg cgagaggaa                                                   19

<210> SEQ ID NO 7
<211> LENGTH: 19
<212> TYPE: DNA
<213> ORGANISM: Artificial sequence
<220> FEATURE:
<223> OTHER INFORMATION: Probe

<400> SEQUENCE: 7
```

```
ctggccatcg ccttgccca                                                  19

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccggctcgca cgccgggcgg                                                 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
catacaccgg ctcgcacgcc                                                 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ggcttcagcg acatggtgag                                                 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cgacctctgc ccaggccggg                                                 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 15
tgcatagatt ccatcaaaag                                          20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
aagtatatga accatcctca                                          20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttcacttgta cttcacattt                                          20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tctgtacttt tctcatgtgc                                          20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ctggattctg tactttttctc                                         20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ctctccatta tttcttcacg                                          20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tctttaaact gtaccacaac                                          20

<210> SEQ ID NO 22

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gagtcagtaa aagcatctct                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
cagggctcca ggtccttctc                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gcatcccagg gctccaggtc                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tcttcattat atcgaaacat                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gctaactggt ttgcccttgc                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gtatttttct tcctcactcc                                              20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
```
tgctgtgtat ttttcttcct                                              20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
gaaatctgaa gtgtgagaag                                              20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cctccattaa ctactctttg                                              20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ggaacacctc cattaactac                                              20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ggcgatggcc agggaacacc                                              20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
gtagcgagaa ggtgggcgag                                              20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
agagttggga cctgactggt                                              20

<210> SEQ ID NO 35
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 35
tggaagagag ttgggacctg                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ggagctggag aaccatgagc                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gagacaggag ctggagaacc                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ttgtgggata caaattctag                                               20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ggaaccccac tgaccactga                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tcttgaagcc tggaatcttt                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aacctaaaat cattcttaaa                                               20
```

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
agttgatcca tagattcaga                                          20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ctggtacagt tgctgctgct                                          20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctgccactgg tacagttgct                                          20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tttgcattgg gattcaatgt                                          20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
gaaggctttg gctgagagaa                                          20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gtagtagaag gctttggctg                                          20

<210> SEQ ID NO 48
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 48
tgacccacca tagatgggct                                               20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggtattgggt ataaaggttg                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gtcataggta ttgggtataa                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ggatgctgag actgataatg                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
acatgaggat gctgagactg                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
aatttgggac atgcatacat                                               20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gtctccttgt tgtatggtaa                                               20

```
<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
tgaacaggac tgggtgcagg                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gactgctgct gtggactggc                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ctgactgtac atgagcctga                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ccattcctga ctgtacatga                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
cagttggatg agaaggaacc                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
catgggcagt tggatgagaa                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 61
accgccgggt ggctgtgtcg                                          20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tttgagcgag ggcggcctgg                                          20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gctgtagtgc actttgagcg                                          20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
agactggaat gggctgtagt                                          20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
gcgctgttgt cgagactgga                                          20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggaaatgcgc tgttgtcgag                                          20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ggcttgtact gaagggtgcg                                          20

<210> SEQ ID NO 68
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 68
gtggtgggct tgtactgaag                                              20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
ctgttggtgg tgggcttgta                                              20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
caactgctgt tggtggtggg                                              20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gccttacaac tgctgttggt                                              20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
ttcggttcct ccagggcagc                                              20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ttctagtttt ctgtgcttcc                                              20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
```

```
aataaataac ttccagtttc                                            20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gaatcactct tgttacttct                                            20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
cagcaagaat cactcttgtt                                            20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tttataaata ataatccgtc                                            20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
aagttgaacc actgtagaca                                            20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
atcggccacc acccgcgcgc                                            20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
caaagggtta attaggatct                                            20

<210> SEQ ID NO 81
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 81
cccaaagggt taattaggat                                           20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
aggacagtca tttgatttgt                                           20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ctttgaggac agtcatttga                                           20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctgacagaac aaatgatatg                                           20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
tattgggtat aaaggcttga                                           20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ggtattgggt ataaaggctt                                           20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ctcttttacg catacaggca                                           20
```

```
<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
aggaaggcca actgagtcct                                                 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
ggtcagacgg aagcagaacg                                                 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ccacctggct gcggcgaagc                                                 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
gccgttgccg ttgctaccaa                                                 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
ggcccataca ccggctcgca                                                 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gcttcagcga catggtgagg                                                 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 94
ggacattggc agccgcgggc                                                    20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
gattccatca aaagaaatcg                                                    20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
caactgatgt aagtatatga                                                    20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
ccaaatcaca cttcggactg                                                    20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
ctcatgtgcg gcatcaagta                                                    20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
catttgaaca aaatactctc                                                    20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ctgatagcag agtcagtaaa                                                    20

<210> SEQ ID NO 101

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
gggccactcg agctttgtac                                           20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
aggaatatat ttattttccc                                           20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
cccatacgcg gtgaattctg                                           20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
tggagcccga tccaggctgg                                           20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
agaagtggat cttgatggca                                           20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
ggagaaccat gagcagaggg                                           20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
```
ggcccttctg aagacatgcg                                               20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cactggatat ggaacccctc                                               20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gtgggataca aattctaggc                                               20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
actgaccact gatgaccacg                                               20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
ctgggtctat gagttttagg                                               20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tggaataata ccagcttggg                                               20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
ggcatggcaa cagcttcagt                                               20

<210> SEQ ID NO 114
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 114
taggagatgc agctggaata                                                 20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
gaagcctgga atctttagcc                                                 20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
ccctgcagga gagttctgcc                                                 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ttcagaagta gaacttggct                                                 20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
caattttgtc tttgatcaaa                                                 20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
tgttactaag tattgaaggg                                                 20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
aagtgacctc aggtcccctc                                                 20
```

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
atgttgattt cctaacttgc                                               20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gtataaactg gagttggctg                                               20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
gtgcaaaaca aacaggctga                                               20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
gactggatac atcatatttg                                               20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
ggttgcacgc ctgggctcac                                               20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
tcataggtat tgggtataaa                                               20

<210> SEQ ID NO 127
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 127
ttgattcact ggcatgggcg                                              20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
gatgatgctg gtcttgccgc                                              20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
atcattctag cattaccctg                                              20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
atactaaacc aggctgggcg                                              20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
acatgcatac atcgcatgcg                                              20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
tagaaagaag ggcttgtctc                                              20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
cgcatactgc tgagcaaggg                                              20

```
<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
tagctgaagg ctgagggtgt                                          20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
caccatgttg gctttgctgc                                          20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
actgggtgca ggatgacttc                                          20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
cgtggtaaat ggctgactgc                                          20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
ttggaggcag gtgtcatgga                                          20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tggcgcatgg gcagttggat                                          20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 140
ctttgagcga gggcggcctg                                          20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gtcgagactg gaatgggctg                                          20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
attcctattg gatgttacaa                                          20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
atcttccact gcaagtgaac                                          20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
tatggaatta tggaatagcc                                          20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
gcaagaatca ctcttgttac                                          20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
tgtagacagt gatcacctca                                          20

<210> SEQ ID NO 147
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 147
ggccaaggcc cacttgtctc                                           20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
cactgcggcc tcgaacagca                                           20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
aaattcctca ttttcttttc                                           20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
gttatagtaa tctgtaatca                                           20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
aggattgtaa aatgatacag                                           20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gtaggattgt aaaatgatac                                           20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
```
ttatatatgt aaattatatc                                          20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
aaccactgat ttatacactt                                          20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
ttaaaaacca ctgatttata                                          20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
atatagcact ctgctgtatt                                          20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
taccaagctt gtggcttggg                                          20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
ttataccaag cttgtggctt                                          20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
cctcgatgtt ccacaggcgc                                          20

<210> SEQ ID NO 160
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 160
gagttcacct gcatccaggg                                               20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
tccagttccc tcattggctg                                               20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
ggttccatcc attagatacg                                               20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
ttaaacgaaa catatctttg                                               20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164 gccctgcgc cataattttt                                                20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
ataaactgct ttcaacggtg                                               20
```